United States Patent
Kazama et al.

(10) Patent No.: US 6,511,965 B2
(45) Date of Patent: Jan. 28, 2003

(54) ETHER TYPE LIPID A 1-CARBOXYLIC ACID ANALOGS

(75) Inventors: Yukiko Kazama, Yokohama (JP); Masao Shiozaki, Tokyo (JP); Shinichi Kurakata, Tokyo (JP); Saori Kanai, Sakura (JP)

(73) Assignee: Sankyo Company, Limited, Tokyo (JP)

( * ) Notice: Subject to any disclaimer, the term of this patent is extended or adjusted under 35 U.S.C. 154(b) by 0 days.

(21) Appl. No.: 09/925,815

(22) Filed: Aug. 9, 2001

(65) Prior Publication Data

US 2002/0161221 A1 Oct. 31, 2002

Related U.S. Application Data

(63) Continuation-in-part of application No. PCT/JP00/00726, filed on Feb. 10, 2000.

(30) Foreign Application Priority Data

Feb. 10, 1999 (JP) .............................. 11-032532

(51) Int. Cl.[7] ................. A61K 31/70; C07H 15/04; C07H 11/04; C07H 13/00; C07H 5/04
(52) U.S. Cl. .................. 514/25; 536/53; 536/4.1; 536/117; 536/119; 536/115; 536/55; 514/23; 514/53; 514/42
(58) Field of Search ................ 536/53, 55, 4.1, 536/123.13, 117, 119, 115; 514/53, 23, 25, 42

(56) References Cited

FOREIGN PATENT DOCUMENTS

| JP | 5-194470 A | 3/1993 |
|---|---|---|
| WO | WO95/14026 A | 5/1995 |
| WO | WO96/39411 A | 12/1996 |
| WO | WO98/42719 A | 10/1998 |

OTHER PUBLICATIONS

Imoto et al, "Total Synthesis of *Escherichia coli* Lipid A", Tetrahedron Letters, vol. 26, No. 12, pp. 1545–1548 (1985).
Kusama et al, "Synthesis and Biological Activities of Lipid A Analogs: Modification of a Glycosidically Bound Group . . . ", Chem. Pharm. Bull., vol. 39, No. 12, pp. 3244–3253 (Dec. 1991).
Shiozaki et al, "Synthesis of 2,6–Anhydro–3–deoxy–5–0–phosphono–3–tetradecan amido–4–0–[(R) –3–(tetradecanoyloxy) tetradecanoyl] –D–gylycero–D–ido–heptonic Acid . . .", Tetrahedron Letters, vol. 37, No. 40, pp. 7271–7274 (Sep. 1996).

Mochizuki et al, "Lipid A–Type Pyrancarboxylic Acid Derivatives, their Synthesis and their Biological Activities", Tetrahedron, vol. 56, No. 39, pp. 7691–7703 (Sep. 2000).

*Primary Examiner*—Samuel Barts
*Assistant Examiner*—Michael C. Henry
(74) *Attorney, Agent, or Firm*—Frishauf, Holtz, Goodman & Chick, P.C.

(57) ABSTRACT

A compound of formula (I) below, which exhibits excellent macrophage activity inhibitory action, is useful for the treatment or prophylaxis of inflammatory disorders, autoimmune diseases or septicemia. In a preferred embodiment, $R^1$ and $R^3$ each represents a $C_1$–$C_{20}$ alkanoyl group which may optionally be substituted with one or more substituent groups selected from substituent group A, $R^2$ and $R^4$ each represents a $C_1$–$C_{20}$ alkyl group which may optionally be substituted with one or more substituent groups selected from substituent group A, $R^5$ is a hydrogen atom, a halogen atom, a hydroxy group, or a $C_1$–$C_6$ alkoxy group, and substituent group A is a halogen atom, a hydroxy group, an oxo group, a $C_1$–$C_{20}$ alkoxy group, or a $C_1$–$C_{20}$ alkanoyloxy group.

(I)

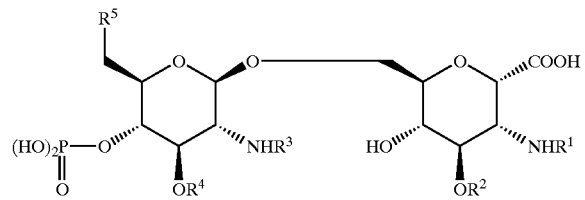

35 Claims, No Drawings

ETHER TYPE LIPID A 1-CARBOXYLIC ACID ANALOGS

This application is a continuation-in-part of International Application PCT/JP00/00726 filed Feb. 10, 2000 (not published in English).

TECHNICAL FIELD

The present invention relates to novel lipid A analogs having excellent macrophage activity inhibitory action and useful as an anti-inflammatory agent or a medicament against autoimmune diseases or septicemia.

BACKGROUND ART

The outermost layer of the cell wall of gram negative bacteria obtained from enterobacteria contains a toxic component (endotoxin) which is not secreted out of the cell. This endotoxin exhibits, in addition to its endotoxic activity, various biological activities such as immunoadjuvant activating action which is related to biophylaxis, macrophage activating action, mitogen activating action, fever producing action, tumor necrosis action, antibody production enhancing action and TNF inducing action.

It has been confirmed that this endotoxin is composed of a lipopolysaccharide and a portion called "lipid A" which is an active center of endotoxic activity (Imoto et al., Tetrahedron Letters, 26, 1545 (1985)).

It has also been revealed that lipid X and lipid Y, each of which is a monosaccharide separated from a variant of $E.$ $coli$ as a precursor for biosynthesis of lipid A, exhibit similar activities to lipid A.

Based on these results, attempts to synthesize derivatives of lipid A, X or Y having useful activity, among the above-described various activities, have been made frequently For example, known is a derivative as described in Japanese Patent Application Laid-Open No. Hei 10-324694.

DISCLOSURE OF THE INVENTION

An object of the present invention is to find a novel lipid A derivative having excellent macrophage activity inhibitory action and useful as an anti-inflammatory agent or a medicament against autoimmune diseases or septicemia.

The present inventors have made a great effort toward fulfilling the above-described object. As a result, it has been found that some series of ether type lipid A 1-carboxylic acid analogs exhibit excellent macrophage activity inhibitory action, leading to the completion of the present invention.

The compounds of the present invention have the general formula (I):

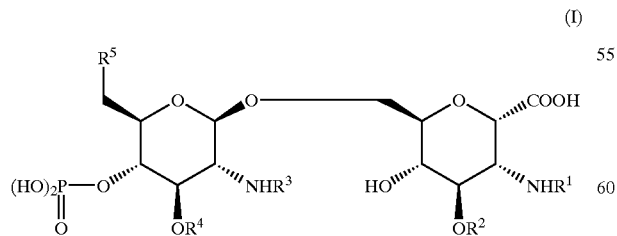

(I)

wherein:

$R^1$ and $R^3$ may be the same or different and each represents a $C_1$–$C_{20}$ alkanoyl group which may optionally be substituted with one or more substituent groups selected from substituent group A, a $C_3$–$C_{20}$ alkenoyl group which may optionally be substituted with one or more substituent groups selected from substituent group A or a $C_3$–$C_{20}$ alkynoyl group which may optionally be substituted with one or more substituent groups selected from substituent group A;

$R^2$ and $R^4$ may be the same or different and each represents a $C_1$–$C_{20}$ alkyl group which may optionally be substituted with one or more substituent groups selected from substituent group A, a $C_2$–$C_{20}$ alkenyl group which may optionally be substituted with one or more substituent groups selected from substituent group A or a $C_2$–$C_{20}$ alkynyl group which may optionally be substituted with one or more substituent groups selected from substituent group A;

$R^5$ is a hydrogen atom, a halogen atom, a hydroxy group, a $C_1$–$C_6$ alkoxy group which may optionally be substituted with an oxo group, a $C_2$–$C_6$ alkenyloxy group which may optionally be substituted with an oxo group, or a $C_2$–$C_6$ alkynyloxy group which may optionally be substituted with an oxo group;

Substituent group A is a group consisting of a halogen atom, a hydroxy group, an oxo group, a $C_1$–$C_{20}$ alkoxy group which may optionally be substituted with an oxo group, a $C_2$–$C_{20}$ alkenyloxy group which may optionally be substituted with an oxo group, a $C_2$–$C_{20}$ alkynyloxy group which may optionally be substituted with an oxo group, a $C_1$–$C_{20}$ alkanoyloxy group which may optionally be substituted with an oxo group, a $C_3$–$C_{20}$ alkenoyloxy group which may optionally be substituted with an oxo group, or a $C_3$–$C_{20}$ alkynoyloxy group which may optionally be substituted with an oxo group;

or a pharmaceutically acceptable salt or ester thereof.

Preferred compounds of the present invention are:

2) a compound wherein $R^1$ is a $C_4$–$C_{18}$ alkanoyl group optionally substituted with one or more substituent groups selected from substituent group A;

3) a compound wherein $R^1$ is a $C_8$–$C_{16}$ alkanoyl group optionally substituted with one or more substituent groups selected from substituent group A;

4) a compound wherein $R^1$ is an unsubstituted $C_{12}$–$C_{14}$ alkanoyl group or a $C_{12}$–$C_{14}$ alkanoyl group substituted with a hydroxy group;

5) a compound wherein $R^1$ is an unsubstituted lauroyl or myristoyl group or a lauroyl or myristoyl group substituted with a hydroxy group;

6) a compound wherein $R^2$ is a $C_4$–$C_{18}$ alkyl group optionally substituted with one or more substituent groups selected from substituent group A;

7) a compound wherein $R^2$ is a $C_8$–$C_{16}$ alkyl group optionally substituted with one or more substituent groups selected from substituent group A;

8) a compound wherein $R^2$ is an unsubstituted $C_{12}$–$C_{14}$ alkyl group or a $C_{12}$–$C_{14}$ alkyl group substituted with a hydroxy group;

9) a compound wherein $R^2$ is an unsubstituted dodecyl or tetradecyl group or a dodecyl or tetradecyl group substituted with a hydroxy group;

10) a compound wherein $R^3$ is an unsubstituted $C_1$–$C_{16}$ alkanoyl group;

11) a compound wherein $R^3$ is an unsubstituted $C_1$–$C_8$ alkanoyl group;

12) a compound wherein $R^3$ is an unsubstituted $C_1$–$C_4$ alkanoyl group;

13) a compound wherein $R^3$ is an acetyl group or a propionyl group;
14) a compound wherein $R^3$ is an acetyl group;
15) a compound wherein $R^4$ is a $C_4$–$C_{18}$ alkyl group optionally substituted with one or more substituent groups selected from substituent group A;
16) a compound wherein $R^4$ is a $C_8$–$C_{16}$ alkyl group optionally substituted with one or more substituent groups selected from substituent group A;
17) a compound wherein $R^4$ is a $C_{12}$–$C_{14}$ alkyl group substituted with a fluorine atom, a hydroxy group, an unsubstituted $C_{12}$–$C_{14}$ alkoxy group or an unsubstituted $C_{12}$–$C_{14}$ alkanoyloxy group;
18) a compound wherein $R^4$ is a dodecyl group or a tetradecyl group substituted with a dodecyloxy group or a tetradecyloxy group;
19) a compound wherein $R^4$ is a dodecyl group or a tetradecyl group substituted with a lauroyloxy group or a myristoyloxy group;
20) a compound wherein $R^5$ is a halogen atom, a hydroxy group or an unsubstituted $C_1$–$C_6$ alkoxy group; or
21) a compound wherein $R^5$ is a fluorine atom, a hydroxy group or a methoxy group.

More preferred compounds are selected from:

2,6-anhydro-7-O-[2-acetylamino-2-deoxy-6-O-methyl-4-O-phosphono-3-O-{(R)-3-tetradecanoyloxytetradecyl}-β-D-glucopyranosyl]-3-{(R)-3-hydroxytetradecanoylamino}-4-O-{(R)-3-hydroxytetradecyl}-3-deoxy-D-glycero-D-ido-heptonic acid;

2,6-anhydro-7-O-[2-acetylamino-2-deoxy-4-O-phosphono-3-O-{(R)-3-tetradecanoyloxytetradecyl}-β-D-glucopyranosyl]-3-{(R)-3-hydroxytetradecanoylamino}-4-O-{(R)-3-hydroxytetradecyl}-3-deoxy-D-glycero-D-ido-heptonic acid;

2,6-anhydro-7-O-[2-acetylamino-2,6-dideoxy-6-fluoro-4-O-phosphono-3-O-{(R)-3-tetradecanoyloxytetradecyl}-β-D-glucopyranosyl]-3-{(R)-3-hydroxytetradecanoylamino}-4-O-{(R)-3-hydroxytetradecyl}-3-deoxy-D-glycero-D-ido-heptonic acid;

2,6-anhydro-7-O-[2-acetylamino-2-deoxy-3-O-{(R)-3-dodecyloxytetradecyl}-6-O-methyl-4-O-phosphono-β-D-glucopyranosyl]-3-{(R)-hydroxytetradecanoylamino}-4-O-{(R)-3-hydroxytetradecyl}-3-deoxy-D-glycero-D-ido-heptonic acid;

2,6-anhydro-7-O-[2-acetylamino-2-deoxy-3-O-{(R)-3-dodecyloxytetradecyl}-4-phosphono-β-D-glucopyranosyl]-3-{(R)-3-hydroxytetradecanoylamino}-4-O-{(R)-3-hydroxytetradecyl}-3-deoxy-D-glycero-D-ido-heptonic acid; or 2,6-anhydro-7-O-[2-acetylamino-2,6-dideoxy-3-O-{(R)-3-dodecyloxytetradecyl}-6-fluoro-4-O-phosphono-β-D-glucopyranosyl]-3-{(R)-3-hydroxytetradecanoylamino}-4-O-{(R)-3-hydroxytetradecyl}-3-deoxy-D-glycero-D-ido-heptonic acid.

The present invention includes a medicament containing a compound of formula (I) as an active ingredient, especially a composition for the treatment or prophylaxis of an inflammatory disorder, a composition for the treatment or prophylaxis of an autoimmune disease or a composition for the treatment or prophylaxis of septicemia.

The "$C_1$–$C_{20}$ alkanoyl" moiety, which is described in the definition of $R^1$ and $R^3$ as "a $C_1$–$C_{20}$ alkanoyl group which may be optionally substituted with one or more substituent groups selected from substituent group A" and in the definition of substituent group A as "a $C_1$–$C_{20}$ alkanoyloxy group which may be optionally substituted with an oxo group", includes a straight or branched chain $C_1$–$C_{20}$ alkanoyl group such as formyl, acetyl, propionyl, butyryl, isobutyryl, valeryl, isovaleryl, pivaloyl, hexanoyl, isohexanoyl, heptanoyl, isoheptanoyl, octanoyl, isooctanoyl, nonanoyl, isononanoyl, decanoyl, isodecanoyl, undecanoyl, isoundecanoyl, lauroyl, isolauroyl, tridecanoyl, isotridecanoyl, myristoyl, pentadecanoyl, palmitoyl, heptadecanoyl, stearoyl, isostearoyl, nonadecanoyl, or icosanoyl.

A preferred alkanoyl moiety of $R^1$ and substituent group A is a $C_4$–$C_{18}$ alkanoyl group; a more preferred moiety is a $C_8$–$C_{16}$ alkanoyl group; a still more preferred moiety is a $C_{12}$–$C_{14}$ alkanoyl group; and the most preferred moiety is the lauroyl group or the myristoyl group.

A preferred alkanoyl moiety of $R^3$ is a $C_1$–$C_{16}$ alkanoyl group; a more preferred moiety is a $C_1$–$C_8$ alkanoyl group; a more preferred moiety is a $C_1$–$C_4$ alkanoyl group; a still more preferred moiety is the acetyl group or the propionyl group; and the most preferred moiety is the acetyl group.

The "$C_3$–$C_{20}$ alkenoyl" moiety, which is described in the definition of $R^1$ and $R^3$ as "a $C_3$–$C_{20}$ alkenoyl group which may be optionally substituted with one or more substituent groups selected from substituent group A" and in the definition of substituent group A as "a $C_3$–$C_{20}$ alkenoyloxy group which may be optionally substituted with an oxo group", includes a group having 1 to 3 double bonds in the corresponding $C_3$–$C_{20}$ alkanoyl group described above as the $C_1$–$C_{20}$ alkanoyl group.

A preferred alkenoyl moiety of $R^1$ and substituent group A is a $C_4$–$C_{18}$ alkenoyl group; a more preferred group is a $C_{12}$–$C_{14}$ alkenoyl group; and the most preferred group is the 9-tetradecenoyl group.

A preferred alkenoyl moiety of $R^3$ is a $C_3$–$C_{16}$ alkenoyl group; a more preferred moiety is a $C_3$–$C_4$ alkenoyl group; and the most preferred moiety is the 3-butenoyl group. The "$C_3$–$C_{20}$ alkynoyl" moiety, which is described in the definition of $R^1$ and $R^3$ as "a $C_3$–$C_{20}$ alkynoyl group which may be optionally substituted with one or more substituent groups selected from substituent group A" and in the definition of substituent group A as "a $C_3$–$C_{20}$ alkynoyloxy group which may be optionally substituted with an oxo group", includes a group having 1 to 3 triple bonds in the corresponding $C_3$–$C_{20}$ alkanoyl group described above as the $C_1$–$C_{20}$ alkanoyl group.

A preferred alkynoyl moiety of $R^1$ and substituent group A is a $C_4$–$C_{18}$ alkynoyl group; a more preferred moiety is a $C_{12}$–$C_{14}$ alkynoyl group; and the most preferred moiety is the 9-tetradecynoyl group.

A preferred alkynoyl moiety of $R^3$ is a $C_3$–$C_{16}$ alkynoyl group; a more preferred moiety is a $C_3$–$C_4$ alkynoyl group; and the most preferred moiety is the 3-butynoyl group.

The "$C_1$–$C_{20}$ alkyl" group, which is described in the definition of $R^2$ and $R^4$ as "a $C_1$–$C_{20}$ alkyl group which may be optionally substituted with one or more substituent groups selected from substituent group A" includes a straight or branched chain $C_1$–$C_{20}$ alkyl group such as methyl, ethyl, propyl, isopropyl, butyl, isobutyl, sec-butyl, tert-butyl, pentyl, isopentyl, 2-methylbutyl, neopentyl, 1-ethylpropyl, hexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3- dimethylbutyl, 2,3-dimethylbutyl, 2-ethylbutyl, heptyl, 1-methylhexyl, 2-methylhexyl, 3-methylhexyl, 4-methylhexyl, 5-methylhexyl, 1-propylbutyl, 4,4-dimethylpentyl, octyl, 1-methylheptyl, 2-methylheptyl, 3-methylheptyl, 4-methylheptyl, 5-methylheptyl, 6-methylheptyl, 1-propylpentyl, 2-ethylhexyl, 5,5-dimethylhexyl, nonyl, 3-methyloctyl, 4-methyloctyl, 5-methyloctyl, 6-methyloctyl, 1-propylhexyl, 2-ethylheptyl, 6,6-dimethylheptyl, decyl, 1-methylnonyl, 3-methylnonyl, 8-methylnonyl, 3-ethyloctyl, 3,7-dimethyloctyl, 7,7-dimethyloctyl, undecyl, 4,8-dimethylnonyl, dodecyl, tridecyl, tetradecyl, pentadecyl, 3,7,11-trimethyldodecyl, hexadecyl, 4,8,12-trimethyltridecyl, 1-methylpentadecyl, 14-methylpentadecyl, 13,13-dimethyltetradecyl, heptadecyl, 15-methylhexadecyl, octadecyl, 1-methylheptadecyl, nonadecyl, icosyl, or 3,7,11,15-tetramethylhexadecyl.

A preferred alkyl group is a $C_4$–$C_{18}$ alkyl group, a more preferred group is a $C_8$–$C_{16}$ alkyl group, a still more preferred group is a $C_{12}$–$C_{14}$ alkyl group, and the most preferred groups are the dodecyl group or the tetradecyl group.

The "$C_2$–$C_{20}$ alkenyl" group, which is described in the definition of fe and $R^4$ as "a $C_2$–$C_{20}$ alkenyl group which may be optionally substituted with one or more substituent groups selected from substituent group A" includes a group having 1 to 3 double bonds in the corresponding $C_2$–$C_{20}$ alkyl group described above as the $C_1$–$C_{20}$ alkyl group. A preferred alkenyl group is a $C_4$–$C_{18}$ alkenyl group, a more preferred group is a $C_{12}$–$C_{14}$ alkenyl group, and the most preferred group is the 9-tetradecenyl group.

The "$C_2$–$C_{20}$ alkynyl" group which is described in the definition of $R^2$ and $R^4$ as "a $C_2$–$C_{20}$ alkynyl group which may be optionally substituted with one or more substituent groups selected from substituent group A" includes a group having 1 to 3 triple bonds in the corresponding $C_2$–$C_{20}$ alkyl group described above as the $C_1$–$C_{20}$ alkyl group. A preferred alkynyl group is a $C_4$–$C_{18}$ alkynyl group, a more preferred group is a $C_{12}$–$C_{14}$ alkynyl group, and the most preferred group is the 9-tetradecynyl group.

The halogen atom in the definition of $R^5$ and substituent group A includes, for example, the fluorine, chlorine, bromine or iodine atom. A preferred halogen atom is the fluorine, chlorine or bromine atom, and the more preferred atom is fluorine. The "$C_1$–$C_6$ alkoxy" group, which is described in the definition of $R^5$ as "a $C_1$–$C_6$ alkoxy group which may optionally be substituted with an oxo group" includes, for example, a straight or branched chain $C_1$–$C_6$ alkoxy group such as a methoxy, ethoxy, propoxy, isopropoxy, butoxy, isobutoxy, sec-butoxy, tert-butoxy, pentyloxy, isopentyloxy, 2-methylbutyloxy, neopentyloxy, 1-ethylpropyloxy, hexyloxy, isohexyloxy, 4-methylpentyloxy, 3-methylpentyloxy, 2-methylpentyloxy, 1-methylpentyloxy, 3,3-dimethylbutyloxy, 2,2-dimethylbutyloxy, 1,1-dimethylbutyloxy, 1,2-dimethylbutyloxy, 1,3-dimethylbutyloxy, 2,3-dimethylbutyloxy or 2-ethylbutyloxy. A preferred alkoxy group is a $C_1$–$C_4$ straight or branched chain alkoxy group, and the more preferred group is the methoxy group.

The "$C_2$–$C_6$ alkenyloxy" group, which is described in the definition of $R^5$ as "a $C_{1-C6}$ alkenyloxy group which may optionally be substituted with an oxo group" includes a group having 1 to 3 double bonds in the corresponding $C_2$–$C_6$ alkoxy group described above as the $C_1$–$C_6$ alkoxy group. A preferred alkenyloxy group is a $C_2$–$C_4$ alkenyloxy group and the most preferred group is the 3-butenyloxy group.

The "$C_2$–$C_6$ alkynyloxy" group, which is described in the definition of $R^5$ as "a $C_2$–$C_6$ alkynyloxy group which may optionally be substituted with an oxo group" includes a group having 1 to 3 triple bonds in the corresponding $C_2$–$C_6$ alkoxy group described above as the $C_1$–$C_6$ alkoxy group. A preferred alkynyloxy group is a $C_2$–$C_4$ alkynyloxy group and the most preferred group is the 3-butynyloxy group.

The "$C_1$–$C_{20}$ alkoxy" group, which is described in the definition of substituent group A as "a $C_1$–$C_{20}$ alkoxy group which may optionally be substituted with an oxo group" includes, for example, a straight or branched chain $C_1$–$C_{20}$ alkoxy group, in which an oxygen atom is attached to the $C_1$–$C_{20}$ alkyl group described above, such as a methoxy, ethoxy, propoxy, isopropoxy, butoxy, isobutoxy, sec-butoxy, tert-butoxy, pentyloxy, isopentyloxy, 2-methylbutyloxy, neopentyloxy, 1-ethylpropyloxy, hexyloxy, isohexyloxy, 4-methylpentyloxy, 3-methylpentyloxy, 2-methylpentyloxy, 1-methylpentyloxy, 3,3-dimethylbutyloxy, 2,2-dimethylbutyloxy, 1,1-dimethylbutyloxy, 1,2-dimethylbutyloxy, 1,3-dimethylbutyloxy, 2,3-dimethylbutyloxy, 2-ethylbutyloxy, heptyloxy, 4-methylhexyloxy, 1-propylbutyloxy, 4,4-dimethylpentyloxy, octyloxy, 6-methylheptyloxy, 5,5-dimethylhexyloxy, nonyloxy, decyloxy, 1-methylnonyloxy, 3-methylnonyloxy, 8-methylnonyloxy, 3-ethyloctyloxy, 3,7-dimethyloctyloxy, 7,7-dimethyloctyloxy, undecyloxy, 4,8-dimethylnonyloxy, dodecyloxy, tridecyloxy, tetradecyloxy, pentadecyloxy, 3,7,11-trimethyldodecyloxy, hexadecyloxy, 4,8,12-trimethyltridecyloxy, 1-methylpentadecyloxy, 14-methylpentadecyloxy, 13,13-dimethyltetradecyloxy, heptadecyloxy, octadecyloxy, 1-methylheptadecyloxy, nonadecyloxy, icosyloxy or 3,7,11,15-tetramethylhexadecyloxy group. A preferred alkoxy group is a $C_4$–$C_{18}$ alkoxy group, a more preferred group is a $C_8$–$C_{16}$ alkoxy group, a still more preferred group is a $C_{12}$–$C_{14}$ alkoxy group and the most preferred group is the dodecyloxy group or the tetradecyloxy group.

The "$C_2$–$C_{20}$ alkenyloxy" group, which is described in the definition of substituent group A as "a $C_2$–$C_{20}$ alkenyloxy group which may optionally be substituted with an oxo group" includes a group having 1 to 3 double bonds in the corresponding $C_2$–$C_{20}$ alkoxy group described above as the $C_1$–$C_{20}$ alkoxy group. A preferred alkenyloxy group is a $C_4$–$C_{18}$ alkenyloxy group, a more preferred group is a $C_{12}$–$C_{14}$ alkenyloxy group and the most preferred group is the 9-tetradecenyloxy group.

The "$C_2$–$C_{20}$ alkynyloxy" group, which is described in the definition of substituent group A as "a $C_2$–$C_{20}$ alkynyloxy group which may optionally be substituted with an oxo group" includes a group having 1 to 3 triple bonds in the corresponding $C_2$–$C_{20}$ alkoxy group described above as the $C_1$–$C_{20}$ alkoxy group. A preferred alkynyloxy group is a $C_4$–$C_{18}$ alkynyloxy group, a more preferred group is a $C_{12}$–$C_{14}$ alkynyloxy group and the most preferred group is the 9-tetradecynyloxy group.

The preferred substitution position of substituent group A in the formula (I) is the 3-position.

Preferably $R^1$ is a $C_4$–$C_{18}$ alkanoyl group which may optionally be substituted with one or more substituent groups selected from substituent group A. More preferably $R^1$ is a $C_8$–$C_{16}$ alkanoyl group which may optionally be substituted with one or more substituent groups selected from substituent group A. Still more preferably $R^1$ is a $C_{12}$–$C_{14}$ alkanoyl group which may optionally be substituted with one or more substituent groups selected from substituent group A. Most preferably $R^1$ is an unsubstituted lauroyl group or myristoyl group or a lauroyl or myristoyl group substituted with a hydroxy group.

Preferably $R^2$ is a $C_4$–$C_{18}$ alkyl group which may optionally be substituted with one or more substituent groups selected from substituent group A. More preferably $R^2$ is a $C_8$–$C_{16}$ alkyl group which may optionally be substituted with one or more substituent groups selected from substituent group A. Still more preferably $R^2$ is a $C_{12}$–$C_{14}$ alkyl group which may optionally be substituted with one or more hydroxy groups. Most preferably $R^2$ is an unsubstituted dodecyl group or tetradecyl group or a dodecyl or tetradecyl group substituted with a hydroxy group.

Preferably $R^3$ is an unsubstituted $C_1$–$C_{16}$ alkanoyl group. More preferably $R^3$ is an unsubstituted $C_1$–$C_8$ alkanoyl group. More preferably $R^3$ is a $C_1$–$C_{14}$ alkanoyl group. Still more preferably $R^3$ is an acetyl group or propionyl group. Most preferably $R^3$ is an acetyl group.

Preferably $R^4$ is a $C_4$–$C_{18}$ alkyl group which may optionally be substituted with one or more substituent groups selected from substituent group A. More preferably $R^4$ is a $C_8$–$C_{16}$ alkyl group which may optionally be substituted with one or more substituent groups selected from substituent group A. Still more preferably $R^4$ is a $C_{12}$–$C_{14}$ alkyl group which is substituted with a fluorine atom, a hydroxy group, an unsubstituted $C_{12}$–$C_{14}$ alkoxy group, or an unsubstituted $C_{12}$–$C_{14}$ alkanoyloxy group. Most preferably $R^4$ is a dodecyl group or tetradecyl group substituted with a dodecyloxy group, a tetradecyloxy group, a lauroyloxy group or a myristoyloxy group.

Preferably $R^5$ is a halogen atom, hydroxy group or an unsubstituted $C_1$–$C_6$ alkoxy group. More preferably $R^5$ is a fluorine atom, a hydroxy group, or a methoxy group.

The compound of formula (I) can be converted to a salt. A preferred salt is an alkali metal salt or an alkaline earth metal salt such as a sodium salt, a potassium salt, a magnesium salt or a calcium salt, or a salt of an organic base such as a triethylamnine salt or a trimethylamine salt.

In some case, when a compound of formula (I) of the present invention is allowed to stand in contact with the atmosphere it may absorb water or may take up water to form a hydrate. The present invention encompasses such hydrates.

In addition, a compound of formula (I) of the present invention may take up a solvent to form a solvate. The present invention encompasses such solvates.

The compound of formula (I) can form an ester and the ester-forming group includes the following groups (a) to (f). These ester groups include protecting groups which can be cleaved by a biological method such as hydrolysis in vivo and protecting groups for a chemical reaction which may be cleaved by a chemical method such as hydrogenolysis, hydrolysis, electrolysis or photolysis.

(a) —$CHR^aR^b$
(b) —$CHR^cR^d$
(c) —$(CHR^e)_n$—$OCOR^f$
(d) —$(CHR^e)_n$—$OR^g$
(e) —$SiR^gR^hR^i$
(f) —$CH_2$—Ph—$COOR^i$ wherein:

n is 1 or 2;

Ph is a phenyl group;

$R^a$ is a hydrogen atom, a lower alkyl group, a lower alkyl group substituted with an aryl group, a halogeno lower alkyl group, a lower alkenyl group, a lower alkynyl group, an aliphatic acyl group, or an aliphatic acyl group substituted with an aryl group. Preferably $R^a$ is a hydrogen atom, a lower alkyl group, a halogeno lower alkyl group, a lower alkenyl group, or a lower alkynyl group. More preferably $R^a$ is a hydrogen atom, a $C_1$–$C_3$ alkyl group, a halogeno $C_1$–$C_3$ alkyl group, a $C_2$–$C_3$ alkenyl group, or a $C_2$–$C_3$ alkynyl group.

$R^b$ is hydrogen or a lower alkyl group. Preferably $R^b$ is a hydrogen atom.

$R^c$ is an aryl group or a substituted aryl group (said substituents are a lower alkyl group, a lower alkoxy group, a halogen atom or a nitro group). Preferably $R^c$ is a loweralkoxylated aryl group, a halogenated aryl group, or a nitrated aryl group. More preferably $R^c$ is a loweralkoxylated phenyl group, a halogenated phenyl group, or a nitrated phenyl group.

$R^d$ is a hydrogen atom or a group as defined in $R^c$.

$R^e$ is hydrogen or a lower alkyl group. Preferably $R^e$ is a hydrogen atom or a $C_1$–$C_3$ alkyl group.

$R^f$ is a lower alkyl group, a lower alkoxy group or a group as defined in $R^c$. Preferably $R^f$ is a lower alkyl group or a lower alkoxy group. More preferably $R^f$ is a $C_1$–$C_3$ alkyl group or a $C_1$–$C_3$ alkoxy group.

$R^e$ and $R^f$ taken together may be a phthalidyl or a mono- or di-substituted phthalidyl group (said substituent is a lower alkyl group or lower alkoxy group).

$R^g$ and $R^h$ may be the same or different and each represent a lower alkyl group or a group as defined in $R^c$. Preferably $R^g$ and $R^h$ each represent a lower alkyl group. More preferably $R^g$ and $R^h$ each represent a $C_1$–$C_3$ alkyl group.

$R^i$ is a lower alkyl group and preferably $R^i$ is a $C_1$–$C_3$ alkyl group.

A typical protecting group which may be cleaved by a biological method such as hydrolysis in vivo and a protecting group for a chemical reaction are as follows:

A preferable protecting group which may be cleaved by a biological method is methoxymethyl, 1-ethoxyethyl, 1-methyl-1-methoxyethyl, tert-butoxymethyl, phenoxymethyl, acetoxymethyl, pivaloyloxymethyl, cyclopentanoyloxymethyl, 1-cyclohexanoyloxybutyl, benzoyloxymethyl, methoxycarbonyloxymethyl or 2-propoxycarbonyloxyethyl.

A preferred protecting group for a chemical reaction is methyl, ethyl, n-propyl, isopropyl, n-butyl, isobutyl, sec-butyl, tert-butyl, n-pentyl, isopentyl, 2-methylbutyl, neopentyl, 1-ethylpropyl, n-hexyl, 4-methylpentyl, 3-methylpentyl, 2-methylpentyl, 1-methylpentyl, 3,3-dimethylbutyl, 2,3-dimethylbutyl, 2-ethylbutyl, ethenyl, 1-propenyl, 2-propenyl, 1-methyl-2-propenyl, 2-methyl-1-propenyl, 2-ethyl-2-propenyl, 1-butenyl, 3-methyl-2-butenyl, 3-butenyl, 1-methyl-3-butenyl, 2-pentenyl, 1-methyl-3-pentenyl, 2-hexenyl, ethynyl, 2-propynyl, 2-methyl-2-propynyl, 2-butynyl, 1-methyl-2-butynyl, 1-ethyl-2-butynyl, 2-pentynyl, 3-pentynyl, 4-pentynyl, 2-hexynyl, acetylmethyl, benzyl, phenethyl, 3-phenylpropyl, a-naphthylmethyl, β-naphthylmethyl, diphenylmethyl, triphenylmethyl, 6-phenylhexyl, α-naphthyldiphenylnethyl, 9-anthrylmethyl, 4-methylbenzyl, 2,4,6-trimethylbenzyl, 3,4,5-trimethylbenzyl, 4-methoxybenzyl, 4-methoxyphenyldiphenylmethyl, 2-nitrobenzyl, 4-nitrobenzyl, 4-chlorobenzyl, 4-bromobenzyl, 4cyanobenzyl, 4-cyanobenzyldiphenylmethyl, bis(2-nitrophenyl)methyl, 4-methoxycarbonylbenzyl, trimethylsilyl, triethylsilyl, isopropyldimethylsilyl, tert-butyldimethylsilyl, methyldiisopropylsilyl, methyl-di-tert-butylsilyl, triisopropylsilyl, methyldiphenylsilyl, isopropyldiphenylsilyl, butyldiphenylsilyl, or phenyldiisopropylsilyl group.

The compound of formula (I) has some asymmetric centers and can exist as stereoisomers having S- or R-configuration at each asymmetric center. The present invention encompasses an individual isomer or a mixture of these isomers.

The compounds in the following table are intended to illustrate typical compounds of the present invention and are not intended to limit the scope of the invention. In the table the following abbreviations are used:

Ac: acetyl group, Bu: butyl group, Byr: butyryl group, Dc: decyl group, Dco: decanoyl, Ddc: dodecyl group, Ei: eicosyl group, Eicn: eicosanoyl group, Fo: formyl group, Hx: hexylgroup, Hdc: hexadecyl group, Hxn: hexanoyl group, Lau: lauroyl group (dodecanoyl group), Me: methyl group, Myr: myristoyl group (tetradecanoyl group), Oc: octyl group, Odc: octadecyl group, Octo: octanoyl group, =O: oxo group (carbonyl group taken together with carbon), Pal: palmitoyl group (hexadecanoyl group) Prn: propionyl group, Ste: stearoyl group (octadecanoyl group), Tedc: tetradecyl group, Val: valeryl group.

TABLE 1

| compound No | $R^1$ | $R^2$ | $R^3$ | $R^4$ | $R^5$ |
|---|---|---|---|---|---|
| 1 | 3-OH-Lau | 3-OH-Ddc | Fo | 3-OMyr-Tedc | OMe |
| 2 | 3-OH-Lau | 3-OH-Ddc | Ac | 3-OMyr-Tedc | OMe |
| 3 | 3-OH-Lau | 3-OH-Ddc | Prn | 3-OMyr-Tedc | OMe |
| 4 | 3-OH-Lau | 3-OH-Ddc | Byr | 3-OMyr-Tedc | OMe |
| 5 | 3-OH-Lau | 3-OH-Ddc | Hxn | 3-OMyr-Tedc | OMe |
| 6 | 3-OH-Lau | 3-OH-Ddc | Octo | 3-OMyr-Tedc | OMe |
| 7 | Myr | Tedc | Fo | 3-OMyr-Tedc | OMe |
| 8 | Myr | Tedc | Ac | 3-OMyr-Tedc | OMe |
| 9 | Myr | Tedc | Pm | 3-OMyr-Tedc | OMe |
| 10 | Myr | Tedc | Byr | 3-OMyr-Tedc | OMe |
| 11 | Myr | Tedc | Hxn | 3-OMyr-Tedc | OMe |
| 12 | 3-OH-Myr | 3-OH-Tedc | Fo | 3-OMyr-Tedc | OMe |
| 13 | 3-OH-Myr | 3-OH-Tedc | Ac | 3-OMyr-Tedc | OMe |
| 14 | 3-OH-Myr | 3-OH-Tedc | Prn | 3-OMyr-Tedc | OMe |
| 15 | 3-OH-Myr | 3-OH-Tedc | Byr | 3-OMyr-Tedc | OMe |
| 16 | 3-OH-Myr | 3-OH-Tedc | Val | 3-OMyr-Tedc | OMe |
| 17 | 3-OH-Myr | 3-OH-Tedc | Hxn | 3-OMyr-Tedc | OMe |
| 18 | 3-OH-Myr | 3-OH-Tedc | Octo | 3-OMyr-Tedc | OMe |
| 19 | 3-OH-Myr | 3-OH-Tedc | Dco | 3-OMyr-Tedc | OMe |
| 20 | 3-OH-Myr | 3-OH-Tedc | Lau | 3-OMyr-Tedc | OMe |
| 21 | 3-OH-Myr | 3-OH-Tedc | Myr | 3-OMyr-Tedc | OMe |
| 22 | 3-OH-Myr | 3-OH-Tedc | Pal | 3-OMyr-Tedc | OMe |
| 23 | 3-OH-Myr | 3-OH-Tedc | Ste | 3-OMyr-Tedc | OMe |
| 24 | 3-OH-Myr | 3-OH-Tedc | Eicn | 3-OMyr-Tedc | OMe |
| 25 | 3-OH-Myr | 3-OH-Tedc | 3-OAc-Byr | 3-OByr-Bu | OMe |
| 26 | 3-OH-Myr | 3-OH-Tedc | 3-OByr-Hxn | 3-OHxn-Hx | OMe |
| 27 | 3-OH-Myr | 3-OH-Tedc | 3-OHxn-Octo | 3-OOcto-Oc | OMe |
| 28 | 3-OH-Myr | 3-OH-Tedc | 3-OOcto-Dco | 3-ODco-Dc | OMe |
| 29 | 3-OH-Myr | 3-OH-Tedc | 3-ODco-Lau | 3-OLau-Ddc | OMe |
| 30 | 3-OH-Myr | 3-OH-Tedc | 3-OLau-Myr | 3-OMyr-Tedc | OMe |
| 31 | 3-OH-Myr | 3-OH-Tedc | 3-OH-Myr | 3-OMyr-Tedc | OMe |
| 32 | 3-OH-Myr | 3-OH-Tedc | 3-OLau-Myr | 3-OH-Tedc | OMe |
| 33 | 3-OH-Myr | 3-OH-Tedc | 3-OH-Myr | 3-OH-Tedc | OMe |
| 34 | 3-OH-Myr | 3-OH-Tedc | 3-(=O)-Myr | 3-OH-Tedc | OMe |
| 35 | 3-OH-Myr | 3-OH-Tedc | 3-OH-Myr | 3-(=O)-Tedc | OMe |
| 36 | 3-OH-Myr | 3-OH-Tedc | 2-F-3-OLau-Myr | 2-F-3-OMyr-Tedc | OMe |
| 37 | 3-OH-Myr | 3-OH-Tedc | 2-F-3-OH-Dco | 3-OMyr-Tedc | OMe |
| 38 | 3-OH-Myr | 3-OH-Tedc | 2-Cl-3-OLau-Myr | 2-Cl-3-OMyr-Tedc | OMe |
| 39 | 3-OH-Myr | 3-OH-Tedc | 3-OLau-Myr | 3-OMyr-Ddc | OMe |
| 40 | 3-OH-Myr | 3-OH-Tedc | 3-OLau-Myr | 3-OMyr-Ddc | OMe |
| 41 | 3-OH-Myr | 3-OH-Tedc | 3-OLau-Lau | 3-OMyr-Tedc | OMe |
| 42 | 3-OH-Myr | 3-OH-Tedc | 3-OMyr-Pal | 3-OPal-Hdc | OMe |
| 43 | 3-OH-Myr | 3-OH-Tedc | 3-OPal-Ste | 3-OSte-Odc | OMe |
| 44 | 3-OH-Myr | 3-OH-Tedc | 3-OSte-Eicn | 3-OEicn-Ei | OMe |
| 45 | 3-OH-Lau | 3-OH-Ddc | Fo | 3-OMyr-Tedc | OH |
| 46 | 3-OH-Lau | 3-OH-Ddc | Ac | 3-OMyr-Tedc | OH |
| 47 | 3-OH-Lau | 3-OH-Ddc | Prn | 3-OMyr-Tedc | OH |
| 48 | 3-OH-Lau | 3-OH-Ddc | Byr | 3-OMyr-Tedc | OH |
| 49 | 3-OH-Lau | 3-OH-Ddc | Hxn | 3-OMyr-Tedc | OH |
| 50 | 3-OH-Lau | 3-OH-Ddc | Octo | 3-OMyr-Tedc | OH |
| 51 | Myr | Tedc | Fo | 3-OMyr-Tedc | OH |

TABLE 1-continued

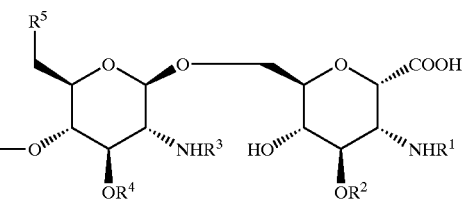

| compound No | $R^1$ | $R^2$ | $R^3$ | $R^4$ | $R^5$ |
|---|---|---|---|---|---|
| 52 | Myr | Tedc | Ac | 3-OMyr-Tedc | OH |
| 53 | Myr | Tedc | Prn | 3-OMyr-Tedc | OH |
| 54 | Myr | Tedc | Byr | 3-OMyr-Tedc | OH |
| 55 | Myr | Tedc | Hxn | 3-OMyr-Tedc | OH |
| 56 | 3-OH-Myr | 3-OH-Tedc | Fo | 3-OMyr-Tedc | OH |
| 57 | 3-OH-Myr | 3-OH-Tedc | Ac | 3-OMyr-Tedc | OH |
| 58 | 3-OH-Myr | 3-OH-Tedc | Prn | 3-OMyr-Tedc | OH |
| 59 | 3-OH-Myr | 3-OH-Tedc | Byr | 3-OMyr-Tedc | OH |
| 60 | 3-OH-Myr | 3-OH-Tedc | Val | 3-OMyr-Tedc | OH |
| 61 | 3-OH-Myr | 3-OH-Tedc | Hxn | 3-OMyr-Tedc | OH |
| 62 | 3-OH-Myr | 3-OH-Tedc | Octo | 3-OMyr-Tedc | OH |
| 63 | 3-OH-Myr | 3-OH-Tedc | Dco | 3-OMyr-Tedc | OH |
| 64 | 3-OH-Myr | 3-OH-Tedc | Lau | 3-OMyr-Tedc | OH |
| 65 | 3-OH-Myr | 3-OH-Tedc | Myr | 3-OMyr-Tedc | OH |
| 66 | 3-OH-Myr | 3-OH-Tedc | Pal | 3-OMyr-Tedc | OH |
| 67 | 3-OH-Myr | 3-OH-Tedc | Ste | 3-OMyr-Tedc | OH |
| 68 | 3-OH-Myr | 3-OH-Tedc | Eicn | 3-OMyr-Tedc | OH |
| 69 | 3-OH-Myr | 3-OH-Tedc | 3-OAc-Byr | 3-OByr-Bu | OH |
| 70 | 3-OH-Myr | 3-OH-Tedc | 3-OByr-Hxn | 3-OHxn-Hx | OH |
| 71 | 3-OH-Myr | 3-OH-Tedc | 3-OHxn-Octo | 3-OOcto-Oc | OH |
| 72 | 3-OH-Myr | 3-OH-Tedc | 3-OOcto-Dco | 3-ODco-Dc | OH |
| 73 | 3-OH-Myr | 3-OH-Tedc | 3-ODco-Lau | 3-OLau-Ddc | OH |
| 74 | 3-OH-Myr | 3-OH-Tedc | 3-OLau-Myr | 3-OMyr-Tedc | OH |
| 75 | 3-OH-Myr | 3-OH-Tedc | 3-OH-Myr | 3-OMyr-Tedc | OH |
| 76 | 3-OH-Myr | 3-OH-Tedc | 3-OLau-Myr | 3-OH-Tedc | OH |
| 77 | 3-OH-Myr | 3-OH-Tedc | 3-OH-Myr | 3-OH-Tedc | OH |
| 78 | 3-OH-Myr | 3-OH-Tedc | 3-(=O)-Myr | 3-OH-Tedc | OH |
| 79 | 3-OH-Myr | 3-OH-Tedc | 3-OH-Myr | 3-(=O)-Tedc | OH |
| 80 | 3-OH-Myr | 3-OH-Tedc | 2-F-3-OLau-Myr | 2-F-3-OMyr-Tedc | OH |
| 81 | 3-OH-Myr | 3-OH-Tedc | 2-F-3-OH-Dco | 3-OMyr-Tedc | OH |
| 82 | 3-OH-Myr | 3-OH-Tedc | 2-Cl-3-OLau-Myr | 2-Cl-3-OMyr-Tedc | OH |
| 83 | 3-OH-Myr | 3-OH-Tedc | 3-OLau-Myr | 3-OMyr-Ddc | OH |
| 84 | 3-OH-Myr | 3-OH-Tedc | 3-OLau-Myr | 3-OMyr-Ddc | OH |
| 85 | 3-OH-Myr | 3-OH-Tedc | 3-OLau-Lau | 3-OMyr-Tedc | OH |
| 86 | 3-OH-Myr | 3-OH-Tedc | 3-OMyr-Pal | 3-OPal-Hdc | OH |
| 87 | 3-OH-Myr | 3-OH-Tedc | 3-OPal-Ste | 3-OSte-Odc | OH |
| 88 | 3-OH-Myr | 3-OH-Tedc | 3-OSte-Eicn | 3-OEicn-Ei | OH |
| 89 | 3-OH-Myr | 3-OH-Tedc | Fo | 3-OH-Ddc | OMe |
| 90 | 3-OH-Myr | 3-OH-Tedc | Ac | 3-OH-Ddc | OMe |
| 91 | 3-OH-Myr | 3-OH-Tedc | Prn | 3-OH-Ddc | OMe |
| 92 | 3-OH-Myr | 3-OH-Tedc | Byr | 3-OH-Ddc | OMe |
| 93 | 3-OH-Myr | 3-OH-Tedc | Val | 3-OH-Ddc | OMe |
| 94 | 3-OH-Myr | 3-OH-Tedc | Hxn | 3-OH-Ddc | OMe |
| 95 | 3-OH-Myr | 3-OH-Tedc | Octo | 3-OH-Tedc | OMe |
| 96 | 3-OH-Myr | 3-OH-Tedc | Fo | 3-OH-Tedc | OMe |
| 97 | 3-OH-Myr | 3-OH-Tedc | Ac | 3-OH-Tedc | OMe |
| 98 | 3-OH-Myr | 3-OH-Tedc | Prn | 3-OH-Tedc | OMe |
| 99 | 3-OH-Myr | 3-OH-Tedc | Byr | 3-OH-Tedc | OMe |
| 100 | 3-OH-Myr | 3-OH-Tedc | Val | 3-OH-Tedc | OMe |
| 101 | 3-OH-Myr | 3-OH-Tedc | Hxn | 3-OH-Tedc | OMe |
| 102 | 3-OH-Myr | 3-OH-Tedc | Fo | 3-OLau-Tedc | OMe |
| 103 | 3-OH-Myr | 3-OH-Tedc | Ac | 3-OLau-Tedc | OMe |
| 104 | 3-OH-Myr | 3-OH-Tedc | Prn | 3-OLau-Tedc | OMe |
| 105 | 3-OH-Myr | 3-OH-Tedc | Byr | 3-OLau-Tedc | OMe |
| 106 | 3-OH-Myr | 3-OH-Tedc | Val | 3-OLau-Tedc | OMe |
| 107 | 3-OH-Myr | 3-OH-Tedc | Hxn | 3-OLau-Tedc | OMe |
| 108 | 3-OH-Myr | 3-OH-Tedc | Fo | 3-OMyr-Ddc | OMe |
| 109 | 3-OH-Myr | 3-OH-Tedc | Ac | 3-OMyr-Ddc | OMe |
| 110 | 3-OH-Myr | 3-OH-Tedc | Prn | 3-OMyr-Ddc | OMe |
| 111 | 3-OH-Myr | 3-OH-Tedc | Byr | 3-OMyr-Ddc | OMe |
| 112 | 3-OH-Myr | 3-OH-Tedc | Val | 3-OMyr-Ddc | OMe |
| 113 | 3-OH-Myr | 3-OH-Tedc | Hxn | 3-OMyr-Ddc | OMe |

TABLE 1-continued

| compound No | R¹ | R² | R³ | R⁴ | R⁵ |
|---|---|---|---|---|---|
| 114 | 3-OH-Myr | 3-OH-Tedc | Fo | 3-OH-Ddc | OH |
| 115 | 3-OH-Myr | 3-OH-Tedc | Ac | 3-OH-Ddc | OH |
| 116 | 3-OH-Myr | 3-OH-Tedc | Prn | 3-OH-Ddc | OH |
| 117 | 3-OH-Myr | 3-OH-Tedc | Byr | 3-OH-Ddc | OH |
| 118 | 3-OH-Myr | 3-OH-Tedc | Val | 3-OH-Ddc | OH |
| 119 | 3-OH-Myr | 3-OH-Tedc | Hxn | 3-OH-Ddc | OH |
| 120 | 3-OH-Myr | 3-OH-Tedc | Fo | 3-OH-Tedc | OH |
| 121 | 3-OH-Myr | 3-OH-Tedc | Ac | 3-OH-Tedc | OH |
| 122 | 3-OH-Myr | 3-OH-Tedc | Prn | 3-OH-Tedc | OH |
| 123 | 3-OH-Myr | 3-OH-Tedc | Byr | 3-OH-Tedc | OH |
| 124 | 3-OH-Myr | 3-OH-Tedc | Val | 3-OH-Tedc | OH |
| 125 | 3-OH-Myr | 3-OH-Tedc | Hxn | 3-OH-Tedc | OH |
| 126 | 3-OH-Myr | 3-OH-Tedc | Fo | 3-OLau-Tedc | OH |
| 127 | 3-OH-Myr | 3-OH-Tedc | Ac | 3-OLau-Tedc | OH |
| 128 | 3-OH-Myr | 3-OH-Tedc | Prn | 3-OLau-Tedc | OH |
| 129 | 3-OH-Myr | 3-OH-Tedc | Byr | 3-OLau-Tedc | OH |
| 130 | 3-OH-Myr | 3-OH-Tedc | Val | 3-OLau-Tedc | OH |
| 131 | 3-OH-Myr | 3-OH-Tedc | Hxn | 3-OLau-Tedc | OH |
| 132 | 3-OH-Myr | 3-OH-Tedc | Fo | 3-OMyr-Ddc | OH |
| 133 | 3-OH-Myr | 3-OH-Tedc | Ac | 3-OMyr-Ddc | OH |
| 134 | 3-OH-Myr | 3-OH-Tedc | Prn | 3-OMyr-Ddc | OH |
| 135 | 3-OH-Myr | 3-OH-Tedc | Byr | 3-OMyr-Ddc | OH |
| 136 | 3-OH-Myr | 3-OH-Tedc | Val | 3-OMyr-Ddc | OH |
| 137 | 3-OH-Myr | 3-OH-Tedc | Hxn | 3-OMyr-Ddc | OH |
| 138 | 3-OH-Lau | 3-OH-Ddc | Fo | 3-OMyr-Tedc | F |
| 139 | 3-OH-Lau | 3-OH-Ddc | Ac | 3-OMyr-Tedc | F |
| 140 | 3-OH-Lau | 3-OH-Ddc | Prn | 3-OMyr-Tedc | F |
| 141 | 3-OH-Lau | 3-OH-Ddc | Byr | 3-OMyr-Tedc | F |
| 142 | 3-OH-Lau | 3-OH-Ddc | Hxn | 3-OMyr-Tedc | F |
| 143 | 3-OH-Lau | 3-OH-Ddc | Octo | 3-OMyr-Tedc | F |
| 144 | Myr | Tedc | Fo | 3-OMyr-Tedc | F |
| 145 | Myr | Tedc | Ac | 3-OMyr-Tedc | F |
| 146 | Myr | Tedc | Prn | 3-OMyr-Tedc | F |
| 147 | Myr | Tedc | Byr | 3-OMyr-Tedc | F |
| 148 | Myr | Tedc | Hxn | 3-OMyr-Tedc | F |
| 149 | 3-OH-Myr | 3-OH-Tedc | Fo | 3-OMyr-Tedc | F |
| 150 | 3-OH-Myr | 3-OH-Tedc | Ac | 3-OMyr-Tedc | F |
| 151 | 3-OH-Myr | 3-OH-Tedc | Prn | 3-OMyr-Tedc | F |
| 152 | 3-OH-Myr | 3-OH-Tedc | Byr | 3-OMyr-Tedc | F |
| 153 | 3-OH-Myr | 3-OH-Tedc | Val | 3-OMyr-Tedc | F |
| 154 | 3-OH-Myr | 3-OH-Tedc | Hxn | 3-OMyr-Tedc | F |
| 155 | 3-OH-Myr | 3-OH-Tedc | Octo | 3-OMyr-Tedc | F |
| 156 | 3-OH-Myr | 3-OH-Tedc | Dco | 3-OMyr-Tedc | F |
| 157 | 3-OH-Myr | 3-OH-Tedc | Lau | 3-OMyr-Tedc | F |
| 158 | 3-OH-Myr | 3-OH-Tedc | Myr | 3-OMyr-Tedc | F |
| 159 | 3-OH-Myr | 3-OH-Tedc | Pal | 3-OMyr-Tedc | F |
| 160 | 3-OH-Myr | 3-OH-Tedc | Ste | 3-OMyr-Tedc | F |
| 161 | 3-OH-Myr | 3-OH-Tedc | Eicn | 3-OMyr-Tedc | F |
| 162 | 3-OH-Myr | 3-OH-Tedc | 3-OAc-Byr | 3-OByr-Bu | F |
| 163 | 3-OH-Myr | 3-OH-Tedc | 3-OByr-Hxn | 3-OHxn-Hx | F |
| 164 | 3-OH-Myr | 3-OH-Tedc | 3-OHxn-Octo | 3-OOcto-Oc | F |
| 165 | 3-OH-Myr | 3-OH-Tedc | 3-OOcto-Dco | 3-ODco-Dc | F |
| 166 | 3-OH-Myr | 3-OH-Tedc | 3-ODco-Lau | 3-OLau-Ddc | F |
| 167 | 3-OH-Myr | 3-OH-Tedc | 3-OLau-Myr | 3-OMyr-Tedc | F |
| 168 | 3-OH-Myr | 3-OH-Tedc | 3-OH-Myr | 3-OMyr-Tedc | F |
| 169 | 3-OH-Myr | 3-OH-Tedc | 3-OLau-Myr | 3-OH-Tedc | F |
| 170 | 3-OH-Myr | 3-OH-Tedc | 3-OH-Myr | 3-OH-Tedc | F |
| 171 | 3-OH-Myr | 3-OH-Tedc | 3-(=O)-Myr | 3-OH-Tedc | F |
| 172 | 3-OH-Myr | 3-OH-Tedc | 3-OH-Myr | 3-(=O)-Tedc | F |
| 173 | 3-OH-Myr | 3-OH-Tedc | 2-F-3-OLau-Myr | 2-F-3-OMyr-Tedc | F |
| 174 | 3-OH-Myr | 3-OH-Tedc | 2-F-3-OH-Dco | 3-OMyr-Tedc | F |
| 175 | 3-OH-Myr | 3-OH-Tedc | 2-Cl-3-OLau-Myr | 2-Cl-3-OMyr-Tedc | F |

TABLE 1-continued

| compound No | R¹ | R² | R³ | R⁴ | R⁵ |
|---|---|---|---|---|---|
| 176 | 3-OH-Myr | 3-OH-Tedc | 3-OLau-Myr | 3-OMyr-Ddc | F |
| 178 | 3-OH-Myr | 3-OH-Tedc | 3-OLau-Lau | 3-OMyr-Tedc | F |
| 179 | 3-OH-Myr | 3-OH-Tedc | 3-OMyr-Pal | 3-OPal-Hdc | F |
| 180 | 3-OH-Myr | 3-OH-Tedc | 3-OPal-Ste | 3-OSte-Odc | F |
| 181 | 3-OH-Myr | 3-OH-Tedc | 3-OSte-Eicn | 3-OEicn-Ei | F |
| 182 | 3-OH-Lau | 3-OH-Ddc | Fo | 3-OMyr-Tedc | H |
| 183 | 3-OH-Lau | 3-OH-Ddc | Ac | 3-OMyr-Tedc | H |
| 184 | 3-OH-Lau | 3-OH-Ddc | Prn | 3-OMyr-Tedc | H |
| 185 | 3-OH-Lau | 3-OH-Ddc | Byr | 3-OMyr-Tedc | H |
| 186 | 3-OH-Lau | 3-OH-Ddc | Hxn | 3-OMyr-Tedc | H |
| 187 | 3-OH-Lau | 3-OH-Ddc | Octo | 3-OMyr-Tedc | H |
| 188 | Myr | Tedc | Fo | 3-OMyr-Tedc | H |
| 189 | Myr | Tedc | Ac | 3-OMyr-Tedc | H |
| 190 | Myr | Tedc | Prn | 3-OMyr-Tedc | H |
| 191 | Myr | Tedc | Byr | 3-OMyr-Tedc | H |
| 192 | Myr | Tedc | Hxn | 3-OMyr-Tedc | H |
| 193 | 3-OH-Myr | 3-OH-Tedc | Fo | 3-OMyr-Tedc | H |
| 194 | 3-OH-Myr | 3-OH-Tedc | Ac | 3-OMyr-Tedc | H |
| 195 | 3-OH-Myr | 3-OH-Tedc | Prn | 3-OMyr-Tedc | H |
| 196 | 3-OH-Myr | 3-OH-Tedc | Byr | 3-OMyr-Tedc | H |
| 197 | 3-OH-Myr | 3-OH-Tedc | Val | 3-OMyr-Tedc | H |
| 198 | 3-OH-Myr | 3-OH-Tedc | Hxn | 3-OMyr-Tedc | H |
| 199 | 3-OH-Myr | 3-OH-Tedc | Octo | 3-OMyr-Tedc | H |
| 200 | 3-OH-Myr | 3-OH-Tedc | Dco | 3-OMyr-Tedc | H |
| 201 | 3-OH-Myr | 3-OH-Tedc | Lau | 3-OMyr-Tedc | H |
| 202 | 3-OH-Myr | 3-OH-Tedc | Myr | 3-OMyr-Tedc | H |
| 203 | 3-OH-Myr | 3-OH-Tedc | Pal | 3-OMyr-Tedc | H |
| 204 | 3-OH-Myr | 3-OH-Tedc | Ste | 3-OMyr-Tedc | H |
| 205 | 3-OH-Myr | 3-OH-Tedc | Eicn | 3-OMyr-Tedc | H |
| 206 | 3-OH-Myr | 3-OH-Tedc | 3-OAc-Byr | 3-OByr-Bu | H |
| 207 | 3-OH-Myr | 3-OH-Tedc | 3-OByr-Hxn | 3-OHxn-Hx | H |
| 208 | 3-OH-Myr | 3-OH-Tedc | 3-OHxn-Octo | 3-OOcto-Oc | H |
| 209 | 3-OH-Myr | 3-OH-Tedc | 3-OOcto-Dco | 3-ODco-Dc | H |
| 210 | 3-OH-Myr | 3-OH-Tedc | 3-ODco-Lau | 3-OLau-Ddc | H |
| 211 | 3-OH-Myr | 3-OH-Tedc | 3-OLau-Myr | 3-OMyr-Tedc | H |
| 212 | 3-OH-Myr | 3-OH-Tedc | 3-OH-Myr | 3-OMyr-Tedc | H |
| 213 | 3-OH-Myr | 3-OH-Tedc | 3-OLau-Myr | 3-OH-Tedc | H |
| 214 | 3-OH-Myr | 3-OH-Tedc | 3-OH-Myr | 3-OH-Tedc | H |
| 215 | 3-OH-Myr | 3-OH-Tedc | 3-(=O)-Myr | 3-OH-Tedc | H |
| 216 | 3-OH-Myr | 3-OH-Tedc | 3-OH-Myr | 3-(=O)-Tedc | H |
| 217 | 3-OH-Myr | 3-OH-Tedc | 2-F-3-OLau-Myr | 2-F-3-OMyr-Tedc | H |
| 218 | 3-OH-Myr | 3-OH-Tedc | 2-F-3-OH-Dco | 3-OMyr-Tedc | H |
| 219 | 3-OH-Myr | 3-OH-Tedc | 2-Cl-3-OLau-Myr | 2-Cl-3-OMyr-Tedc | H |
| 220 | 3-OH-Myr | 3-OH-Tedc | 3-OLau-Myr | 3-OMyr-Ddc | H |
| 221 | 3-OH-Myr | 3-OH-Tedc | 3-OLau-Myr | 3-OMyr-Ddc | H |
| 222 | 3-OH-Myr | 3-OH-Tedc | 3-OLau-Lau | 3-OMyr-Tedc | H |
| 223 | 3-OH-Myr | 3-OH-Tedc | 3-OMyr-Pal | 3-OPal-Hdc | H |
| 224 | 3-OH-Myr | 3-OH-Tedc | 3-OPal-Ste | 3-OSte-Odc | H |
| 225 | 3-OH-Myr | 3-OH-Tedc | 3-OSte-Eicn | 3-OEicn-Ei | H |
| 226 | 3-OH-Myr | 3-OH-Tedc | Fo | 3-OH-Ddc | H |
| 227 | 3-OH-Myr | 3-OH-Tedc | Ac | 3-OH-Ddc | H |
| 228 | 3-OH-Myr | 3-OH-Tedc | Prn | 3-OH-Ddc | H |
| 229 | 3-OH-Myr | 3-OH-Tedc | Byr | 3-OH-Ddc | H |
| 230 | 3-OH-Myr | 3-OH-Tedc | Val | 3-OH-Ddc | H |
| 231 | 3-OH-Myr | 3-OH-Tedc | Hxn | 3-OH-Ddc | H |
| 232 | 3-OH-Myr | 3-OH-Tedc | Octo | 3-OH-Tedc | H |
| 233 | 3-OH-Myr | 3-OH-Tedc | Fo | 3-OH-Tedc | H |
| 234 | 3-OH-Myr | 3-OH-Tedc | Ac | 3-OH-Tedc | H |
| 235 | 3-OH-Myr | 3-OH-Tedc | Prn | 3-OH-Tedc | H |
| 236 | 3-OH-Myr | 3-OH-Tedc | Byr | 3-OH-Tedc | H |
| 237 | 3-OH-Myr | 3-OH-Tedc | Val | 3-OH-Tedc | H |
| 238 | 3-OH-Myr | 3-OH-Tedc | Hxn | 3-OH-Tedc | H |

TABLE 1-continued

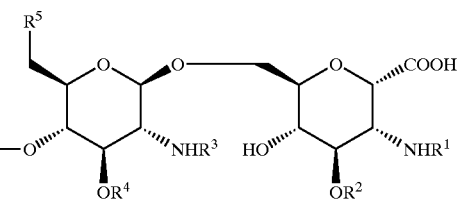

| compound No | R¹ | R² | R³ | R⁴ | R⁵ |
|---|---|---|---|---|---|
| 239 | 3-OH-Myr | 3-OH-Tedc | Fo | 3-OLau-Tedc | H |
| 240 | 3-OH-Myr | 3-OH-Tedc | Ac | 3-OLau-Tedc | H |
| 241 | 3-OH-Myr | 3-OH-Tedc | Prn | 3-OLau-Tedc | H |
| 242 | 3-OH-Myr | 3-OH-Tedc | Byr | 3-OLau-Tedc | H |
| 243 | 3-OH-Myr | 3-OH-Tedc | Val | 3-OLau-Tedc | H |
| 244 | 3-OH-Myr | 3-OH-Tedc | Hxn | 3-OLau-Tedc | H |
| 245 | 3-OH-Myr | 3-OH-Tedc | Fo | 3-OMyr-Ddc | H |
| 246 | 3-OH-Myr | 3-OH-Tedc | Ac | 3-OMyr-Ddc | H |
| 247 | 3-OH-Myr | 3-OH-Tedc | Prn | 3-OMyr-Ddc | H |
| 248 | 3-OH-Myr | 3-OH-Tedc | Byr | 3-OMyr-Ddc | H |
| 249 | 3-OH-Myr | 3-OH-Tedc | Val | 3-OMyr-Ddc | H |
| 250 | 3-OH-Myr | 3-OH-Tedc | Hxn | 3-OMyr-Ddc | H |
| 251 | 3-OH-Myr | 3-OH-Tedc | Fo | 3-OH-Ddc | H |
| 252 | 3-OH-Myr | 3-OH-Tedc | Ac | 3-OH-Ddc | H |
| 253 | 3-OH-Myr | 3-OH-Tedc | Prn | 3-OH-Ddc | H |
| 254 | 3-OH-Myr | 3-OH-Tedc | Byr | 3-OH-Ddc | H |
| 255 | 3-OH-Myr | 3-OH-Tedc | Val | 3-OH-Ddc | H |
| 256 | 3-OH-Myr | 3-OH-Tedc | Hxn | 3-OH-Ddc | H |
| 257 | 3-OH-Myr | 3-OH-Tedc | Fo | 3-OH-Tedc | H |
| 258 | 3-OH-Myr | 3-OH-Tedc | Ac | 3-OH-Tedc | H |
| 259 | 3-OH-Myr | 3-OH-Tedc | Prn | 3-OH-Tedc | H |
| 260 | 3-OH-Myr | 3-OH-Tedc | Byr | 3-OH-Tedc | H |
| 261 | 3-OH-Myr | 3-OH-Tedc | Val | 3-OH-Tedc | H |
| 262 | 3-OH-Myr | 3-OH-Tedc | Hxn | 3-OH-Tedc | H |
| 263 | 3-OH-Myr | 3-OH-Tedc | Fo | 3-OLau-Ddc | H |
| 264 | 3-OH-Myr | 3-OH-Tedc | Ac | 3-OLau-Ddc | H |
| 265 | 3-OH-Myr | 3-OH-Tedc | Prn | 3-OLau-Ddc | H |
| 266 | 3-OH-Myr | 3-OH-Tedc | Byr | 3-OLau-Ddc | H |
| 267 | 3-OH-Myr | 3-OH-Tedc | Val | 3-OLau-Ddc | H |
| 268 | 3-OH-Myr | 3-OH-Tedc | Hxn | 3-OLau-Ddc | H |
| 269 | 3-OH-Myr | 3-OH-Tedc | Fo | 3-OMyr-Hdc | H |
| 270 | 3-OH-Myr | 3-OH-Tedc | Ac | 3-OMyr-Hdc | H |
| 271 | 3-OH-Myr | 3-OH-Tedc | Prn | 3-OMyr-Hdc | H |
| 272 | 3-OH-Myr | 3-OH-Tedc | Byr | 3-OMyr-Hdc | H |
| 273 | 3-OH-Myr | 3-OH-Tedc | Val | 3-OMyr-Hdc | H |
| 274 | 3-OH-Myr | 3-OH-Tedc | Hxn | 3-OMyr-Hdc | H |
| 275 | 3-OH-Lau | 3-OH-Ddc | Fo | 3-ODdc-Tedc | OMe |
| 276 | 3-OH-Lau | 3-OH-Ddc | Ac | 3-ODdc-Tedc | OMe |
| 277 | 3-OH-Lau | 3-OH-Ddc | Prn | 3-ODdc-Tedc | OMe |
| 278 | 3-OH-Lau | 3-OH-Ddc | Byr | 3-ODdc-Tedc | OMe |
| 279 | 3-OH-Lau | 3-OH-Ddc | Hxn | 3-ODdc-Tedc | OMe |
| 280 | 3-OH-Lau | 3-OH-Ddc | Octo | 3-ODdc-Tedc | OMe |
| 281 | Myr | Tedc | Fo | 3-ODdc-Tedc | OMe |
| 282 | Myr | Tedc | Ac | 3-ODdc-Tedc | OMe |
| 283 | Myr | Tedc | Prn | 3-ODdc-Tedc | OMe |
| 284 | Myr | Tedc | Byr | 3-ODdc-Tedc | OMe |
| 285 | Myr | Tedc | Hxn | 3-ODdc-Tedc | OMe |
| 286 | 3-OH-Myr | 3-OH-Tedc | Fo | 3-ODdc-Tedc | OMe |
| 287 | 3-OH-Myr | 3-OH-Tedc | Ac | 3-ODdc-Tedc | OMe |
| 288 | 3-OH-Myr | 3-OH-Tedc | Prn | 3-ODdc-Tedc | OMe |
| 289 | 3-OH-Myr | 3-OH-Tedc | Byr | 3-ODdc-Tedc | OMe |
| 290 | 3-OH-Myr | 3-OH-Tedc | Val | 3-ODdc-Tedc | OMe |
| 291 | 3-OH-Myr | 3-OH-Tedc | Hxn | 3-ODdc-Tedc | OMe |
| 292 | 3-OH-Myr | 3-OH-Tedc | Octo | 3-ODdc-Tedc | OMe |
| 293 | 3-OH-Myr | 3-OH-Tedc | Dco | 3-ODdc-Tedc | OMe |
| 294 | 3-OH-Myr | 3-OH-Tedc | Lau | 3-ODdc-Tedc | OMe |
| 295 | 3-OH-Myr | 3-OH-Tedc | Myr | 3-ODdc-Tedc | OMe |
| 296 | 3-OH-Myr | 3-OH-Tedc | Pal | 3-ODdc-Tedc | OMe |
| 297 | 3-OH-Myr | 3-OH-Tedc | Ste | 3-ODdc-Tedc | OMe |
| 298 | 3-OH-Myr | 3-OH-Tedc | Eicn | 3-ODdc-Tedc | OMe |
| 299 | 3-OH-Myr | 3-OH-Tedc | 3-OAc-Byr | 3-OBu-Bu | OMe |
| 300 | 3-OH-Myr | 3-OH-Tedc | 3-OByr-Hxn | 3-OHx-Hx | OMe |
| 301 | 3-OH-Myr | 3-OH-Tedc | 3-OHxn-Octo | 3-OOc-Oc | OMe |
| 302 | 3-OH-Myr | 3-OH-Tedc | 3-OOcto-Dco | 3-ODc-Dc | OMe |
| 303 | 3-OH-Myr | 3-OH-Tedc | 3-ODco-Lau | 3-ODdc-Ddc | OMe |

TABLE 1-continued

[Structure: disaccharide with R⁵ group, (HO)₂P(O)O- phosphate, OR⁴, NHR³ on left sugar; COOH, OH, OR², NHR¹ on right sugar]

| compound No | R¹ | R² | R³ | R⁴ | R⁵ |
|---|---|---|---|---|---|
| 304 | 3-OH-Myr | 3-OH-Tedc | 3-OLau-Myr | 3-ODdc-Tedc | OMe |
| 305 | 3-OH-Myr | 3-OH-Tedc | 3-OH-Myr | 3-ODdc-Tedc | OMe |
| 306 | 3-OH-Myr | 3-OH-Tedc | 2-F-3-OLau-Myr | 2-F-3-ODdc-Tedc | OMe |
| 307 | 3-OH-Myr | 3-OH-Tedc | 2-F-3-OH-Dco | 3-ODdc-Tedc | OMe |
| 308 | 3-OH-Myr | 3-OH-Tedc | 2-Cl-3-OLau-Myr | 2-Cl-3-ODdc-Tedc | OMe |
| 309 | 3-OH-Myr | 3-OH-Tedc | 3-OLau-Myr | 3-OTedc-Ddc | OMe |
| 311 | 3-OH-Myr | 3-OH-Tedc | 3-OLau-Lau | 3-ODdc-Tedc | OMe |
| 312 | 3-OH-Myr | 3-OH-Tedc | 3-OMyr-Pal | 3-OHdc-Hdc | OMe |
| 313 | 3-OH-Myr | 3-OH-Tedc | 3-OPal-Ste | 3-OOdc-Odc | OMe |
| 314 | 3-OH-Myr | 3-OH-Tedc | 3-OSte-Eicn | 3-OEi-Ei | OMe |
| 315 | 3-OH-Lau | 3-OH-Ddc | Fo | 3-ODdc-Tedc | OH |
| 316 | 3-OH-Lau | 3-OH-Ddc | Ac | 3-ODdc-Tedc | OH |
| 317 | 3-OH-Lau | 3-OH-Ddc | Prn | 3-ODdc-Tedc | OH |
| 318 | 3-OH-Lau | 3-OH-Ddc | Byr | 3-ODdc-Tedc | OH |
| 319 | 3-OH-Lau | 3-OH-Ddc | Hxn | 3-ODdc-Tedc | OH |
| 320 | 3-OH-Lau | 3-OH-Ddc | Octo | 3-ODdc-Tedc | OH |
| 321 | Myr | Tedc | Fo | 3-ODdc-Tedc | OH |
| 322 | Myr | Tedc | Ac | 3-ODdc-Tedc | OH |
| 323 | Myr | Tedc | Prn | 3-ODdc-Tedc | OH |
| 324 | Myr | Tedc | Byr | 3-ODdc-Tedc | OH |
| 325 | Myr | Tedc | Hxn | 3-ODdc-Tedc | OH |
| 326 | 3-OH-Myr | 3-OH-Tedc | Fo | 3-ODdc-Tedc | OH |
| 327 | 3-OH-Myr | 3-OH-Tedc | Ac | 3-ODdc-Tedc | OH |
| 328 | 3-OH-Myr | 3-OH-Tedc | Prn | 3-ODdc-Tedc | OH |
| 329 | 3-OH-Myr | 3-OH-Tedc | Byr | 3-ODdc-Tedc | OH |
| 330 | 3-OH-Myr | 3-OH-Tedc | Val | 3-ODdc-Tedc | OH |
| 331 | 3-OH-Myr | 3-OH-Tedc | Hxn | 3-ODdc-Tedc | OH |
| 332 | 3-OH-Myr | 3-OH-Tedc | Octo | 3-ODdc-Tedc | OH |
| 333 | 3-OH-Myr | 3-OH-Tedc | Dco | 3-ODdc-Tedc | OH |
| 334 | 3-OH-Myr | 3-OH-Tedc | Lau | 3-ODdc-Tedc | OH |
| 335 | 3-OH-Myr | 3-OH-Tedc | Myr | 3-ODdc-Tedc | OH |
| 336 | 3-OH-Myr | 3-OH-Tedc | Pal | 3-ODdc-Tedc | OH |
| 337 | 3-OH-Myr | 3-OH-Tedc | Ste | 3-ODdc-Tedc | OH |
| 338 | 3-OH-Myr | 3-OH-Tedc | Eicn | 3-ODdc-Tedc | OH |
| 339 | 3-OH-Myr | 3-OH-Tedc | 3-OAc-Byr | 3-OBu-Bu | OH |
| 340 | 3-OH-Myr | 3-OH-Tedc | 3-OByr-Hxn | 3-OHx-Hx | OH |
| 341 | 3-OH-Myr | 3-OH-Tedc | 3-OHxn-Octo | 3-OOc-Oc | OH |
| 342 | 3-OH-Myr | 3-OH-Tedc | 3-OOcto-Dco | 3-ODc-Dc | OH |
| 343 | 3-OH-Myr | 3-OH-Tedc | 3-ODco-Lau | 3-ODdc-Ddc | OH |
| 344 | 3-OH-Myr | 3-OH-Tedc | 3-OLau-Myr | 3-ODdc-Tedc | OH |
| 345 | 3-OH-Myr | 3-OH-Tedc | 3-OH-Myr | 3-ODdc-Tedc | OH |
| 346 | 3-OH-Myr | 3-OH-Tedc | 2-F-3-OLau-Myr | 2-F-3-ODdc-Tedc | OH |
| 347 | 3-OH-Myr | 3-OH-Tedc | 2-F-3-OH-Dco | 3-ODdc-Tedc | OH |
| 348 | 3-OH-Myr | 3-OH-Tedc | 2-Cl-3-OLau-Myr | 2-Cl-3-ODdc-Tedc | OH |
| 349 | 3-OH-Myr | 3-OH-Tedc | 3-OLau-Myr | 3-OTedc-Ddc | OH |
| 351 | 3-OH-Myr | 3-OH-Tedc | 3-OLau-Lau | 3-ODdc-Tedc | OH |
| 352 | 3-OH-Myr | 3-OH-Tedc | 3-OMyr-Pal | 3-OHdc-Hdc | OH |
| 353 | 3-OH-Myr | 3-OH-Tedc | 3-OPal-Ste | 3-OOdc-Odc | OH |
| 354 | 3-OH-Myr | 3-OH-Tedc | 3-OSte-Eicn | 3-OEi-Ei | OH |
| 355 | 3-OH-Myr | 3-OH-Tedc | Fo | 3-OTedc-Tedc | OMe |
| 356 | 3-OH-Myr | 3-OH-Tedc | Ac | 3-OTedc-Tedc | OMe |
| 357 | 3-OH-Myr | 3-OH-Tedc | Prn | 3-OTedc-Tedc | OMe |
| 358 | 3-OH-Myr | 3-OH-Tedc | Byr | 3-OTedc-Tedc | OMe |
| 359 | 3-OH-Myr | 3-OH-Tedc | Val | 3-OTedc-Tedc | OMe |
| 360 | 3-OH-Myr | 3-OH-Tedc | Hxn | 3-OTedc-Tedc | OMe |
| 361 | 3-OH-Myr | 3-OH-Tedc | Fo | 3-OTedc-Ddc | OMe |
| 362 | 3-OH-Myr | 3-OH-Tedc | Ac | 3-OTedc-Ddc | OMe |
| 363 | 3-OH-Myr | 3-OH-Tedc | Prn | 3-OTedc-Ddc | OMe |
| 364 | 3-OH-Myr | 3-OH-Tedc | Byr | 3-OTedc-Ddc | OMe |
| 365 | 3-OH-Myr | 3-OH-Tedc | Val | 3-OTedc-Ddc | OMe |

TABLE 1-continued

| compound No | R¹ | R² | R³ | R⁴ | R⁵ |
|---|---|---|---|---|---|
| 366 | 3-OH-Myr | 3-OH-Tedc | Hxn | 3-OTedc-Ddc | OMe |
| 367 | 3-OH-Myr | 3-OH-Tedc | Fo | 3-OTedc-Tedc | OH |
| 368 | 3-OH-Myr | 3-OH-Tedc | Ac | 3-OTedc-Tedc | OH |
| 369 | 3-OH-Myr | 3-OH-Tedc | Prn | 3-OTedc-Tedc | OH |
| 370 | 3-OH-Myr | 3-OH-Tedc | Byr | 3-OTedc-Tedc | OH |
| 371 | 3-OH-Myr | 3-OH-Tedc | Val | 3-OTedc-Tedc | OH |
| 372 | 3-OH-Myr | 3-OH-Tedc | Hxn | 3-OTedc-Tedc | OH |
| 373 | 3-OH-Myr | 3-OH-Tedc | Fo | 3-OTedc-Ddc | OH |
| 374 | 3-OH-Myr | 3-OH-Tedc | Ac | 3-OTedc-Ddc | OH |
| 375 | 3-OH-Myr | 3-OH-Tedc | Prn | 3-OTedc-Ddc | OH |
| 376 | 3-OH-Myr | 3-OH-Tedc | Byr | 3-OTedc-Ddc | OH |
| 377 | 3-OH-Myr | 3-OH-Tedc | Val | 3-OTedc-Ddc | OH |
| 378 | 3-OH-Myr | 3-OH-Tedc | Hxn | 3-OTedc-Ddc | OH |
| 379 | 3-OH-Lau | 3-OH-Ddc | Fo | 3-OTedc-Tedc | F |
| 380 | 3-OH-Lau | 3-OH-Ddc | Ac | 3-OTedc-Tedc | F |
| 381 | 3-OH-Lau | 3-OH-Ddc | Prn | 3-OTedc-Tedc | F |
| 382 | 3-OH-Lau | 3-OH-Ddc | Byr | 3-OTedc-Tedc | F |
| 383 | 3-OH-Lau | 3-OH-Ddc | Hxn | 3-OTedc-Tedc | F |
| 384 | 3-OH-Lau | 3-OH-Ddc | Octo | 3-OTedc-Tedc | F |
| 385 | Myr | Tedc | Fo | 3-OTedc-Tedc | F |
| 386 | Myr | Tedc | Ac | 3-OTedc-Tedc | F |
| 387 | Myr | Tedc | Prn | 3-OTedc-Tedc | F |
| 388 | Myr | Tedc | Byr | 3-OTedc-Tedc | F |
| 389 | Myr | Tedc | Hxn | 3-OTedc-Tedc | F |
| 390 | 3-OH-Myr | 3-OH-Tedc | Fo | 3-ODdc-Tedc | F |
| 391 | 3-OH-Myr | 3-OH-Tedc | Ac | 3-ODdc-Tedc | F |
| 392 | 3-OH-Myr | 3-OH-Tedc | Prn | 3-ODdc-Tedc | F |
| 393 | 3-OH-Myr | 3-OH-Tedc | Byr | 3-ODdc-Tedc | F |
| 394 | 3-OH-Myr | 3-OH-Tedc | Val | 3-ODdc-Tedc | F |
| 395 | 3-OH-Myr | 3-OH-Tedc | Hxn | 3-ODdc-Tedc | F |
| 396 | 3-OH-Myr | 3-OH-Tedc | Octo | 3-ODdc-Tedc | F |
| 397 | 3-OH-Myr | 3-OH-Tedc | Dco | 3-ODdc-Tedc | F |
| 398 | 3-OH-Myr | 3-OH-Tedc | Lau | 3-ODdc-Tedc | F |
| 399 | 3-OH-Myr | 3-OH-Tedc | Myr | 3-ODdc-Tedc | F |
| 400 | 3-OH-Myr | 3-OH-Tedc | Pal | 3-ODdc-Tedc | F |
| 401 | 3-OH-Myr | 3-OH-Tedc | Ste | 3-ODdc-Tedc | F |
| 402 | 3-OH-Myr | 3-OH-Tedc | Eicn | 3-ODdc-Tedc | F |
| 403 | 3-OH-Myr | 3-OH-Tedc | 3-OAc-Byr | 3-OBu-Bu | F |
| 404 | 3-OH-Myr | 3-OH-Tedc | 3-OByr-Hxn | 3-OHx-Hx | F |
| 405 | 3-OH-Myr | 3-OH-Tedc | 3-OHxn-Octo | 3-OOc-Oc | F |
| 406 | 3-OH-Myr | 3-OH-Tedc | 3-OOcto-Dco | 3-ODc-Dc | F |
| 407 | 3-OH-Myr | 3-OH-Tedc | 3-ODco-Lau | 3-ODdc-Ddc | F |
| 408 | 3-OH-Myr | 3-OH-Tedc | 3-OLau-Myr | 3-ODdc-Tedc | F |
| 409 | 3-OH-Myr | 3-OH-Tedc | 3-OH-Myr | 3-ODdc-Tedc | F |
| 410 | 3-OH-Myr | 3-OH-Tedc | 2-F-3-OLau-Myr | 2-F-3-ODdc-Tedc | F |
| 411 | 3-OH-Myr | 3-OH-Tedc | 2-F-3-OH-Dco | 3-ODdc-Tedc | F |
| 412 | 3-OH-Myr | 3-OH-Tedc | 2-Cl-3-OLau-Myr | 2-Cl-3-ODdc-Tedc | F |
| 413 | 3-OH-Myr | 3-OH-Tedc | 3-OLau-Myr | 3-OTedc-Ddc | F |
| 414 | 3-OH-Myr | 3-OH-Tedc | 3-OLau-Myr | 3-OTedc-Ddc | F |
| 415 | 3-OH-Myr | 3-OH-Tedc | 3-OLau-Lau | 3-ODdc-Tedc | F |
| 416 | 3-OH-Myr | 3-OH-Tedc | 3-OMyr-Pal | 3-OHdc-Hdc | F |
| 417 | 3-OH-Myr | 3-OH-Tedc | 3-OPal-Ste | 3-OOdc-Odc | F |
| 418 | 3-OH-Myr | 3-OH-Tedc | 3-OSte-Eicn | 3-OEi-Ei | F |
| 419 | 3-OH-Lau | 3-OH-Ddc | Fo | 3-ODdc-Tedc | H |
| 420 | 3-OH-Lau | 3-OH-Ddc | Ac | 3-ODdc-Tedc | H |
| 421 | 3-OH-Lau | 3-OH-Ddc | Prn | 3-ODdc-Tedc | H |
| 422 | 3-OH-Lau | 3-OH-Ddc | Byr | 3-ODdc-Tedc | H |
| 423 | 3-OH-Lau | 3-OH-Ddc | Hxn | 3-ODdc-Tedc | H |
| 424 | 3-OH-Lau | 3-OH-Ddc | Octo | 3-ODdc-Tedc | H |
| 425 | Myr | Tedc | Fo | 3-ODdc-Tedc | H |
| 426 | Myr | Tedc | Ac | 3-ODdc-Tedc | H |
| 427 | Myr | Tedc | Prn | 3-ODdc-Tedc | H |

TABLE 1-continued

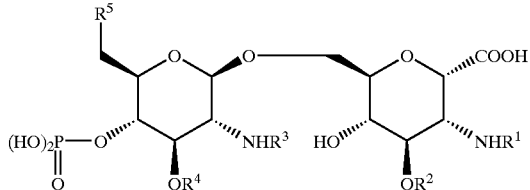

| compound No | R¹ | R² | R³ | R⁴ | R⁵ |
|---|---|---|---|---|---|
| 428 | Myr | Tedc | Byr | 3-ODdc-Tedc | H |
| 429 | Myr | Tedc | Hxn | 3-ODdc-Tedc | H |
| 430 | 3-OH-Myr | 3-OH-Tedc | Fo | 3-ODdc-Tedc | H |
| 431 | 3-OH-Myr | 3-OH-Tedc | Ac | 3-ODdc-Tedc | H |
| 432 | 3-OH-Myr | 3-OH-Tedc | Prn | 3-ODdc-Tedc | H |
| 433 | 3-OH-Myr | 3-OH-Tedc | Byr | 3-ODdc-Tedc | H |
| 434 | 3-OH-Myr | 3-OH-Tedc | Val | 3-ODdc-Tedc | H |
| 435 | 3-OH-Myr | 3-OH-Tedc | Hxn | 3-ODdc-Tedc | H |
| 436 | 3-OH-Myr | 3-OH-Tedc | Octo | 3-ODdc-Tedc | H |
| 437 | 3-OH-Myr | 3-OH-Tedc | Dco | 3-ODdc-Tedc | H |
| 438 | 3-OH-Myr | 3-OH-Tedc | Lau | 3-ODdc-Tedc | H |
| 439 | 3-OH-Myr | 3-OH-Tedc | Myr | 3-ODdc-Tedc | H |
| 440 | 3-OH-Myr | 3-OH-Tedc | Pal | 3-ODdc-Tedc | H |
| 441 | 3-OH-Myr | 3-OH-Tedc | Ste | 3-ODdc-Tedc | H |
| 442 | 3-OH-Myr | 3-OH-Tedc | Eicn | 3-ODdc-Tedc | H |
| 443 | 3-OH-Myr | 3-OH-Tedc | 3-OAc-Byr | 3-OBu-Bu | H |
| 444 | 3-OH-Myr | 3-OH-Tedc | 3-OByr-Hxn | 3-OHx-Hx | H |
| 445 | 3-OH-Myr | 3-OH-Tedc | 3-OHxn-Octo | 3-OOc-Oc | H |
| 446 | 3-OH-Myr | 3-OH-Tedc | 3-OOcto-Dco | 3-ODc-Dc | H |
| 447 | 3-OH-Myr | 3-OH-Tedc | 3-ODco-Lau | 3-ODdc-Ddc | H |
| 448 | 3-OH-Myr | 3-OH-Tedc | 3-OLau-Myr | 3-ODdc-Tedc | H |
| 449 | 3-OH-Myr | 3-OH-Tedc | 3-OH-Myr | 3-ODdc-Tedc | H |
| 450 | 3-OH-Myr | 3-OH-Tedc | 2-F-3-OLau-Myr | 2-F-3-ODdc-Tedc | H |
| 451 | 3-OH-Myr | 3-OH-Tedc | 2-F-3-OH-Dco | 3-ODdc-Tedc | H |
| 452 | 3-OH-Myr | 3-OH-Tedc | 2-Cl-3-OLau-Myr | 2-Cl-3-ODdc-Tedc | H |
| 453 | 3-OH-Myr | 3-OH-Tedc | 3-OLau-Myr | 3-OTedc-Ddc | H |
| 455 | 3-OH-Myr | 3-OH-Tedc | 3-OLau-Lau | 3-OTedc-Ddc | H |
| 456 | 3-OH-Myr | 3-OH-Tedc | 3-OMyr-Pal | 3-OHdc-Hdc | H |
| 457 | 3-OH-Myr | 3-OH-Tedc | 3-OPal-Ste | 3-OOdc-Odc | H |
| 458 | 3-OH-Myr | 3-OH-Tedc | 3-OSte-Eicn | 3-OEi-Ei | H |
| 459 | 3-OH-Myr | 3-OH-Tedc | Fo | 3-OTedc-Tedc | H |
| 460 | 3-OH-Myr | 3-OH-Tedc | Ac | 3-OTedc-Tedc | H |
| 461 | 3-OH-Myr | 3-OH-Tedc | Prn | 3-OTedc-Tedc | H |
| 462 | 3-OH-Myr | 3-OH-Tedc | Byr | 3-OTedc-Tedc | H |
| 463 | 3-OH-Myr | 3-OH-Tedc | Val | 3-OTedc-Tedc | H |
| 464 | 3-OH-Myr | 3-OH-Tedc | Hxn | 3-OTedc-Tedc | H |
| 465 | 3-OH-Myr | 3-OH-Tedc | Fo | 3-OTedc-Ddc | H |
| 466 | 3-OH-Myr | 3-OH-Tedc | Ac | 3-OTedc-Ddc | H |
| 467 | 3-OH-Myr | 3-OH-Tedc | Prn | 3-OTedc-Ddc | H |
| 468 | 3-OH-Myr | 3-OH-Tedc | Byr | 3-OTedc-Ddc | H |
| 469 | 3-OH-Myr | 3-OH-Tedc | Val | 3-OTedc-Ddc | H |
| 470 | 3-OH-Myr | 3-OH-Tedc | Hxn | 3-OTedc-Ddc | H |
| 471 | 3-OH-Myr | 3-OH-Tedc | Fo | 3-ODdc-Ddc | H |
| 472 | 3-OH-Myr | 3-OH-Tedc | Ac | 3-ODdc-Ddc | H |
| 473 | 3-OH-Myr | 3-OH-Tedc | Prn | 3-ODdc-Ddc | H |
| 474 | 3-OH-Myr | 3-OH-Tedc | Byr | 3-ODdc-Ddc | H |
| 475 | 3-OH-Myr | 3-OH-Tedc | Val | 3-ODdc-Ddc | H |
| 476 | 3-OH-Myr | 3-OH-Tedc | Hxn | 3-ODdc-Ddc | H |
| 477 | 3-OH-Myr | 3-OH-Tedc | Fo | 3-OTedc-Hdc | H |
| 478 | 3-OH-Myr | 3-OH-Tedc | Ac | 3-OTedc-Hdc | H |
| 479 | 3-OH-Myr | 3-OH-Tedc | Prn | 3-OTedc-Hdc | H |
| 480 | 3-OH-Myr | 3-OH-Tedc | Byr | 3-OTedc-Hdc | H |
| 481 | 3-OH-Myr | 3-OH-Tedc | Val | 3-OTedc-Hdc | H |
| 482 | 3-OH-Myr | 3-OH-Tedc | Hxn | 3-OTedc-Hdc | H |

The numbers of preferred compounds in the above table are 1, 2, 3, 7, 8, 9, 12, 13, 14, 45, 46, 47, 51, 52, 53, 56, 57, 58, 89, 90, 91, 96, 97, 98, 102, 103, 104, 108, 109, 110, 114, 115, 116, 120, 121, 122, 126, 127, 128, 132, 133, 134, 138, 139, 140, 144, 145, 146, 150, 182, 183, 184, 194, 234, 240, 252, 263, 264, 265, 276, 282, 287, 316, 322, 327, 380, 386, 391 and 431.

The numbers of more preferred compounds in the above table are 2, 3, 8, 9, 13, 14, 46, 47, 52, 53, 57, 58, 103, 104, 109, 110, 115, 121, 127, 128, 133, 134, 139, 145, 150, 183, 194, 264, 276, 287, 316, 327, 380, 391 and 431.

The most preferred compounds in the above table are:

2 (exemplification compound number in the table):
2,6-anhydro-7-O-[2-acetylamino-2-deoxy-6-O-methyl-4-O-phosphono-3-O-{(R)-3-tetradecanoyloxytetradecyl}-β-D-glucopyranosyl]-3-{(R)-3-hydroxydodecanoylamino}-4-O-{(R)-3-hydroxydodecyl}-3-deoxy-D-glycero-D-ido-heptonic acid;

8 (exemplification compound number in the table):
2,6-anhydro-7-O-[2-acetylamino-2-deoxy-6-O-methyl-4-O-phosphono-3-O-{(R)-3-tetradecanoyloxytetradecyl}-β-D-glucopyranosyl]-3-tetradecanoylamino-4-O-tetradecyl-3-deoxy-D-glycero-D-ido-heptonic acid;

13 (exemplification compound number in the table):
2,6-anhydro-7-O-[2-acetylamino-2-deoxy-6-O-methyl-4-O-phosphono-3-O-{(R)-3-tetradecanoyloxytetradecyl}-β-D-glucopyranosyl]-3-{(R)-3-hydroxytetradecanoylamino}-4-O-{(R)-3-hydroxytetradecyl}-3-deoxy-D-glycero-D-ido-heptonic acid;

46 (exemplification compound number in the table):
2,6-anhydro-7-O-[2-acetylamino-2-deoxy-4-O-phosphono-3-O-{(R)-3-tetradecanoyloxytetradecyl}-β-D-glucopyranosyl]-3-{(R)-3-hydroxydodecanoylamino}-4-O-{(R)-3-hydroxydodecyl}-3-deoxy-D-glycero-D-ido-heptonic acid;

52 (exemplification compound number in the table):
2,6-anhydro-7-O-[2-acetylamino-2-deoxy-4-O-phosphono-3-O-{(R)-3-tetradecanoyloxytetradecyl}-β-D-glucopyranosyl]-3-tetradecanoylamino-4-O-tetradecyl-3-deoxy-D-glycero-D-ido-heptonic acid;

57 (exemplification compound number in the table):
2,6-anhydro-7-O-[2-acetylamino-2-deoxy-4-O-phosphono-3-O-{(R)-3-tetradecanoyloxytetradecyl}-β-D-glucopyranosyl]-3-{(R)-3-hydroxytetradecanoylamino}-4-O-{(R)-3-hydroxytetradecyl}-3-deoxy-D-glycero-D-ido-heptonic acid;

121 (exemplification compound number in the table):
2,6-anhydro-7-O-[2-acetylamino-2-deoxy-4-O-phosphono-3-O-{(R)-3-hydroxytetradecyl}-β-D-glucopyranosyl]-3-{(R)-3-hydroxytetradecanoylamino}-4-O-{(R)-3-hydroxytetradecyl}-3-deoxy-D-glycero-D-ido-heptonic acid;

127 (exemplification compound number in the table):
2,6-anhydro-7-O-[2-acetylamino-2-deoxy-4-O-phosphono-3-O-{(R)-3-dodecanoyloxytetradecyl}-β-D-glucopyranosyl]-3-{(R)-3-hydroxytetradecanoylamino}-4-O-{(R)-3-hydroxytetradecyl}-3-deoxy-D-glycero-D-ido-heptonic acid;

139 (exemplification compound number in the table):
2,6-anhydro-7-O-[2-acetylamino-2,6-dideoxy-4-O-phosphono-6-fluoro-3-O-{(R)-3-tetradecanoyloxytetradecyl}-β-D-glucopyranosyl]-3-{(R)-3-hydroxydodecanoylamino}-4-O-{(R)-3-hydroxydodecyl}-3-deoxy-D-glycero-D-ido-heptonic acid;

150 (exemplification compound number in the table):
2,6-anhydro-7-O-[2-acetylamino-2,6-dideoxy-6-fluoro-4-O-phosphono-3-O-{(R)-3-tetradecanoyloxytetradecyl}-β-D-glucopyranosyl]-3-{(R)-3-hydroxytetradecanoylamino}-4-O-{(R)-3-hydroxytetradecyl}-3-deoxy-D-glycero-D-ido-heptonic acid;

287 (exemplification compound number in the table):
2,6-anhydro-7-O-[2-acetylamino-2-deoxy-3-O-{(R)-3-dodecyloxytetradecyl}-6-O-methyl-4-O-phosphono-β-D-glucopyranosyl]-3-{(R)-3-hydroxytetradecanoylamino}-4-O-{(R)-3-hydroxyteradecyl}-3-deoxy-D-glycero-D-ido-heptonic acid;

327 (exemplification compound number in the table):
2,6-anhydro-7-O-[2-acetylamino-2-deoxy-3-O-{(R)-3-dodecyloxytetradecyl}-4-O-phosphono-β-D-glucopyranosyl]-3-{(R)-3-hydroxytertradecanoylamino}-4-O-{(R)-3-hydroxytetradecyl}-3-deoxy-D-glycero-D-ido-heptonic acid; and 391 (exemplification compound number in the table):
2,6-anhydro-7-O-[2-acetylamino-2,6-dideoxy-3-O-{(R)-3-dodecyloxytetradecyl}-6-fluoro-4-O-phosphono-β-D-glucopyranosyl]-3-{(R)-3-hydroxytetradecanoylamino}-4-O-{(R)-3-hdroxytetradecyl}-3-deoxy-D-glycero-D-ido-heptonic acid.

The compound (I) of the present invention can be produced by methods illustrated below using known compounds (II) and (XI) (Carbohydrate Research 222, 57 (1991) as starting materials.

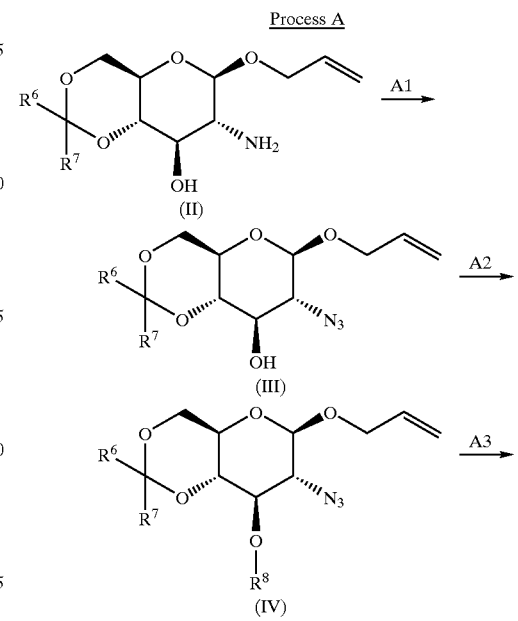

-continued
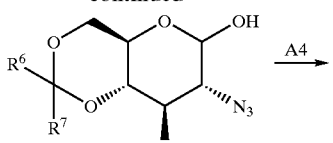
(V)
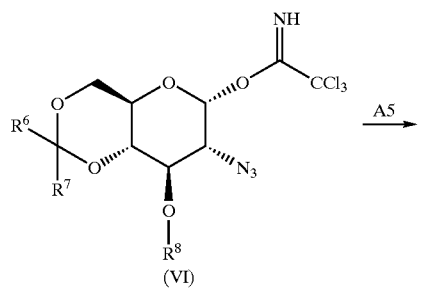
(VI)
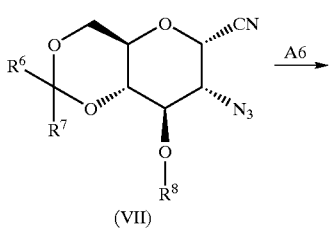
(VII)
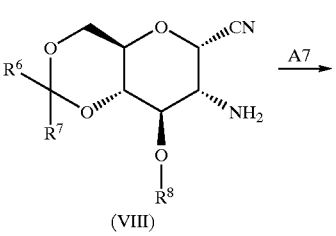
(VIII)
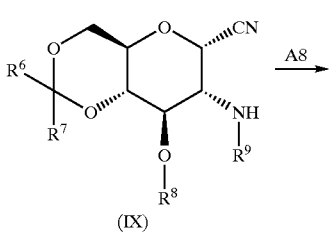
(IX)
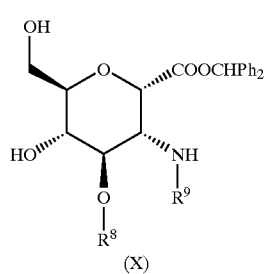
(X)
Process B
Method a
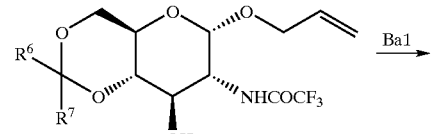
(XI)
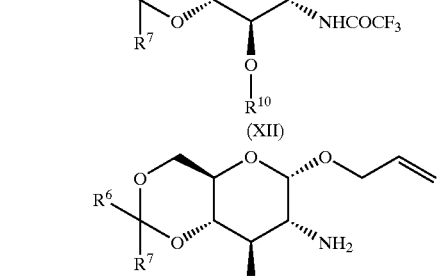
(XII)
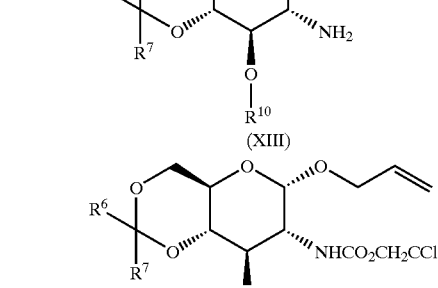
(XIII)
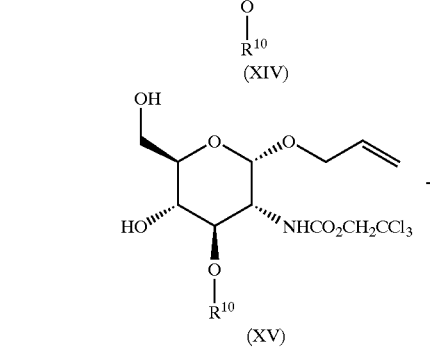
(XIV)
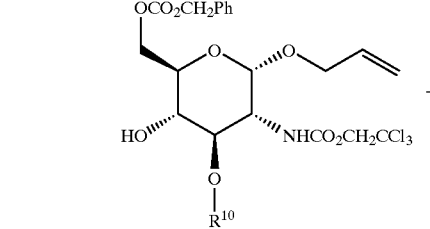
(XV)
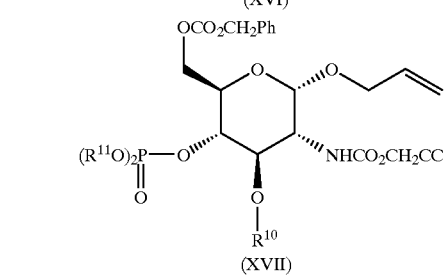
(XVI)
(XVII)

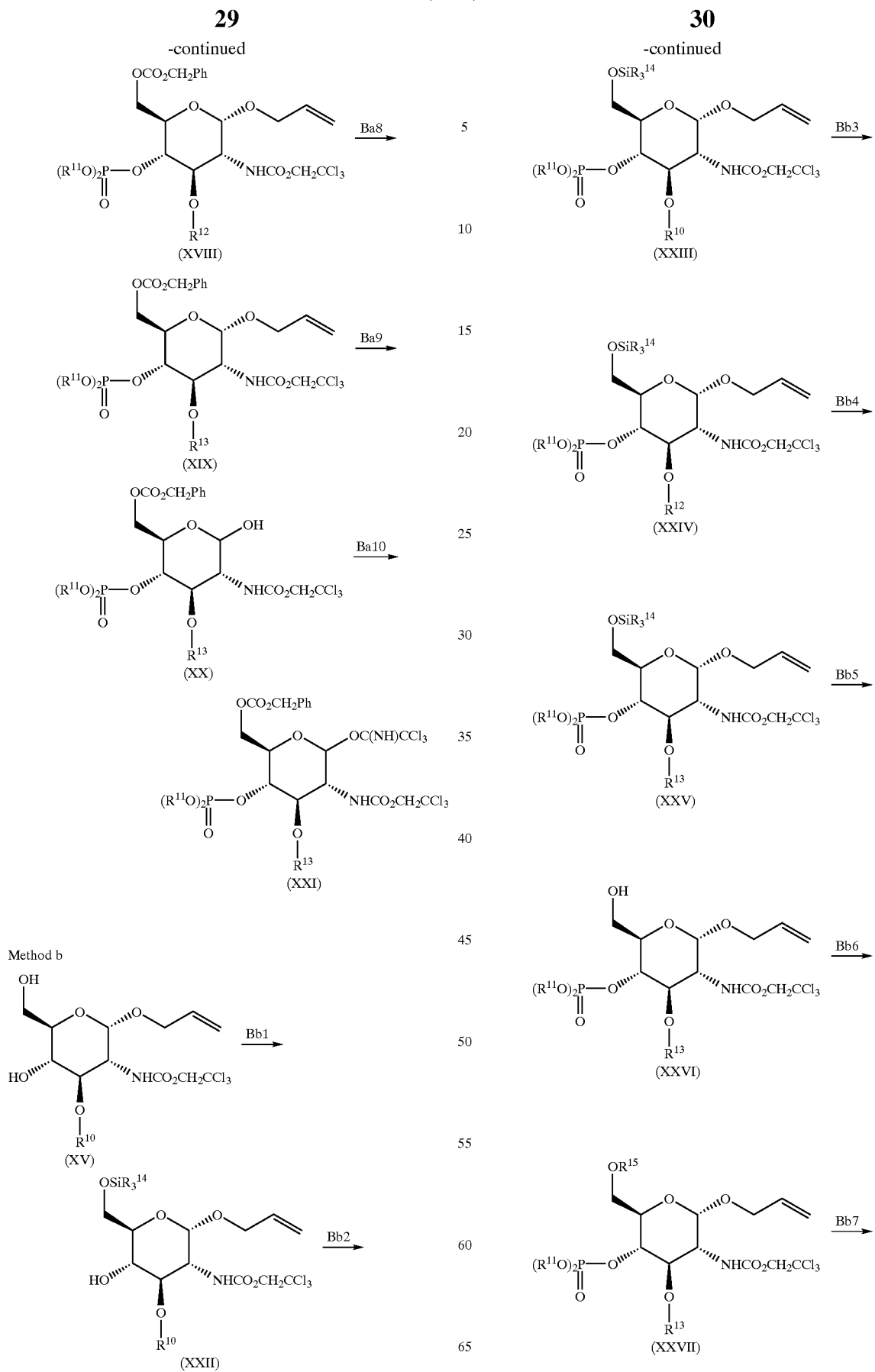

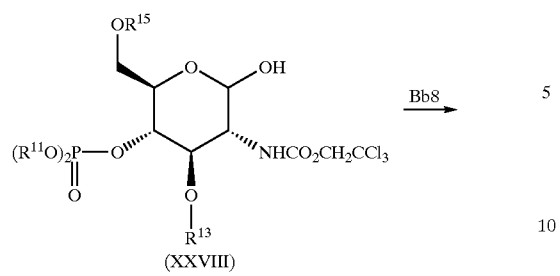
(XXVIII)
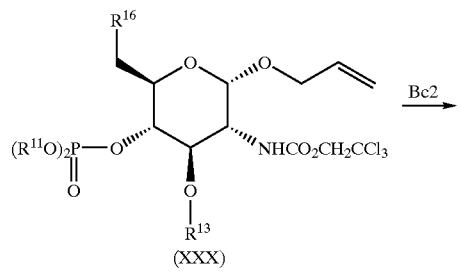
(XXX)
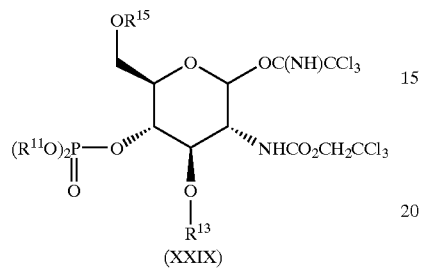
(XXIX)
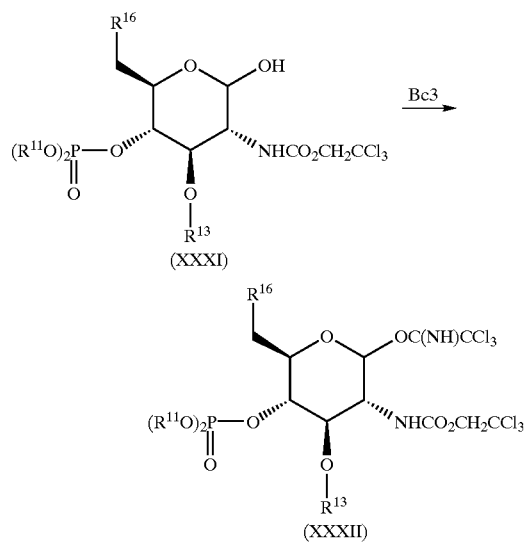
(XXXI)
(XXXII)
Method c
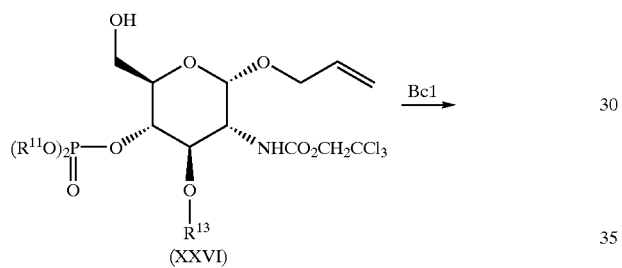
(XXVI)
Process C
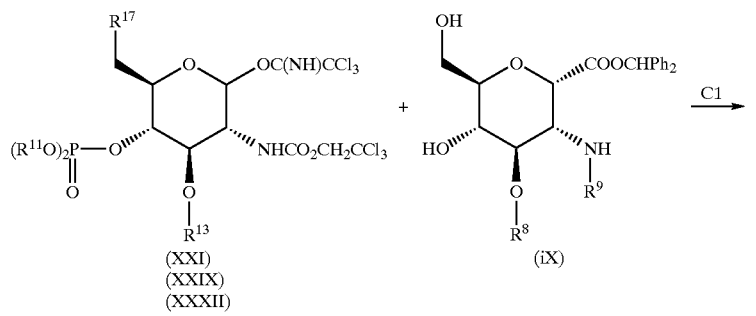
(XXI)
(XXIX)
(XXXII)
(iX)
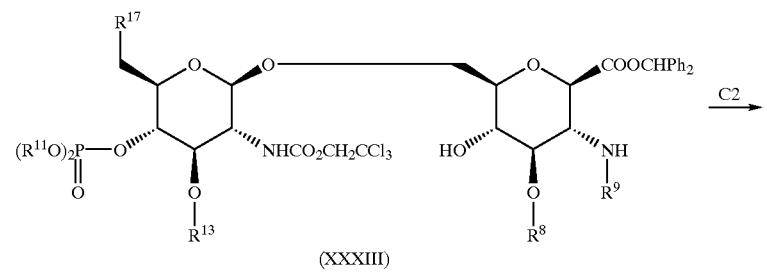
(XXXIII)

-continued (XXXIV) → (I)

In the above reaction scheme:

$R^1$, $R^2$, $R^3$, $R^4$ and $R^5$ are as defined above.

$R^6$ and $R^7$ may be the same or different, and each represents hydrogen, a $C_1$–$C_6$ alkyl group, or a $C_6$–$C_{10}$ aryl group.

$R^8$ is a $C_1$–$C_{20}$ alkyl group, a $C_2$–$C_{20}$ alkenyl group, or a $C_2$–$C_{20}$ alkynyl group which may optionally be substituted with one or more substituents selected from substituent group B.

The substituent group B includes a halogen atom, a protected hydroxy group (said protecting group is preferably a trichloroethoxycarbonyl group or a benzyl group), an oxo group, a $C_1$–$C_{20}$ alkoxy group which may optionally be substituted with an oxo group, a $C_2$–$C_{20}$ alkenyloxy group which may optionally be substituted with an oxo group, and a $C_2$–$C_{20}$ alkynyloxy group which may optionally be substituted with an oxo group.

$R^9$ is a $C_1$–$C_{20}$ alkanoyl group, a $C_2$–$C_{20}$ alkenoyl group or a $C_2$–$C_{20}$ alkynoyl group which may optionally be substituted with one or more substituents selected from substituent group C.

The substituent group C includes a halogen atom, a protected hydroxy group (said protecting group is preferably a trichloroethoxycarbonyl group or a benzyl group), an oxo group, a $C_1$–$C_{20}$ alkoxy group which may optionally be substituted with an oxo group, a $C_2$–$C_{20}$ alkenyloxy group which may optionally be substituted with an oxo group, and a $C_2$–$C_{20}$ alkynyloxy group which may optionally be substituted with an oxo group.

$R^{10}$ is a $C_1$–$C_{20}$ alkyl group, a $C_2$–$C_{20}$ alkenyl group, or a $C_2$–$C_{20}$ alkynyl group which may optionally be substituted with one or more substituents selected from substituent group D.

The substituent group D includes a halogen atom, a protected hydroxy group (said protecting group is preferably a trichloroethoxycarbonyl group or a p-methoxybenzyl group), an oxo group, a $C_1$–$C_{20}$ alkoxy group which may optionally be substituted with an oxo group, a $C_2$–$C_{20}$ alkenyloxy group which may optionally be substituted with an oxo group, and a $C_2$–$C_{20}$ alkynyloxy group which may optionally be substituted with an oxo group.

$R^{11}$ is an optionally substituted $C_6$–$C_{10}$ aryl group, an optionally substituted $C_7$–$C_{11}$ aralkyl group or a methyl group which may optionally be substituted with 1 to 3 aryl groups. Preferably $R^{11}$ is a phenyl group, a benzyl group or a diphenylmethyl group.

$R^{12}$ is a $C_1$–$C_{20}$ alkyl group, a $C_2$–$C_{20}$ alkenyl group, or a $C_2$–$C_{20}$ alkynyl group which may optionally be substituted with one or more substituents selected from substituent group E.

The substituent group E includes a halogen atom, a hydroxy group, an oxo group, a $C_1$–$C_{20}$ alkoxy group which may optionally be substituted with an oxo group, a $C_2$–$C_{20}$ alkenyloxy group which may optionally be substituted with an oxo group, and a $C_2$–$C_{20}$ alkynyloxy group which may optionally be substituted with an oxo group.

$R^{13}$ is a $C_1$–$C_{20}$ alkyl group, a $C_2$–$C_{20}$ alkenyl group or a $C_2$–$C_{20}$ alkynyl group which may optionally be substituted with one or more substituents selected from substituent group F.

The substituent group F includes a halogen atom, a protected hydroxy group (said protecting group is preferably a trichloroethoxycarbonyl group or a p-methoxybenzyl group), an oxo group, a $C_1$–$C_{20}$ alkoxy group which may optionally be substituted with an oxo group, a $C_2$–$C_{20}$ alkenyloxy group which may optionally be substituted with an oxo group, a $C_2$–$C_{20}$ alkynyloxy group which may optionally be substituted with an oxo group, a $C_1$–$C_{20}$ alkanoyloxy group which may optionally be substituted with an oxo group, a $C_3$–$C_{20}$ alkenoyloxy group which may optionally be substituted with an oxo group, a $C_3$–$C_{20}$ alkynoyloxy group which may optionally be substituted with an oxo group.

$R^{14}$ is a $C_1$–$C_4$ alkyl group.

$R^{15}$ is a $C_1$–$C_6$ alkyl group.

$R^{16}$ is a hydrogen atom or a halogen atom.

$R^{17}$ is a hydrogen atom, a halogen atom, a protected hydroxy group (said protecting group is a benzyloxycarbonyl group or a diphenylmethyl group), a $C_1$–$C_6$ alkoxy group which may optionally be substituted with an oxo group, a $C_2$–$C_6$ alkenyloxy group which may optionally be substituted with an oxo group, or a $C_2$–$C_6$ alkynyloxy group which may optionally be substituted with an oxo group.

The compound (I) of the present invention is produced through reactions of the following three processes:

(1) Process A is the step for preparation of intermediate (X).
(2) Process B is the step for preparation of intermediate (XXI), (XXIX) and (XXXII). Process B comprises three methods (Method Ba, Method Bb and Method Bc), one of which is selected depending on desired compound (I).
(3) Process C is the step for preparation of compound (D) through a condensation reaction of intermediate (X) obtained in Process A with intermediate (XXI), (XXIX) or (XXXII) obtained in Process B.

Each process is described below.

Process A (Step A1)

This step is a process for preparation of the 2-azido compound (III). This process is accomplished by treatment of a known compound (II) with an azidating reagent in the presence of a base in an inert solvent.

There is no particular restriction of the solvent provided that it has no adverse effect on the reaction and can dissolve the starting material to some extent. A preferred solvent is a halogeno hydrocarbon derivative such as methylene chloride, chloroform or carbon tetrachloride, or an alcohol derivative such as methanol or ethanol, preferably methanol.

A solution of trifluoromethanesulfonyl azide (0.4N) in methylene chloride is used as an azidation regent.

A preferred base is dimethylaminopyridine.

The reaction temperature is between −20 and 30° C., preferably between 15 and 25° C.

The reaction time is from 3 to 24 hours, preferably from 8 to 24 hours.

After the reaction the mixture is neutralized, concentrated and then partitioned between an organic solvent such as ethyl acetate and water. The organic layer is separated, washed with water, dried over anhydrous magnesium sulfate or the like and then is concentrated in vacuo to afford the desired product which, if necessary, is further purified by conventional procedures, for example recrystallization, silica gel chromatography or the like.

(Step A2)

This step is a process for the preparation of compound (IV) through alkylation, alkenylation or alkynylation of the 3-hydroxy group of compound (III). This process is accomplished by treatment of an alkoxide derivative of compound (III), which is prepared by reaction of compound (III) with a strong base, with an alkylating, alkenylating or alkynylating reagent in an inert solvent.

The solvent is an ether derivative such as dioxane or tetrahydrofiran, an amide derivative such as formnamide or dimethylformamide, or an aromatic hydrocarbon such as benzene or toluene, preferably dimethylformamide.

The alkylating agent is a halogeno hydrocarbon derivative or a sulfonic acid ester, preferably a sulfonic acid ester. In this step a compound of formula $R^8OSO_2CH_3$ ($R^8$ is as defined above) may be used.

The base is an alkali metal hydroxide such as sodium hydroxide or potassium hydroxide, an alkyllithium derivative such as n-butyllithium or tert-butyllithium, or an alkali metal hydride such as sodium hydride or potassium hydride, preferably sodium hydride.

The reaction temperature is between −78° C. and 80° C., preferably between 0° C. and 60° C.

The reaction time varies depending on the reaction temperature, the starting material, the reagent and the solvent; it is usually from 2 to 24 hours, preferably from 2 to 8 hours.

After the reaction the mixture is neutralized, concentrated and then partitioned between an organic solvent such as ethyl acetate and water. The organic layer is separated, washed with water, dried over anhydrous magnesium sulfate or the like and then is concentrated in vacuo to afford the desired product which, if necessary, is further purified by conventional procedures, for example recrystallization, silica gel chromatography or the like.

(Step A3)

This step is a process for preparation of compound (V) through removal of the 1-protecting group of compound (IV). This process is accomplished by isomerization of the 1-allyl group of compound (IV) by a metal catalyst in an inert solvent followed by hydrolysis.

The metal catalyst is a complex of palladium, rhodium or iridium, preferably (1,5-cyclooctadiene)bis (methyldiphenylphosphine)iridium(I) hexafluorophosphate ($[Ir(COD)(PMePh_2)_2]PF_6$).

The solvent is a halogeno hydrocarbon derivative such as methylene chloride, chloroform or carbon tetrachloride, an ether derivative such as ether, dioxane or tetrahydrofuran, an ester derivative such as ethyl acetate, or a nitrile derivative such as acetonitrile, preferably an ether derivative, more preferably tetrahydrofuran.

The reaction temperature is between 0 and 50° C., preferably between 5 and 25° C.

The reaction time is from 10 minutes to 24 hours, preferably from 30 minutes to 5 hours.

The hydrolysis of an isomerized vinyl ether derivative is conducted with a mineral acid such as hydrochloric acid or sulfuric acid, an organic acid such as p-toluenesulfonic acid, or iodine in an aqueous solution, preferably iodine in a mixture of pyridine and water.

The reaction temperature is between 0 and 100° C., preferably between 25 and 45° C.

The reaction time is from 10 minutes to 24 hours, preferably from 30 minutes to 5 hours.

After the reaction the mixture is neutralized, concentrated and then partitioned between an organic solvent such as ethyl acetate and water. The organic layer is separated, washed with water, dried over anhydrous magnesium sulfate or the like and then is concentrated in vacuo to afford the desired product which, if necessary, is further purified by conventional procedures, for example recrystallization, silica gel chromatography or the like.

(Step A4)

This step is a process for preparation of the trichloroacetimidate compound (VI). This process is accomplished by treatment of compound (V) having a 1-hydroxy group with trichloroacetonitrile in an inert solvent in the presence of a base.

The solvent is a halogeno hydrocarbon derivative such as methylene chloride, chloroform or carbon tetrachloride, an ether derivative such as ether, dioxane or tetrahydrofuran, an ester derivative such as ethyl acetate, or a nitrile derivative such as acetonitrile, preferably a halogeno hydrocarbon derivative, more preferably methylene chloride.

The base is an organic base such as 1,8-diazabicyclo [5.4.0]undec-7-ene (DBU) or an inorganic base such as sodium hydride, potassium carbonate or cesium carbonate, preferably an organic base, more preferably 1,8-diazabicyclo[5.4.0]undec-7-ene (DBU).

The reaction temperature is between −25 and 50° C., preferably between 0 and 25° C.

The reaction time is from 10 minutes to 24 hours, preferably from 30 minutes to 2 hours.

After the reaction the mixture is neutralized, concentrated and then partitioned between an organic solvent such as ethyl acetate and water. The organic layer is separated, washed with water, dried over anhydrous magnesium sulfate or the like and then is concentrated in vacuo to afford the desired product which, if necessary, is further purified by conventional procedures, for example recrystallization, silica gel chromatography or the like.

(Step A5)

This step is a process for preparation of the 1-cyano compound (VII). This process is accomplished by treatment of compound (VI) with a cyanating reagent in the presence of a catalyst in an inert solvent.

There is no particular restriction of the reaction solvent provided that it has no adverse effect on the reaction and can dissolve the starting material to some extent. The solvent is a nitrile derivative such as acetonitrile, or a halogeno hydrocarbon derivative such as methylene chloride, chloroform, carbon tetrachloride or dichloroethane, preferably a halogeno hydrocarbon derivative, more preferably methylene chloride.

The cyanating reagent is sodium cyanide, potassium cyanide, or trimethylsilyl cyanide, preferably trimethylsilyl cyanide.

The catalyst is a Lewis acid such as tin tetrachloride, trifluoroborane etherate, aluminium chloride, iron (II) chloride or trimethylsilyl triflate, preferably trimethylsilyl triflate.

The reaction temperature is between −40° C. and 100° C., preferably between 10° C. and 40° C.

The reaction time varies depending on the reaction temperature, the reagent and the solvent. It is usually from 10 minutes to 10 hours, preferably from 30 minutes to 5 hours.

After the reaction the mixture is neutralized, concentrated and then partitioned between an organic solvent such as ethyl acetate and water. The organic layer is separated, washed with water, dried over anhydrous magnesium sulfate or the like and then is concentrated in vacuo to afford the desired product which, if necessary, is further purified by conventional procedures, for example recrystallization, silica gel chromatography or the like.

(Step A6)

This step is a process for preparation the of 2-amino compound (VIII). This process is accomplished by reduction of the azide group of compound (VII) with a reducing reagent in an inert solvent.

There is no particular restriction of the reaction solvent provided that it has no adverse effect on the reaction and can dissolve the starting material to some extent. Such a solvent is an ether derivative miscible with water, such as tetrahydrofuran or dioxane, preferably tetrahydrofuran.

The reducing reagent of azide group is a mixture of phosphine derivatives and aqeuous ammonia, for example a trialkylphosphine and aqueous ammonia solution such as trimethylphosphine or triethylphosphine and aqueous ammonia solution or a triarylphosphine and aqueous ammonia solution such as triphenylphosphine and aqueous ammonia solution, preferably triphenylphosphine and aqueous ammonia solution.

The reduction reaction time is from 1 to 24 hours, preferably 1 hour.

The reaction temperature is between 0 and 50° C., preferably between 0° C. and 25° C.

The reaction temperature of the reaction of compound (VII) with a mixture of a phosphine derivative and aqueous ammonia solution is between 0 and 50° C., preferably room temperature.

After the reaction the mixture is neutralized, concentrated and then partitioned between an organic solvent such as ethyl acetate and water. The organic layer is separated, washed with water, dried over anhydrous magnesium sulfate or the like and then is concentrated in vacuo to afford the desired product which, if necessary, is further purified by conventional procedures, for example recrystallization, silica gel chromatography or the like.

(Step A7)

This step is a process for preparation of compound (IX) through acylation of the 2-amino group of compound (VIII). This process is accomplished by treatment of compound (VIII) with an acylating reagent.

The acylating reagent is a carboxylic acid derivative of formula $R^9OH$ (wherein $R^9$ is as defined above).

The solvent is an ether derivative such as dioxane or tetrahydrofuran, a halogeno hydrocarbon derivative such as methylene chloride, chloroform or carbon tetrachloride, or an amide derivative such as N,N-dimethylfoarnamide, preferably a halogeno hydrocarbon derivative, more preferably methylene chloride.

As a condensation reagent, dicyclohexylcarbodiimide may be used. Addition of 4-(dimethylamino)pyridine to the reaction mixture accelerates the reaction and depresses formation of by-products of the reaction.

The reaction temperature is between 0 and 50° C., preferably between 15 and 25° C. (room temperature).

The reaction time is from 1 to 24 hours, preferably 1 to 5 hours.

After the reaction the mixture is neutralized, concentrated and then partitioned between an organic solvent such as ethyl acetate and water. The organic layer is separated, washed with water, dried over anhydrous magnesium sulfate or the like and then is concentrated in vacuo to afford the desired product which, if necessary, is further purified by conventional procedure, for example recrystallization, silica gel chromatography or the like.

(Step A8)

This step is a process for preparation of compound (X) through removal of the 4-and 6-protecting group of compound (IX), conversion of the 1-nitrile group to a carboxy group and esterification. This process is accomplished by acid hydrolysis of compound (IX) in an inert solvent followed by treatment with an esterification reagent.

The solvent for hydrolysis is a water-miscible solvent, for example an alcohol derivative such as methanol or ethanol, an ether derivative such as diethyl ether, diisopropyl ether or tetrahydrofuran, a nitrile derivative such as acetonitrile, an amide derivative such as formamide, dimethylformamide, dimethylacetamide or hexamethylphosphoric triamide, preferably an ether derivative (dioxane).

The acid for hydrolysis is a mineral acid such as hydrochloric acid or sulfuric acid, preferably hydrochloric acid.

The reaction temperature is between 20 and 100° C., preferably between 50 and 80° C.

The reaction time is from 1 to 10 hours, preferably 2 to 5 hours.

After the reaction the mixture is concentrated in vacuo to afford the crude product which can be used in the next step of the reaction without purification.

There is no paticular restriction of the esterification reagent provided that it can be hydrolyzed by acid to yield a parent acid. Such an esterification reagent is diazomethane or diphenyldiazomethane, preferably diphenyldiazomethane.

The solvent is an ether derivative such as dioxane or tetrahydrofuran, a halogeno hydrocarbon derivative such as methylene chloride, chloroform or carbon tetrachloride, or an amide derivative such as dimethylformamide, preferably an amide derivative, more preferably dimethylformamide.

The reaction temperature is between 0 and 100° C., preferably between 25 and 60° C.

The reaction time is from 30 minutes to 24 hours, preferably 1 to 10 hours.

After the reaction the mixture is neutralized, concentrated and then partitioned between an organic solvent such as ethyl acetate and water. The organic layer is separated, washed with water, dried over anhydrous magnesium sulfate or the like and then is concentrated in vacuo to afford the desired product which, if necessary, is further purified by conventional procedures, for example recrystallization, silica gel chromatography or the like.

Compound (I) can be produced by a condensation reaction of compound (X) obtained in this step with compound (XXI), (XXIX) or (XXXII) described below.

Process B (Method Ba)

(Step Ba1)

This step is a process for preparation of compound (XII) through alkylation of the 3-hydroxy group of compound (XI). This process is accomplished by a similar procedure to that described in Step A2.

The alkylation reagent is a sulfonic acid ester of formula $R^{10}OSO_2CH_3$ (wherein $R^{10}$ is as defined above).

(Step Ba2)

This step is a process for preparation of compound (XIII) through removal of the 2-protecting group of compound (XII). This process is accomplished by treatment of compound (XII) with a base in an inert sovent.

The solvent is an alcohol derivative such as methanol or ethanol, an ether derivative such as diethyl ether or tetrahydrofuran, a nitrile derivative such as acetonitrile, or a ketone derivative such as acetone or methyl ethyl ketone, preferably an alcohol derivative (ethanol).

The base is an alkali metal bicarbonate such as sodium bicarbonate or potassium bicarbonate, an alkali metal hydroxide such as sodium hydroxide or potassium hydroxide, or an alkali metal alkoxide such as sodium methoxide or sodium ethoxide, preferably an alkali metal hydroxide.

The reaction temperature is between 0° C. and 100° C., preferably between 25° C. and 80° C.

The reaction time is from 30 minutes to 24 hours, preferably 1 to 5 hours.

After the reaction the mixture is neutralized, concentrated and then partitioned between an organic solvent such as ethyl acetate and water. The organic layer is separated, washed with water, dried over anhydrous magnesium sulfate or the like and then is concentrated in vacuo to afford the desired product which, if necessary, is further purified by conventional procedures, for example recrystallization, silica gel chromatography or the like.

(Step Ba3)

This step is a process for preparation of compound (XIV) through protection of the 2-amino group of compound (XIII). This process is accomplished by treatment of compound (XIII) a with protecting reagent in the presence of a base in an inert solvent.

The solvent is a halogenated hydrocarbon derivative such as methylene chloride, chloroform or carbon tetrachloride, an ether derivative such as ether, dioxane or tetrahydrofuran, or a nitrile derivative such as acetonitrile, preferably a halogenated hydrocarbon derivative, more preferably methylene chloride.

The protecting reagent which does not prevent the glycosidation of CI step 1 is preferably trichloroethoxycarbonyl chloride.

The base is a pyridine derivative such as pyridine or dimethylaminopyridine, a trialkylamine derivative such as triethylamine or tributylamine, or an alkali metal bicarbonate such as sodium bicarbonate or potassium bicarbonate, preferably an alkali metal bicarbonate (sodium bicarbonate).

The reaction temperature is between −20° C. and 60° C., preferably between 0° C. and 25° C.

The reaction time is from 30 minutes to 24 hours, preferably 1 to 5 hours.

After the reaction the mixture is neutralized, concentrated and then partitioned between an organic solvent such as ethyl acetate and water. The organic layer is separated, washed with water, dried over anhydrous magnesium sulfate or the like and then is concentrated in vacuo to afford the desired product which, if necessary, is further purified by conventional procedures, for example recrystallization, silica gel chromatography or the like.

(Step Ba4)

This step is a process for removal of the 4- and 6-protecting group of compound (XIV). This process is accomplished by treatment of compound (XIV) with an acid.

The acid is an inorganic acid such as hydrochloric acid or sulfuric acid or an organic acid such as acetic acid or oxalic acid, preferably an organic acid, more preferably acetic acid diluted with water (70–90%).

The reaction temperature is between 20 and 100° C., preferably between 40 and 80° C.

The reaction time is from 10 minutes to 24 hours, preferably 30 minutes to 5 hours.

After the reaction the mixture is neutralized, concentrated and then partitioned between an organic solvent such as ethyl acetate and water. The organic layer is separated, washed with water, dried over anhydrous magnesium sulfate or the like and then is concentrated in vacuo to afford the desired product which, if necessary, is further purified by conventional procedures, for example recrystallization, silica gel chromatography or the like.

(Step Ba5)

This step is a process for preparation of compound (XVI) through selective protection of the 6-hydroxy group of compound (XV). This process is accomplished by treatment of compound (XV) with an esterification reagent in the presence of a base in an inert solvent.

The protecting reagent which can selectively be removed to afford the 6-hydroxy compound in good yield is, for example, an alkyloxycarbonyl halide such as tert-butoxycarbonyl chloride, an aralkyloxycarbonyl halide such as benzyloxycarbonyl chloride, a halogeno-alkoxycarbonyl halide such as trichloroethoxycarbonyl chloride, or an alkyl halide substituted with aryl groups such as triphenylmethyl chloride or diphenylmethyl chloride, preferably benzyloxycarbonyl chloride.

The base is an organic base such as pyridine, dimethylaminopyridine, triethylamine or N,N-dimethylaniline, preferably pyridine.

The solvent is a halogenated hydrocarbon derivative such as methylene chloride, chloroform or carbon tetrachloride, an ether derivative such as ether, dioxane or tetrahydrofuran, or an ester derivative such as ethyl acetate, preferably a halogenated hydrocarbon derivative, more preferably methylene chloride.

The reaction temperature is between −50 and 50° C., preferably between −10 and 30° C.

The reaction time is from 10 minutes to 24 hours, preferably 30 minutes to 5 hours.

After the reaction the mixture is neutralized, concentrated and then partitioned between an organic solvent such as ethyl acetate and water. The organic layer is separated, washed with water, dried over anhydrous magnesium sulfate or the like and then is concentrated in vacuo to afford the desired product which, if necessary, is further purified by conventional procedures, for example recrystallization, silica gel chromatography or the like.

(Step Ba6)

This step is a process for preparation of compound (XVII) through phosphorylation of the 4-hydroxy group of compound (XVI). This process is accomplished by treatment of compound (XVI) with a phosphorylating reagent in the presence of a base in an inert solvent.

The phosphorylating reagent is a phosphoric acid halide of formula $(R^{11}-O)_2P(=O)X$, wherein X is a halogen atom such as a chlorine, bromine or iodine atom, preferably a chlorine atom, the group $R^{11}$ of which can be removed to afford compound (I) in good yield when phosphoric acid ester compound (XXXV) is converted to compound (I) by deprotection of a protecting group of compound (XXXV). A preferred phosphorylating reagent is benzylphosphoryl chloride or phenylphosphoryl chloride.

The base is an organic base such as pyridine, dimethylaminopyridine, triethylamine or N,N-dimethylaniline, preferably dimethylaminopyridine.

The solvent is a halogenated hydrocarbon derivative such as methylene chloride, chloroform or carbon tetrachloride, an ether derivative such as ether, dioxane or tetrahydrofuran, or an ester derivative such as ethyl acetate, preferably a halogenated hydrocarbon derivative (methylene chloride).

The reaction temperature is between 0 and 50° C., preferably between 5 and 30° C.

The reaction time is from 10 minutes to 24 hours, preferably 30 minutes to 5 hours.

After the reaction the mixture is neutralized, concentrated and then partitioned between an organic solvent such as ethyl acetate and water. The organic layer is separated, washed with water, dried over anhydrous magnesium sulfate or the like and then is concentrated in vacuo to afford the desired product which, if necessary, is further purified by conventional procedures, for example recrystallization, silica gel chromatography or the like.

(Step Ba7)

This step is a process for preparation of compound (XVIII) through removal of the p-methoxybenzyl group of compound (XVII) when compound (XVII) has a p-methoxybenzyl group in the 3-alkyl group ($R^{10}$). This process is accomplished by treatment of compound (XVII) with a deprotecting reagent in the presence of water in an inert solvent.

This process is optional and if not necessary, Ba9 step can be performed.

The solvent is a nitrile derivative such as acetonitrile or a halogenated hydrocarbon derivative such as methylene chloride or chloroform, preferably methylene chloride.

The deprotecting reagent is ceric ammonium nitrate (CAN), N-bromosuccinimide (NBS), triphenylcarbenium tetrafluoroborate, or 2,3-dichloro-5,6-dicyano-p-benzoquinone (DDQ), preferably 2,3-dichloro-5,6-dicyano-p-benzoquinone (DDQ).

The reaction temperature is between 0 and 30° C., preferably between 15 and 25° C.

The reaction time is from 30 minutes to 8 hours, preferably 1 to 5 hours.

After the reaction the mixture is neutralized, concentrated and then partitioned between an organic solvent such as ethyl acetate and water. The organic layer is separated, washed with water, dried over anhydrous magnesium sulfate or the like and then is concentrated in vacuo to afford the desired product which, if necessary, is further purified by conventional procedures, for example recrystallization, silica gel chromatography or the like.

(Step Ba8)

This step is a process for preparation of compound (XIX) through acylation of a hydroxy group in the 3-alkyl group ($R^{12}$) of compound (XVIII). This process is accomplished by treatment of compound (XVIII) with an acylating reagent in the presence of a base in an inert solvent. This step is also optional.

The acylating reagent is preferably a $C_{12}$–$C_{14}$ alkanoyl chloride, more preferably myristoyl chloride.

The solvent is an ether derivative such as tetrahydrofuran or dioxane, a halogenated hydrocarbon derivative such as methylene chloride, chloroform or carbon tetrachloride, or an amide derivative such as N,N-dimethylamide, preferably an ether derivative, more preferably tetrahydrofuran.

The base is an organic base such as pyridine, dimethylaminopyridine, triethylamine or N,N-dimethylaniline, preferably dimethylaminopyridine or triethylamine.

The reaction temperature is between 0 and 80° C., preferably between 0 and 25° C.

The reaction time is from 1 to 24 hours, preferably 1 to 8 hours.

After the reaction the mixture is neutralized, concentrated and then partitioned between an organic solvent such as ethyl acetate and water. The organic layer is separated, washed with water, dried over anhydrous magnesium sulfate or the like and then is concentrated in vacuo to afford the desired product which, if necessary, is further purified by conventional procedures, for example recrystallization, silica gel chromatography or the like.

(Step Ba9)

This step is a process for preparation of compound (XX) through removal of the 1-allyl group of compound (XIX). This process is accomplished by a similar procedure to that described in Step A3.

(Step Ba10)

This step is a process for preparation of the trichloroacetimidate derivative (XXI) which is one of the important intermediates. This process is accomplished by treatment with trichloroacetonitrile in the presence of a base in an inert solvent in a similar manner to that described in Step A4.

After the reaction the mixture is neutralized, concentrated and then partitioned between an organic solvent such as ethyl acetate and water. The organic layer is separated, washed with water, dried over anhydrous magnesium sulfate or the like and then is concentrated in vacuo to afford the desired product which, if necessary, is further purified by conventional procedures, for example recrystallization, silica gel chromatography or the like.

Method Bb (Step Bb1)

This step is a process for preparation of compound (XXII) through selective protection of the 6-hydroxy group of compound (XV) which is obtained in Step Ba4. This process is accomplished by treatment of compound (XV) with a silylating reagent in the presence of a base in an inert solvent.

The silylating reagent is a trialkylsilyl halide or trialkylsilyl trifluoromethanesulfonate of formula $(R^{14})_3SiX'$ (wherein $R^{14}$ is as defined above, and X' is a halogen atom or a trifluoromethanesulfonyl group), preferably tert-butyldimethylsilyl chloride.

The base is a pyridine derivative such as pyridine or dimethylaminopyridine, a trialkylamine such as triethylamine or tributylamine, an aniline derivative such as aniline or N,N-dimethylaniline, or a lutidine derivative such as 2,6-lutidine, preferably dimethylaminopyridine.

The solvent is a halogenated hydrocarbon derivative such as methylene chloride, chloroform or carbon tetrachloride, an ether derivative such as ether, tetrahydrofuran or dioxane, or a nitrile derivative such as acetonitrile, preferably methylene chloride.

The reaction temperature is between 0 and 50° C., preferably between 15 and 25° C.

The reaction time is from 1 to 24 hours, preferably 1 to 8 hours.

After the reaction the mixture is neutralized, concentrated and then partitioned between an organic solvent such as ethyl acetate and water. The organic layer is separated, washed with water, dried over anhydrous magnesium sulfate or the like and then is concentrated in vacuo to afford the desired product which, if necessary, is further purified by conventional procedures, for example recrystallization, silica gel chromatography or the like.

(Step Bb2)

This step is a process for preparation of compound (XXIII) through phosphorylation of the 4-hydroxy group of compound (XXII). This process is accomplished by a similar procedure to that described in Step Ba6.

(Step Bb3)

This step is a process for preparation of compound (XXIV) through removal of a protecting group in the 3-alkyl group ($R^{10}$) of compound (XXIII). This process is accomplished by a similar procedure to that described in Step Ba7.

This process is optional and if not necessary, Step Bb5 can be performed.

(Step Bb4)

This step is a process for preparation of compound (XXV) through acylation of a hydroxy group in the 3-alkyl group ($R^{12}$) of compound (XXIV). This process is accomplished by a similar procedure to that described in Step Ba8. This step is also optional.

(Step Bb5)

This step is a process for preparation of compound (XXVI) through removal of the 6-protecting group of compound (XXV). This process is accomplished by hydrolysis of compound (XXV) with acid in an inert solvent.

The acid is an inorganic acid such as hydrochloric acid or sulfuric acid or an organic acid such as acetic acid or oxalic acid, preferably 3N hydrochloric acid.

The solvent is a water-miscible solvent such as dioxane or tetrahydrofuran, preferably tetrahydrofuran.

The reaction temperature is between 20 and 80° C., preferably between 20 and 50° C.

The reaction time is from 30 minutes to 24 hours, preferably 1 to 8 hours.

After the reaction the mixture is neutralized, concentrated and then partitioned between an organic solvent such as ethyl acetate and water. The organic layer is separated, washed with water, dried over anhydrous magnesium sulfate or the like and then is concentrated in vacuo to afford the desired product which, if necessary, is further purified by conventional procedures, for example recrystallization, silica gel chromatography or the like.

(Step Bb6)

This step is a process for preparation of compound (XXVII) through alkylation of the 6-hydroxy group of compound (XXVI). When $R^{15}$ is a $C_1$–$C_6$ alkyl group this process is accomplished by method (1) and when $R^{15}$ is a methyl group, this process may also be accomplished by method (2).

Method (1): In the case when $R^{15}$ is a $C_1$–$C_6$ alkyl group:

Method (1) is accomplished by treatment of compound (XXVI) with an alkylating reagent in the presence of a base or silver (II) oxide (AgO) in an inert solvent.

There is no particular restriction of the solvent provided that it has no adverse effect on the reaction and can dissolve the starting material to some extent. Such a solvent is an aliphatic hydrocarbon drivative such as hexane, heptane or ligroin, an aromatic hydrocarbon derivative such as benzene, toluene or xylene, a halogeno hydrocarbon derivative such as methylene chloride, chloroform, carbon tetrachloride, dichloroethane or chlorobenzene, an ester derivative such as ethyl acetate, propyl acetate or diethyl carbonate, an ether derivative such as diethyl ether, diisopropyl ether, tetrahydrofuran or dioxane, a nitrile derivative such as acetonitrile or isobutyronitrile, or an amide derivative such as formamide, N,N-dimethylformamide or N,N-dimethylacetamide, preferably an ether derivative.

The base is an alkali metal carbonate such as sodium carbonate or potassium carbonate, an alkali metal bicarbonate such as sodium bicarbonate or potassium bicarbonate, an alkali metal hydride such as sodium hydride or potassium hydride, or an organic base such as N-methylmorpholine, triethylamine, tributylamine, diisopropylethylamine, dicyclohexylamine, N-methylpiperidine, pyridine, picoline, 4-(N,N-dimethylamino)pyridine, 2,6-di(tert-butyl)-4-methylpyridine, N,N-dimethylaniline, N,N-diethylaniline, 5-diazabicyclo[4.3.0]non-5-ene (DBN), 1,4-diazabicyclo[2.2.2]octane (DABCO) or 1,8-diazabicyclo[5.4.0]undec-7-ene (DBU), preferably an organic base, more preferably triethylamine, DBN or DBU.

The alkylating reagent is a compound of formula $R^{15}Z$ (wherein $R^{15}$ is as defined above, and Z is an iodine atom, a bromine atom, a chlorine atom, a p-toluenesulfonyloxy group, or a methanesulfonyloxy group).

The reaction temperature is between 0° C. and 100° C., preferably between 0° C. and 30° C.

The reaction time is from 10 minutes to 24 hours, preferably 1 to 18 hours. Method (2): In the case when $R^{15}$ is a methyl group:

Method (2) is accomplished by treatment of compound (XXVI) with trimethyloxonium tetrafluoroborate in the presence of a base in an inert solvent.

The solvent is an ether derivative such as ether, tetrahydrofuran or dioxane, a halogeno hydrocarbon derivative such as methylene chloride, chloroform or carbon tetrachloride, or an amide derivative such as formamide, N,N-dimethylformamide or N,N-dimethylacetamide, preferably methylene chloride.

The base is preferably 2,6-di(tert-butyl)-4-methylpyridine.

The reaction temperature is between −50° C. and 100° C., preferably between 0° C. and 30° C.

The reaction time is from 1 to 24 hours, preferably 2 to 5 hours.

After the reaction the mixture is neutralized, concentrated and then partitioned between an organic solvent such as ethyl acetate and water. The organic layer is separated, washed with water, dried over anhydrous magnesium sulfate or the like and then is concentrated in vacuo to afford the desired product which, if necessary, is further purified by conventional procedures, for example recrystallization, silica gel chromatography or the like.

(Step Bb7)

This step is a process for preparation of compound (XXVIII) through removal of the 1-allyl group of compound (XXVII). This process is accomplished by a similar procedure to that described in Step A3.

(Step Bb8)

This step is a process for preparation of the trichloroacetimidate derivative (XXIX) which is one of the important intermediates. This process is accomplished by a similar procedure to that described in Step Ba10 using compound (XXVIII).

Process Bc (Step Bc1)

This step is a process for preparation of compound (XXX) through conversion of the 6-hydroxy group of compound (XXVI) obtained in Step Bb5 to a halogen or hydrogen atom.

(Step 1 Bc1)

This step is a process for preparation of compound (XXX) wherein $R^{16}$ is a halogen atom. This process is accomplished by one of methods (1), (2) and (3) described below.

Method (1) In the case when $R^{16}$ is a fluorine atom:

This process is accomplished by treatment of compound (XXVI) with a fluorination reagent in an inert solvent.

The solvent is a halogeno hydrocarbon derivative such as methylene chloride or fluorotrichloromethane, or an ether derivative such as ether or 1,2-dimethoxyethane, preferably methylene chloride.

The fluorination reagent is, for example, (2-fluoroethyl) dimethylamine or (diethylamino)sulfur trifluoride (DAST), preferably DAST.

The reaction temperature is between −78° C. and 25° C., preferably between 0° C. and 25° C.

The reaction time is from 1 to 18 hours, preferably 1 to 5 hours.

Method (2) In the case when $R^{16}$ is a chlorine or bromine atom:

This process is accomplished by treatment of compound (XXVI) with phosphorus trichloride, phosphorus tribromide, phosphoryl chloride, phosphoryl bromide, thionyl chloride or thionyl bromide in an inert solvent.

The solvent is preferably a halogeno hydrocarbon derivative such as methylene chloride, chloroform or carbon tetrachloride.

The reaction temperature is between −50° C. and 50° C., preferably between −10° C. and 30° C.

The reaction time is from 1 to 18 hours, preferably 1 to 5 hours.

Method (3) In the case when $R^{16}$ is an iodine atom:

This process is accomplished by treatment of compound (XXVI) with iodine and triphenylphosphine in an inert solvent.

There is no particular restriction of the solvent provided that it has no adverse effect on the reaction and it can dissolve the starting material to some extent. Such a solvent is an aliphatic hydrocarbon drivative such as hexane, heptane or ligroin, an aromatic hydrocarbon derivative such as benzene, toluene or xylene, a halogeno hydrocarbon derivative such as methylene chloride, chloroform, carbon tetrachloride, dichloroethane or chlorobenzene, an ester derivative such as ethyl acetate, propyl acetate or diethyl carbonate, an ether derivative such as diethyl ether, diisopropyl ether, tetrahydrofuran or dioxane, an alcohol derivative such as methanol or ethanol, or an amide derivative such as formamide, N,N-dimethylformamide or N,N-dimethylacetamide, preferably an ether derivative.

The reaction temperature is between −50° C. and 100° C., preferably between 0° C. and 30° C.

The reaction time is from 1 to 18 hours, preferably 1 to 5 hours.

After the reaction the desired compound (XXX) is isolated by conventional procedures. For example, the reaction mixture is neutralized, concentrated and then partitioned between an organic solvent such as ethyl acetate and water. The organic layer is separated, washed with water, dried over anhydrous magnesium sulfate or the like and then is concentrated in vacuo to afford the desired product which, if necessary, is further purified by conventional procedures, for example recrystallization, silica gel chromatography or the like.

(Bc1 Step 2)

This step is a process for preparation of compound (XXX) wherein $R^{16}$ is a hydrogen atom. This process is accomplished by treatment of a compound, which is obtained in Bc1 Step 1 Method (2) and wherein $R^{16}$ is a bromine atom, with tributyltin hydride or lithium aluminium hydride in an inert solvent.

The solvent is an aliphatic hydrocarbon drivative such as hexane, heptane or ligroin, an aromatic hydrocarbon derivative such as benzene, toluene or xylene, or an ether derivative such as diethyl ether, diisopropyl ether, tetrahydrofuran or dioxane, preferably an ether derivative.

The reaction temperature is between −50° C. and 50° C., preferably between −10° C. and 30° C.

The reaction time is from 10 minutes to 16 hours, preferably 1 to 8 hours.

After the reaction the desired compound (XXX) is isolated by conventional procedures. For example, the reaction mixture is neutralized, concentrated and then partitioned between an organic solvent such as ethyl acetate and water. The organic layer is separated, washed with water, dried over anhydrous magnesium sulfate or the like and then is concentrated in vacuo to afford the desired product which, if necessary, is further purified by conventional procedures, for example recrystallization, silica gel chromatography or the like.

(Step Bc2)

This step is a process for preparation of compound (XXXI) through removal of the 1-allyl group of compound (XXX). This process is accomplished by a similar procedure to that described in Step A3.

(Step Bc3)

This step is a process for preparation of the trichloroacetimidate derivative (XXXII) which is one of the important intermediates. This process is accomplished by a similar procedure to that described in Step Ba10.

Process C (Step C1)

This step is a process for preparation of compound (XXXIII) having lipid A structure through a reaction of an intermediate (XXI), (XXIX) or (XXXII) with an intermediate (X). This process is accomplished by glycosidation of a compound (XXI), (XXIX) or (XXXII) with a compound (X) in the presence of an acid catalyst in an inert solvent.

The acid catalyst is a Lewis acid such as tin tetrachloride, trifluoroborane etherate, aluminium chloride, iron (II) chloride or trimethylsilyl triflate, preferably trimethylsilyl triflate.

The solvent is a halogeno hydrocarbon such as methylene chloride or chloroform, an ether derivative such as diethyl ether, a nitrile derivative such as acetonitrile, an aromatic hydrocarbon derivative such as benzene or toluene, or an amide derivative such as N,N-dimethylformamide, preferably a halogeno hydrocarbon derivative, more preferably methylene chloride.

The reaction temperature is between −100 and 25° C., preferably between −78 and 0° C.

The reaction time is from 10 minutes to 10 hours, preferably 30 minutes to 5 hours.

After the reaction the mixture is neutralized, concentrated and then partitioned between an organic solvent such as ethyl acetate and water. The organic layer is separated, washed with water, dried over anhydrous magnesium sulfate or the like and then is concentrated in vacuo to afford the desired product which, if necessary, is further purified by conventional procedures, for example recrystallization, silica gel chromatography or the like.

(Step C2)

This step is a process for preparation of compound (XXXIV) through removal of the trichloroethoxycarbonyl group of compound (XXXIII) followed by conversion to acyl group $R^3$. This process is accomplished by treatment of compound (XXXIII) with a deprotecting reagent in an inert solvent and treatment of the deprotected product with acylating reagent.

The solvent of deprotection reaction is acetic acid.

The deprotecting reagent for the trichloroethoxycarbonyl group is zinc powder.

The reaction temperature is between 0 and 80° C., preferably between 10 and 30° C.

The reaction time is from 1 to 24 hours, preferably 1 to 8 hours.

The acylating reagent is a carboxylic acid of formula $R^3OH$ or an acid anhydride of formula $(R^3)_2O$ (wherein $R^3$ is as defined above). The acylation can be conducted in a similar procedure to that described in Step A7.

(Step C3)

This step is a process for preparation of compound (I) of the present invention through removal of the 1-protecting group, protecting groups for hydroxy groups $R^8$, $R^9$, $R^{13}$ and $R^7$ and protecting group $R^{11}$ for the phosphoric acid group. This process is accomplished by procedures described by Greene, T. W. et al., "Protective Groups in Organic Synthesis", John Wiley & Sons (1991) or procedures described below. In addition, when compound (XXXIV) has several kinds of protecting groups, removal of these protecting groups can be achieved step by step in an appropriate combination of deprotection reactions depending on the protecting groups.

Deprotection (1) in the case that protecting group is an aralkyl group:

This step is a process of removal of aralkyl group. This process is accomplished by catalytic reduction in an atmosphere of hydrogen in the presence of a catalyst in an inert solvent.

The catalyst is palladium on carbon, palladium hydroxide, palladium hydroxide on carbon or palladium black, preferably palladium on carbon.

The solvent is an ether derivative such as tetrahydrofuran, dioxane or ether, an ester derivative such as ethyl acetate, an alcohol derivative such as methanol or ethanol, or an organic acid derivative such as acetic acid or formic acid, preferably ethanol.

The reaction temperature is between 0 and 50° C., preferably between 15 and 25° C.

The reaction time is from 1 to 48 hours, preferably 1 to 24 hours.

After the reaction the catalyst is removed by filtration. The filtrate is concentrated in vacuo to afford the desired product which, if necessary, is further purified by conventional procedures, for example recrystallization, silica gel chromatography or the like.

Deprotection (2) in the case that protecting group is a diphenylmethyl group:

This step is a process for removal of diphenylmethyl group This process is accomplished by catalytic reduction in an atmosphere of hydrogen by similar procedure to that described in Deprotection (1) or by treatment with an acid in an inert solvent. When compound (XXXIV) has a double bond or triple bond the treatment of compound (XXXIV) with an acid can be used.

There is no particular restriction of the acid provided that it is an usual Bronsted or Lewis acid. A preferred acid is an inorganic acid such as hydrochloric acid, sulfuric acid or nitric acid, or an organic acid such as acetic acid, trifluoroacetic acid, methanesulfonic acid or p-toluenesulfonic acid.

There is no particular restriction of the solvent provided that it has no adverse effect on the reaction and it can dissolve the starting material to some extent. Such a solvent is an aliphatic hydrocarbon drivative such as hexane, heptane or ligroin, an aromatic hydrocarbon derivative such as benzene, toluene or xylene, a halogeno hydrocarbon derivative such as methylene chloride, chloroform, carbon tetrachloride, dichloroethane or chlorobenzene, an ester derivative such as ethyl acetate, propyl acetate, butyl acetate or diethyl carbonate, an ether derivative such as diethyl ether, diisopropyl ether, tetrahydrofuran or dioxane, an alcohol derivative such as methanol, ethanol, propanol, butanol or isoamyl alcohol, a ketone derivative such as acetone, methyl ethyl ketone or cyclohexanone, water or mixtures of these solvents, preferably a halogeno hydrocarbon derivative, an ester derivative or an ether derivative.

The reaction temperature and reaction time vary depending on the nature of the starting material, solvent and acid, and the concentration of acid. The reaction temperature is usually between −10 and 100° C., preferably between −5 and 50° C. The reaction time is usually from 5 minutes to 48 hours, preferably 30 minutes to 10 hours.

After the reaction the desired product is isolated by conventional procedures. For example the reaction mixture is concentrated and then partitioned between an organic solvent such as ethyl acetate and water. The organic layer is separated, washed with water, dried over anhydrous magnesium sulfate or the like and then is concentrated in vacuo to afford the desired product which, if necessary, is further purified by conventional procedures, for example recrystallization, reprecipitation, silica gel chromatography or the like.

Deprotection (3) in the case that $R^{11}$ in a protecting group of phosphoric acid group is a phenyl group:

This process is accomplished by catalytic reduction in the presence of a catalyst in an inert solvent.

The catalyst is preferably platinum oxide.

The solvent is an ether derivative such as tetrahydrofuran, dioxane or ether, an ester derivative such as ethyl acetate, an alcohol derivative such as methanol or ethanol, or an organic acid derivative such as acetic acid or formic acid, preferably tetrahydrofuran.

The reaction temperature is between 0 and 50° C., preferably between 15 and 25° C.

The reaction time is from 1 to 48 hours, preferably 1 to 24 hours.

After the reaction the catalyst is removed by filtration. The filtrate is concentrated in vacuo to afford the desired product which, if necessary, is further purified by conventional procedures, for example recrystallization, reprecipitation, silica gel chromatography or the like.

An ester derivative of compound (I) of the present invention may be prepared by treatment with an esterification reagent in a conventional procedure. The esterification reaction is conducted, if necessary, before or after protection of a hydroxy group or before or after deprotection of a hydroxy group.

Esterification method (1) where an alkyl halide derivative is used in order to prepare a desired ester derivative.

Esterification method (2) where an alcohol derivative is used in order to prepare a desired ester derivative.

In esterification method (1):

There is no particular restriction of the solvent provided that it has no adverse effect on the reaction and can dissolve the starting material to some extent. A preferred solvent is an aliphatic hydrocarbon drivative such as hexane or heptane, an aromatic hydrocarbon derivative such as benzene, toluene or xylene, a halogeno hydrocarbon derivative such as methylene chloride, chloroform, carbon tetrachloride, dichloroethane or dichlorobenzene, an ether derivative such as diethyl ether, diisopropyl ether, tetrahydrofuran, dioxane, dimethoxyethane or di(ethylene glycol) dimethyl ether, a ketone derivative such as acetone, methyl ethyl ketone, methyl isobutyl ketone, isophorone or cyclohexanone, a nitrile derivative such as acetonitrile or isobutyronitrile, or an amide derivative such as formamide, N,N-dimethylformamide, or N,N-dimethylacetamide, N-methyl-2-pyrrolidone, N-methylpyrrolidinone, or hexamethylphosphoric triamide.

In the esterification method (1) a base is used as a catalyst. There is no particular restriction of the base provided that it can be used as a base in a conventional reaction. A preferred base is an inorganic base, for example an alkali metal carbonate such as sodium carbonate, potassium carbonate or lithium carbonate, an alkali metal bicarbonate such as sodium bicarbonate, potassium bicarbonate or lithium bicarbonate, an alkali metal hydride such as lithium hydride, sodium hydride or potassium hydride, an alkali metal hydroxide such as sodium hydroxide, potassium hydroxide, barium hydroxide or lithium hydroxide, an alkali metal fluoride such as sodium fluoride or potassium fluoride; an alkali metal alkoxide such as sodium methoxide, sodium ethoxide, potassium methoxide, potassium ethoxide, potassium tert-butoxide or lithium methoxide; an alkali metal mercaptan such as sodium methylmercaptan, or sodium ethylmercaptan; an organic base such as N-methylmorpholine, triethylamine, tributylamine, diisopropylethylamine, dicyclohexylamine, N-methylpiperidine, pyridine, 4-pyrrolidinopyridine, picoline, 4-(N,N-dimethylamino)pyridine, 2,6-di(tert-butyl)-4-methylpyridine, quinoline, N,N-dimethylaniline, N,N-diethylaniline, 1,5-diazabicyclo[4.3.0]non-5-ene, 1,4-diazabicyclo[2.2.2]octane (DABCO) or 1,8-diazabicyclo[5.4.0]undec-7-ene (DBU); or an organometallic base such as butyllithium, lithium diisopropylamide or lithium bis(trimethylsilyl)anide.

The reaction temperature is usually between –20° C. and 120° C., preferably between 0° C. and 80° C.

The reaction time is from 0.5 to 10 hours.

In esterification method (2):

This process is accomplished by treatment with a condensation reagent in the presence or absence of a base in an ineret solvent.

The condensation reagent is described below:

(a) a combination of a phosphoric ester derivative such as diethylphosphoryl cyanide or diphenylphosphoryl azide and a base described below, (b) a carbodiumide derivative such as 1,3-dicyclohexylcarbodiimide, 1,3-diisopropylcarbodiimide, or 1-ethyl-3-(3-dimethylaminopropyl)carbodiimide,
a combination of a carbodiimide derivative described above and a base described below,
a combination of a carbodiimide derivative described above and an N-hydroxy derivative such as N-hydroxysuccinimide, 1-hydroxybenzotriazole or N-hydroxy-5-norbomen-2,3-dicarboxyimide, (c) a combination of a disulfide derivative such as 2,2'-dipyridyl disulfide, or 2,2'-dibenzothiazolyl disulfide and a phosphine derivative such as triphenylphosphine or tributylphosphine, (d) a carbonate derivative such as N,N'-disuccinimidyl carbonate, di-2-pyridyl carbonate or S,S'-bis(1-phenyl-1H-tetrazol-5-yl)dithiocarbonate, (e) a phosphinic chloride derivative such as N,N'-bis(2-oxo-3-oxazolidinyl)phosphinic chloride, (f) an oxalate derivative such as N,N'-disuccinimidyl oxalate, N,N'-diphthalimide oxalate, N,N'-bis(5-norbornen-2,3-dicarboimidyl) oxalate, 1,1'-bis(benzotriazolyl) oxalate, 1,1'-bis(6-chlorobenzotriazolyl) oxalate, or 1,1'-bis(6-trifluoromethylbenzotnazolyl) oxalate, (g) a combination of a phosphine derivative described above and an ester or amide derivative of azodicarboxylic acid such as diethyl azodicarboxylate, or 1,1'-(azodicarbonyl)dipiperidine,
a combimanation of a phosphine derivative described above and a base described below, (h) an N-lower alkyl-5-arylisooxazolium-3'-sulfonate derivative such as N-ethyl-5-phenylisooxazolium-3'-sulfonate, (i) a diheteroaryl diselenide such as di-2-pyridyl diselenide, (j) an arylsulfonyl triazolide derivative such as p-nitrobenzenesulfonyltriazolide, (k) a 2-halo-1-lower alkylpyridinium halide such as 2-chloro-1-methylpyridinium iodide, (l) an imidazole derivative such as 1,1'-oxalyldiimidazole or N,N'-carbonyldiimidazole, (m) a 3-lower alkyl-2-halo-benzothiazolium fluoroborate derivative such as 3-ethyl-2-chloro-benzothiazolium fluoroborate, (o) a phosphate derivative such as phenyl dichlorophosphate, or polyphosphate ester, (p) a halogenosulfonyl isocyanate derivative such as chlorosulfonyl isocyanate, (q) a halogenosilane derivative such as trimethylsilyl chloride or triethylsilyl chloride, (r) a combination of a lower alkanesulfonyl halide derivative such as methanesulfonyl chloride and a base described below, (s) an N,N,N',N'-tetra lower alkyl halogeno formamidium chloride derivative such as N,N,N',N'-tetramethyl chloroformamidium chloride.

A preferred condensation reagent is a carbodiimide derivative, a combination of a phosphine derivative and an ester derivative of azodicarboxylic acid or a combination of a phosphine derivative and an amide derivative of azodicarboxylic acid.

In esterification method (2) there is no particular restriction of the solvent provided that it has no adverse effect on the reaction and can dissolve the starting material to some extent. A preferred solvent is an aliphatic hydrocarbon drivative such as hexane or heptane, an aromatic hydrocarbon derivative such as benzene, toluene or xylene, a halogeno hydrocarbon derivative such as methylene chloride, chloroform, carbon tetrachloride, dichloroethane, chlorobenzene or dichlorobenzene, an ester derivative such as ethyl formate, ethyl acetate, propyl acetate, butyl acetate or diethyl carbonate, an ether derivative such as diethyl ether, diisopropyl ether, tetrahydrofuran, dioxane, dimethoxyethane, or di(ethylene glycol) dimethyl ether, a nitrile derivative such as acetonitrile or isobutyronitrile, or an amide derivative such as fornamide, N,N-dimethylformamide, N,N-dimethylacetamide, N-methyl-2-pyrrolidone, N-methylpyrrolidinone or hexamethylphosphoric triamide.

In the esterification method (2) a base may be used as a catalyst. There is no particular restriction of the base provided that it can be used as a base in a conventional reaction. A preferred base is an organic base such as N-methylmorpholine, triethylamine, tributylamine, diisopropylethylamine, dicyclohexylamine, N-methylpiperidine, pyridine, 4-pyrrolidinopyridine, picoline, 4-(N,N-dimethylamino)pyridine, 2,6-di(tert-butyl)-4-methylpyridine, quinoline, N,N-dimethylaniline or N,N-diethylaniline.

In addition, in esterification method (2):
a combination of a catalytic amount of 4-(N,N-dimethylamino)pyridine or 4-pyrrolidinopyridine and another base can also be used,
a dehydrating agent such as molecular sieves can be used in order to conduct the esterification effectively,
a quaternary ammonium salt such as benzyltriethylammonium chloride or tetrabutylammonium chloride, a crown ether derivative such as dibenzo-18-crown-6, or an acid capturing agent such as 3,4-dihydro-2H-pyrido[1,2-a]pyrimidin-2-one can be added to the reaction mixture.

The reaction temperature is between −20° C. and 80° C., preferably between 0° C. and room temperature.

The reaction time varies dependent on the reaction temperature, the starting material, the reagent and the solvent. It is usually from 10 minutes to 3 days, preferably 30 minutes to 1 day.

Particularly in the case that the ester-forming group is a lower alkyl group, the esterification reaction is accomplished by treatment with an alcohol such as methanol, ethanol, propanol, or butanol in the presence of an acid catalyst in a solvent.

There is no particular restriction of the solvent provided that it has no adverse effect on the reaction and can dissolve the starting material to some extent. A preferred solvent is an alcohol derivative which is the same as esterifying reagent alcohol, an aliphatic hydrocarbon derivative such as hexane or heptane, an aromatic hydrocarbon derivative such as benzene, toluene or xylene, a halogeno hydrocarbon derivative such as methylene chloride, chloroform, carbon tetrachloride, dichloroethane, chlorobenzene or dichlorobenzene, an ether derivative such as diethyl ether, diisopropyl ether, tetrahydrofuran, dioxane, dimethoxyethane, or di(ethylene glycol) dimethyl ether, a ketone derivative such as acetone, methyl ethyl ketone, methyl isobutyl ketone, isophorone or cyclohexanone, a nitrile derivative such as acetonitrile or isobutyronitrile, or an amide derivative such as formamide, N,N-dimethylformamide, N,N-dimethylacetamide, N-methyl-2-pyrrolidone, N-methylpyrrolidinone or hexamethylphosphoric triamide; a more preferred solvent is an alcohol derivative which is the same as esterifying reagent alcohol.

There is no particular restriction of the acid catalyst provided that it can be used as an acid catalyst in a conventional reaction. A preferred acid is a Bronsted acid, for example an inorganic acid such as hydrochloric acid, hydrobromic acid, sulfuric acid, perchloric acid or phosphoric acid, or an organic acid such as acetic acid, formic acid, oxalic acid, methanesulfonic acid, p-toluenesulfonic acid, trifluoroacetic acid, trifluoromethanesulfonic acid, or a Lewis acid such as boron trichloride, boron trifluoride or boron tribromide, or an acidic ion exchange resin.

The reaction temperature is between 0° C. and 100° C., preferably between 20° C. and 60° C.

The reaction time is from 1 to 24 hours.

After the reaction the desired product (I) is isolated by conventional procedures. For example the reaction mixture is appropriately neutralized, if necessary insoluble material is removed by filtration and is then partitioned between an organic solvent such as ethyl acetate and water. The organic layer is separated, washed with water, dried over anhydrous magnesium sulfate or the like and then is concentrated in vacuo to afford the desired product which, if desired, is further purified by conventional procedures, for example recrystallization, reprecipitation, or a conventional purification procedure.

A conventional purification procedure includes absorption column chromatography using a carrier such as silica gel, alumina, magnesium-silica gel system fluorisil, partition column chromatography using a carrier, for example a synthetic absorbent such as sephadex LH-20 (Pharmacia Co., Ltd), amberlite XAD-11 (Rohm and Haas Co., Ltd) or diaion HP-20 (Mitsubishi Chemicals Co., Ltd) or normal-phase or reverse-phase column chromatography using silica gel or alkylated silica gel (preferably high performance liquid chromatography) or a combination of these chromatographies using an appropriate eluant.

The compound (I) of the invention can be administered by a variety of routes including orally as a unit dosage such as tablets, capsules, granules, powders or syrups, or parenteral administration as a unit dosage such as injections or suppositories. These pharmaceutical formulations are prepared by well known methods using carriers which include additives such as excipients, binders, disintegrants, lubricants, stabilizers, corrigents and diluents.

The determination of a therapeutically effective amount and a prophylactically effective amount can be readily made by the physician or veterinarian (the "attending clinician"), as one skilled in the art, by the use of known techniques and by observing results obtained under analogous circumstances. The dosages may be varied depending upon the requirements of the patient in the judgment of the attending clinician, the severity of the condition being treated and the particular compound being employed. In determining the therapeutically effective amount or dose, and the prophylactically effective amount or dose, a number of factors are considered by the attending clinician, including, but not limited to: the specific condition involved; pharmacodynamic characteristics of the particular agent and its mode and route of administration; the desired time course of treatment; the species of mammal; its size, age, and general health; the specific disease involved; the degree of or involvement or the severity of the disease; the response of the individual patient; the particular compound administered; the mode of administration; the bioavailability characteristics of the preparation administered; the dose regimen selected; the kind of concurrent treatment (i.e., the interaction of the present invention compounds with other co-administered therapeutics); and other relevant circumstances.

Treatment can be initiated with smaller dosages which are less than the optimum dose of the compound. Thereafter, the dosage may be increased by small increments until the optimum effect under the circumstances is reached. For convenience, the total daily dosage may be divided and administered in portions during the day if desired. A therapeutically effective prophylactical amount of a is expected to vary from about 0.1 milligram per kilogram of body weight per day (mg/kg/day) to about 50 mg/kg/day.

Compounds which are determined to be effective for the prevention or treatment of animals, e.g., dogs, rodents, may also be useful in treatment in humans. Those skilled in the art will know, based upon the data obtained in animal studies, the initial dosage and route of administration of the compound to humans. In general, the determination of dosage and route of administration in humans is expected to be similar to that used to determine administration in animals.

The identification of those patients who are in need of prophylactic treatment is well within the ability and knowledge of one skilled in the art, for example, a clinician skilled in the art, by the use of, for example, clinical tests, physical examination and medical/family history.

The present invention provides pharmaceutically acceptable compositions which comprise a therapeutically-effective amount of one or more of the inventive compounds formulated together with one or more pharmaceutically acceptable carriers including additives and/or diluents. As described in detail below, the pharmaceutical compositions of the present invention may be formulated for administration in solid or liquid form, including those adapted for the following: (1) oral administration, for example, drenches (aqueous or non-aqueous solutions or suspensions), tablets, boluses, powders, granules, pastes; (2) parenteral administration, for example, by subcutaneous, intramuscular or intravenous injection as, for example, a sterile solution or suspension; (3) topical application, for example, as a cream, ointment or spray applied to the skin; (4) intravaginally or intrarectally, for example, as a pessary, cream or foam; or (5) aerosol, for example, as an aqueous aerosol, liposomal preparation or solid particles containing the compound.

The phrase "therapeutically-effective amount" as used herein means that amount of compound or composition comprising the compound which is effective for producing some desired macrophage inhibiting effect at a reasonable benefit/risk ratio applicable to any medical treatment.

The phrase "pharmaceutically acceptable" is employed herein to refer to those materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, solvent or encapsulating material, involved in carrying or transporting the subject chemical from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediarnine tetraacetic acid (EDTA), sorbitol, tartaric acid, phosphoric acid, and the like.

Formulations useful in the methods of the present invention include those suitable for oral, nasal, topical (including buccal and sublingual), rectal, vaginal, aerosol and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect.

Generally, out of one hundred percent, this amount will range from about 0.1 percent to about ninety-nine percent of active ingredient, preferably 0.5 percent to 90 percent, more preferably from about 5 percent to about 70 percent, and most preferably from about 10 percent to about 30 percent.

Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of the compound. A compound may also be administered as a bolus, electuary or paste.

In solid dosage forms for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered peptide or peptidomimetic moistened with an inert liquid diluent.

Tablets, and other solid dosage forms, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofiryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing one or more inventive compounds with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active agent.

Formulations which are suitable for vaginal administration also include pessaries, tampons, creams, gels, pastes, foams or spray formulations containing such carriers as are known in the art to be appropriate.

Dosage forms for the topical or transdermal administration include powders, sprays, ointments, pastes, creams, lotions, gels, solutions, patches and inhalants. The active component may be mixed under sterile conditions with a pharmaceutically-acceptable carrier, and with any preservatives, buffers, or propellants which may be required.

The ointments, pastes, creams and gels may contain excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

The compound can be alternatively administered by aerosol. This is accomplished by preparing an aqueous aerosol, liposomal preparation or solid particles containing the compound. A nonaqueous suspension could be used. Sonic nebulizers are preferred because they minimize exposing the agent to shear, which can result in degradation of the compound.

Ordinarily, an aqueous aerosol is made by formulating an aqueous solution or suspension of the agent together with conventional pharmaceutically acceptable carriers including stabilizers. These vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Transdermal patches have the added advantage of providing controlled delivery of a compound to the body. Such dosage forms can be made by dissolving or dispersing the agent in the proper medium. Absorption enhancers can also be used to increase the flux of the peptidomimetic across the skin. The rate of such flux can be controlled by either providing a rate controlling membrane or dispersing the peptidomimetic in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the inventive compound in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

The preparations of agents may be given orally, parenterally, topically, or rectally. They are of course given by forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administration is preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration other than directly into the central nervous system, such that it enters the patient's system and, thus, is subject to metabolism and other like processes, for example, subcutaneous administration.

These inventive compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

These pharmaceutical preparations are prepared by standard techniques that are well known to those skilled in the art using additives. The additives are excipients (for example, organic excipients such as sugar derivatives, e.g. lactose, sucrose, glucose, mannitol and sorbitol; starch derivatives such as corn starch, potato starch, alpha.-starch, dextrin and carboxymethyl starch; cellulose derivatives such as crystalline cellulose, low substituted hydroxyproyl cellulose, hydroxypropylmethyl cellulose, carboxymethyl cellulose, calcium carboxymethyl cellulose and internally bridged sodium carboxymethyl cellulose; gum Arabic; dextran; and Pullulan; and inorganic excipients such as silicate derivatives, e.g. light silicic acid anhydride, synthetic aluminum silicate and magnesium meta-silicic acid aluminate; phosphates, e.g. calcium phosphate; carbonates, e.g. calcium carbonate; and sulfates, e.g. calcium sulfate); lubricants (for example, stearic acid; metal salts of stearic acid such as calcium stearate and magnesium stearate; talc; colloidal silica; waxes such as beeswax and spermaceti; boric acid; adipic acid; sulfates such as sodium sulfate; glycol; fumaric acid; sodium benzoate; DL leucine; sodium salts of aliphatic acid; laurylsulfates such as sodium laurylsulfate and magnesium laurylsulfate; silicic acids such as silicic acid anhydride and silicic acid hydrate; and the above-mentioned starch derivatives); binders (for example, polyvinyl pyrrolidone, Macrogol and the same compounds as described in the above excipients); disintegrants (for example, the same compounds as described in the above excipients; and chemically modified starches and celluloses such as sodium Crosscarmelose, sodium carboxymethyl starch and bridged polyvinyl pyrrolidone); stabilizers (for example, para-oxybenzoates such as methylparaben and propylparaben; alcohols such as chlorobutanol, benzyl alcohol and phenylethyl alcohol; benzalkonium chloride; phenols such as phenol and cresol; thimerosal; dehydroacetic acid; and sorbic acid); corrigents (for example, sweetening agents, acidifiers and aroma chemicals conventionally used); and diluents.

The dosage of compound (I) of the invention depends on the age and condition of the patient (e.g., human). A suitable dosage level for macrophage activity is 0.01 to 50 mg/kg body weight/day. The dosage may be divided into subunits administered at several times throughout the day. A suitable dosage level for inhibition of macrophage activity is 0.01 to 10 mg/kg body weight/day. The dosage may be divided into subunits administered at several times throughout the day.

The following examples, reference examples and test examples are intended to further illustrate the present invention.

BEST MODE FOR CARRYING OUT THE INVENTION

EXAMPLE 1

2,6-Anhydro-7-O-[2-acetylamino-2-deoxy-4-O-phosphono-3-O-{(R)-3-tetradecanoyloxytetradecyl}-D-glucopyranosyl]-3-{(R)-3-hydroxytetradecanoylamino}-4-O-{(R)-3-hydroxytetradecyl}-3-deoxy-D-glycero-D-ido-heptonic Acid (Exemplification Compound Number 57)

A mixture of the compound of Reference Example 24 (3.5 mg, 0.00233 mmol) and platinum oxide (3.1 mg) in tetrahydrofuran (1 ml) was vigorously stirred under a hydrogen atmosphere at room temperature for 18 hours. The reaction mixture was filtered through Celite and the filtrate was concentrated under reduced pressure. The residue was dissolved in a mixture of chloroform (4 ml), methanol (4 ml) and aqueous hydrochloric acid (0.1M, 3.2 ml) and then chloroform (4 ml) was added to the mixture. This mixture was washed with aqueous hydrochloric acid (0.1M, 4 ml) to remove silica gel in the solution. The chloroform layer was separated and concentrated under reduced pressure to afford the title compound (3.0 mg, yield 95%).

IR spectrum ($CDCl_3$): 3353, 1713, 1657, 1604 $cm^{-1}$; NMR spectrum (400 MHz, $CDCl_3$) δ: 0.89 (12H, t, J=6.6–7.3 Hz), 1.28–1.75 (86H, m), 2.01 (3H, s), 2.28–2.42 (4H, m), 3.31–4.53 (20H, m), 4.99 (1H, m); Mass spectrum (m/z): 1351.9468 $(M+H)^+$

EXAMPLE 2

2,6-Anhydro-7-O-[2-acetylamino-2-deoxy-6-O-methyl-4-O-phosphono-3-O-{(R)-3-tetradecanoyloxytetradecyl}-β-D-glucopyranosyl]-3-{(R)-3-hydroxytetradecanoylamino}-4-O-{(R)-3-hydroxytetradecyl }-3-deoxy-D-glycero-D-ido-heptonic Acid (Exemplification Compound Number 13)

A compound from Reference Example 35 (40.8 mg, 0.0269 mmol) was treated in a similar procedure to that described in Example 1 to afford the title compound (35.4 mg, yield 96%).

IR spectrum (KBr): 3315, 2924, 2854, 1730, 1646 cm$^{-1}$; NMR spectrum (400 MHz, CDCl$_3$:CD$_3$OD=1:1) δ: 0.89 (12H, t, J=6.6–7.3 Hz), 1.23–1.85 (86H, m), 2.01 (3H, s), 2.29–2.42 (4H, m), 3.41 (3H, s), 3.48–3.92 (15H, m), 4.02–4.14 (2H, m), 4.28 (1H, dd, J=5.1, 9.5 Hz), 4.50 (1H, d, J=5.1 Hz), 4.62 (1H, d, J=8.8 Hz), 4.95 (1H, m); Analyses for: C$_{72}$H$_{137}$N$_2$O$_{19}$P (Molecular weight:1365.83); Calculated: C, 63.32; H, 10.11; N, 2.05; P, 2.27. Found: C, 62.80; H, 9.94; N, 2.15; P, 2.22.

EXAMPLE 3

2,6-Anhydro-7-O-[2-acetylamino-2,6-dideoxy-6-fluoro-4-O-phosphono-3-O-{(R)-3-tetradecanoyloxytetradecyl}-β-D-glucopyranosyl]-3-{(R)-3-hydroxytetradecanoylamino}-4-O-{(R)-3-hydroxytetradecyl}-3-deoxy-D-glycero-D-ido-heptonic Acid (Exemplification Compound Number 150)

The compound of Reference Example 41 (45.3 mg, 0.0301 mmol) was treated in similar procedure to that described in Example 1 to afford the title compound (40.1 mg, yield 98%) as a white solid.

IR spectrum (KBr): 3304, 2924, 2854, 1730, 1648, 1546 cm$^{-1}$; NMR spectrum (400 MHz, CDCl$_3$:CD$_3$OD=1:1) δ: 0.89 (12H, t, J=6.6 Hz), 1.18–1.83 (86H, m), 2.01 (3H, s), 2.30–2.42 (4H, m), 3.48–3.92 (16H, m), 4.04–4.14 (2H, m 4.27 (1H, m), 4.50 (1H, d, J=5.1 Hz), 4.65–4.69 (2H, m), 4.96 (1H, m); Analyses for: C$_{71}$H$_{134}$N$_2$O$_{18}$PF (Molecular weight:1353.80); Calculated: C, 62.99; H, 9.98; N, 2.07; P, 2.29; F, 1.40. Found: C, 61.77; H, 9.72; N, 2.05; P, 2.38; F, 1.30.

EXAMPLE 4

2,6-Anhydro-7-O-[2-acetylamino-2-deoxy-3-O-{(R)-3-dodecyloxytetradecyl}-4-O-phosphono-β-D-glucopyranosyl]-3-{(R)-3-hydroxytetradecanoylamino}-4-O-{(R)-3-hydroxytetradecyl}-3-deoxy-D-glycero-D-ido-heptonic Acid (Exemplification Compound Number 327)

The mixture of the compound of Reference Example 61 (56.4 mg, 0.0386 mmol) and platinum oxide (55.6 mg) in tetrahydrofuran (3 ml) was stirred under a hydrogen atmosphere at room temperature for 5 hours. The reaction mixture was filtered and the filtrate was concentrated under reduced pressure. The residue was dissolved in a mixture of chloroform (5 ml), methanol (10 ml) and aqueous hydrochloric acid (0.1 N, 4 ml) and then chloroform (5 ml) was added to the mixture. This mixture was washed with aqueous hydrochloric acid (0.1 N, 5 ml). The chloroform layer was separated and concentrated under reduced pressure to afford the title compound (48.3 mg, yield 96%) as a white solid. mp: 179.0–181.0° C.

Optical rotation: $[\alpha]_D^{24}$ –25.5° (c=0.78, CHCl$_3$);

IR spectrum (KBr): 3294 (broad), 3040, 2924, 2854, 1723, 1627 cm$^{-1}$; NMR spectrum (400 MHz, CD$_3$OD:CDCl$_3$=5:1) δ: 4.59 (1H, d, J=8.1 Hz), 4.49 (1H, d, J=5.1 Hz), 4.23 (1H, dd, J=5.1, 9.5 Hz), 4.14–4.03 (2H, m), 3.93–3.74 (8H, m), 3.70–3.52 (5H, m), 3.49–3.40 (5H, m), 2.38 (1H, dd, J=4.4, 14.6 Hz), 2.32 (1H, dd, J=8.1, 14.6 Hz), 2.00 (3H, s), 1.73–1.71 (4H, m), 1.60–1.29 (80H, m), 0.89 (12H, t, J=6.6 Hz). Analyses for: C$_{69}$H$_{133}$N$_2$O$_{18}$P (Molecular weight: 1309.8); Calculated: C, 63.27; H, 10.24; N, 2.14; P, 2.37. Found: C, 62.72; H, 10.21; N, 2.04; P, 1.98.

EXAMPLE 5

2,6-Anhydro-7-O-[2-acetylamino-2-deoxy-3-O-{(R)-3-dodecyloxytetradecyl}-6-O-methyl-4-O-phosphono-β-D-glucopyranosyl]-3-{(R)-hydroxytetradecanoylamino}-4-O-{(R)-3-hydroxytetradecyl}-3-deoxy-D-glycero-D-ido-heptonic Acid (Exemplification Compound Number 287)

The compound of Reference Example 62 (95.4 mg, 0.0646 mmol) was treated in a similar procedure to that described in Example 4 to afford the title compound (85.4 mg, quantitative yield) as a white solid. mp: 181.0–183.0° C.

Optical rotation: $[\alpha]_D^{24}$ –28.6° (c=0.45, CHCl$_3$);

IR spectrum (KBr): 3304 (broad), 3078, 2956, 2923, 2854, 1733, 1654 cm$^{-1}$; NMR spectrum (400 MHz, CDCl$_3$:CD$_3$OD=1:5) δ: 4.59 (1H, d, J=8.1 Hz), 4.50 (1H, d, J=5.1 Hz), 4.24 (1H, dd, J=5.1, 9.5 Hz), 4.09 (1H, q, J=9.5 Hz), 4.04–3.35 (19H, m), 3.40 (3H, s), 2.39 (1H, dd, J=4.4, 14.6 Hz), 2.32 (1H, dd, J=8.1, 14.6 Hz), 2.00 (3H, s), 1.75–1.72 (4H, m), 1.59–1.29 (80H, m), 0.89 (12H, t, J=6.6 Hz); Mass spectrum (m/z): 1345.9336 (M+Na)$^+$; Analyses for: C$_{70}$H$_{135}$N$_2$O$_{18}$P (Molecular weight: 1323.8); Calculated: C, 63.51; H, 10.28; N, 2.12; P, 2.34. Found: C, 63.23; H, 10.14; N, 1.94; P, 2.05.

EXAMPLE 6

2,6-Anhydro-7-O-[2-acetylamino-2,6-dideoxy-3-O-{(R)-3-dodecyloxytetradecyl}-6-fluoro-4-O-phosphono-β-D-glucopyranosyl]-3-{(R)-hydroxytetradecanoylamino}-4-O-{(R)-3-hydroxytetradecyl}-3-deoxy-D-glycero-D-ido-heptonic Acid (Exemplification Compound Number 391)

The compound of Reference Example 63 (46.5 mg, 0.0318 mmol) was treated in a similar procedure to that described in Example 4 to afford the title compound (39.3 mg, yield 94%) as a white solid. mp: 199.0–200.5° C.;

Optical rotation: $[\alpha]_D^{24}$ –34.5° (c=0.70, CHCl$_3$);

IR spectrum (KBr): 3399 (broad), 3306, 3085, 2957, 2923, 2854, 1733, 1645 cm$^{-1}$; NMR spectrum (400 MHz, CDCl$_3$:CD$_3$OD=1:5) δ: 4.80–4.54 (3H, m, containing 1H, d, J=8.1 Hz, δ4.63), 4.49 (1H, d, J=5.1 Hz), 4.23 (1H, dd, J=5.1, 9.5 Hz), 4.11 (1H, q, J=9.5 Hz), 4.06–3.55 (13H, m), 3.49–3.40 (4H, m), 2.38 (1H, dd, J=4.4, 14.6 Hz), 2.33 (1H, dd, J=8.1, 14.6 Hz), 2.00 (3H, s), 1.77–1.69 (4H, m), 1.60–1.29 (80H, m), 0.89 (12H, t, J=6.6 Hz); Mass spectrum (m/z): 1333.9158 (M+Na)$^+$; Analyses for: C$_{69}$H$_{132}$FN$_2$O$_{17}$P (Molecular weight: 1311.8); Calculated: C$_{63.31}$; H, 10.18; N, 2.06; F, 1.45; P, 2.36. Found: C, 63.31; H, 10.18; N, 2.06; F, 1.46 P, 2.08.

REFERENCE EXAMPLE 1

Allyl 2-Azido-2-deoxy-4,6-O-isopropylidene-β-D-glucopyranoside

To a solution of starting material, allyl 2-amino-2-deoxy-4,6-O-isopropylidene-β-D-glucopyranoside (6.35 g, 24.5 mmol) in methanol (120 ml) was added 4-dimethylaminopyridine (3.07 g, 25.1 mmol) and a solution of trifluoromethanesulfonyl azide (0.4 N, 48 mmol) in methylene chloride (120 ml). The mixture was stirred at room temperature for 18 hours and concentrated under reduced pressure. The residue was purified by chromatography on a silica gel column using cyclohexane:ethyl acetate=3:2 as the eluant to give the desired product (6.33 g, yield 91%) as a white solid. mp: 67° C.;

IR spectrum (film): 3452, 2996, 2887, 2113 cm$^{-1}$; NMR spectrum (400 MHz, CD$_3$OD) δ: 1.37 (3H, s), 1.51 (3H, s), 3.21–3.26 (2H, m), 3.40 (1H, t, J=9.5 Hz), 3.53 (1H, t, J=9.2 Hz), 3.78 (1H, t, J=10.6 Hz), 3.86 (1H, dd, J=5.5, 10.6 Hz), 4.09–4.16 (1H, m), 4.31–4.36 (1H, m), 4.45 (1H, d, J=7.3 Hz), 5.17–5.35 (2H, m), 5.93 (1H, m); Mass spectrum (m/z): 286.1413 (M+H)$^+$; Analyses for: C$_{12}$H$_{19}$N$_3$O$_5$ (Molecular weight: 285.3); Calculated: C, 50.52; H, 6.71; N, 14.73. Found: C, 49.44; H, 6.62; N, 14.81.

REFERENCE EXAMPLE 2

Allyl 2-Azido-3-O-{(R)-3-benzyloxytetradecyl}-2-deoxy-4,6-O-isopropylidene-β-D-glucopyranoside To a solution of the azide derivative from Reference Example 1 (4.52 g, 15.8 mmol) in dimethylformamide (60 ml) was added sodium hydride (55% dispersion in mineral oil, <22.0 mmol) at 0° C. and stirred at the same temperature for 15 minutes. (R)-3-Benzyloxy-1-methanesulfonyloxytetradecane (5.74 g,14.4 mmol) was added to the mixture and then stirred at room temperature for 20 hours. Water was added in order to quench the reaction and the reaction mixture was extracted with ethyl acetate. The organic layer was washed with water and then with saturated aqueous sodium chloride solution, dried over magnesium sulfate and concentrated under reduced pressure. The residue was purified by chromatography on a silica gel column using cyclohexane:ethyl acetate=4:1 as the eluant to give the desired product (6.23 g, yield 74%).

IR spectrum (CHCl$_3$): 2928, 2856, 2114 cm$^{-1}$; NMR spectrum (270 MHz, CDCl$_3$) δ: 0.88 (3H, t, J=6.6 Hz), 1.26–1.62 (26H, m, containing 3H, s, at 1.39 ppm, 3H, s, at 1.47 ppm), 1.70–1.84 (2H, m), 3.13–3.23 (2H, m), 3.33 (1H, t, J=8.0, 9.6 Hz), 3.53–3.63 (2H, m), 3.72–3.81 (2H, m), 3.82–395 (2H, m), 4.13 (1H, dd, J=6.1, 12.7 Hz), 4.31–4.39 (2H, m, containing 1H, d, J=8.0 Hz, at 4.32 ppm), 4.53 (2H, s), 5.22–5.38 (2H, m), 5.94 (1H, m), 7.25–7.45 (5H, m); Mass spectrum (m/z): 588.4023 (M+H)$^+$; Analyses for: C$_{33}$H$_{53}$N$_3$O$_6$ (Molecular weight: 587.8); Calculated: C, 67.43; H, 9.09; N, 7.15. Found: C, 67.33; H, 8.99; N, 7.31.

REFERENCE EXAMPLE 3

2-Azido-3-O-{(R)-3-benzyloxytetradecyl}-2-deoxy-4,6-O-isopropylidene-D-glucopyranose To a solution of the 1-allyl derivative from Reference Example 2 (6.15 g, 10.5 mmol) in tetrahydrofuran (120 ml) was added (1,5-cyclooctadiene)bis(methyldiphenylphosphine)iridium hexafluorophosphate (450 mg). The air in the vessel of the mixture was substituted with hydrogen. After the resulting red solution was clear, the hydrogen was substituted with nitrogen and then the mixture was stirred at room temperature for 3 hours. To this mixture was added water (45 ml), pyridine (4.5 ml) and iodine (2.3 g) and the mixture was stirred at room temperature for 12 hours. The reaction mixture was concentrated under reduced pressure and diluted with ethyl acetate. The ethyl acetate layer was successively washed with aqueous sodium thiosulfate solution (10%), saturated aqueous sodium hydrogencarbonate solution, and saturated aqueous sodium chloride solution and dried over anhydrous sodium sulfate and then concentrated under reduced pressure. The residue was purified by chromatography on a silica gel column using cyclohexane:ethyl acetate=3:1 as the eluant to give the desired product (3.71 g, yield 65%, mixture of α and β (1:1)).

IR spectrum (CHCl$_3$): 2928, 2855, 2114 cm$^{-1}$; NMR spectrum (270 MHz, CDCl$_3$) δ: 0.88 (3H, t, J=6.6 Hz), 1.26–1.60 (26H, m, containing 1.5H, s, at 1.39 ppm, 1.5H, s, at 1.40 ppm, 3H, s, at 1.48 ppm), 1.71–1.90 (2H, m), 2.93 (0.5H, broad, OH), 3.18–3.27 (1.5H, m, containing 0.5H, OH), 3.30–3.99 (8H, m), 4.46–4.60 (2.5H, m, containing 2H, s, at 4.52 ppm), 5.23 (0.5H, d, J=3.3 Hz), 7.22–7.37 (5H, m); Mass spectrum (m/z): 548.3638 (M+H)$^+$;

Analyses for: C$_{33}$H$_{53}$N$_3$O$_6$ (Molecular weight: 547.7); Calculated: C, 65.79; H, 9.02; N, 7.67. Found: C, 65.20; H, 9.06; N, 7.52.

REFERENCE EXAMPLE 4

2,2,2-trichloroethylimidoyl 2-azido-3-O-{(R)-3-benzyloxytetradecyl}-2-deoxy-4,6-O-isopropylidene-α-D-glucopyranoside To a solution of the compound from Reference Example 3 (3.66 g, 6.70 mmol) and trichloroacetonitrile (6.8 ml, 67.8 mmol) in methylene chloride (20 ml) was added 1,8-diazabicyclo[5.4.0]undec-7-ene (104 mg, 0.683 mmol) at 0° C. After the mixture was stirred for 2 hours, the reaction was quenched with saturated aqueous ammonium chloride. The reaction mixture was diluted with ethyl acetate. The ethyl acetate layer was successively washed with water and saturated aqueous sodium chloride solution and dried over magnesium sulfate and then concentrated under reduced pressure. The residue was purified by chromatography on a silica gel column using cyclohexane:ethyl acetate=4:1 as the eluant to give the desired product (4.08 g, yield 88%).

IR spectrum (CHCl$_3$): 2116, 1676, 1603 cm$^{-1}$; NMR spectrum (270 MHz, CDCl$_3$) δ: 0.88 (3H, t, J=6.6 Hz), 1.26–1.65 (26H, m, containing 3H, s, at 1.41 ppm, 3H, s, at 1.50 ppm), 1.73–1.95 (2H, m), 3.52–4.07 (9H, m), 4,53 (2H, s), 6.31 (1H, d, J=3.8 Hz), 7.25–7.35 (5H, m), 8.70 (1H, s, NH); Mass spectrum (m/z): 713.2606 (M+Na)$^+$; Analyses for: C$_{33}$H$_{53}$N$_3$O$_6$ (Molecular weight: 692.1); Calculated: C, 55.53; H, 7.14; N, 8.10; Cl, 15.37. Found: C, 55.53; H, 6.78; N, 7.93; Cl, 15.45.

REFERENCE EXAMPLE 5

2,6-Anhydro-3-azido-4-O-{(R)-3-benzyloxytetradecyl}-3-deoxy-5,7-O-isopropylidene-D-glycero-D-ido-heptononitrile A suspension of the compound of Reference Example 4 (4.05 g, 5.85 mmol), well-dried molecular sieves 4A and trimethylsilyl cyanide (1.2 ml, 9.0 mmol) in methylene chloride (30 ml) was stirred under a nitrogen atmosphere at room temperature for 2 hours. After removal of water in the reaction system, trimethylsilyl triflate (40 mg) was added to the mixture and this mixture was stirred at room temperature for 2 hours. The reaction was quenched with saturated aqueous sodium hydrogencarbonate solution. The reaction mixture was filtrated and the filtrate was diluted with ethyl acetate. The ethyl acetate layer was successively washed with water and saturated aqueous sodium chloride solution, dried over magnesium sulfate and then concentrated under reduced pressure. The residue was purified by chromatography on a silica gel column using cyclohexane:ethyl acetate=4:1 as the eluant to give the desired product (3.04 g, yield 93%).

IR spectrum (CHCl$_3$): 2928, 2856, 2119 cm$^{-1}$; NMR spectrum (270 MHz, CDCl$_3$) δ: 0.88 (3H, t, J=6.6 Hz), 1.26–1.58 (26H, m, containing 3H, s, at 1.41 ppm, 3H, s, at 1.47 ppm), 1.70–1.91 (2H, m), 3.52–4.05 (9H, m), 4.54, 4.48 (2H, ABq, J=11.6 Hz), 4.78 (1H, d, J=5.4 Hz), 7.24–7.36 (5H, m); Mass spectrum (m/z): 579.3505 (M+Na)$^+$; Analyses for: C$_{31}$H$_{48}$N$_4$O$_5$ (Molecular weight: 556.7); Calculated: C, 66.88; H, 8.69; N, 10.06. Found: C, 66.79; H, 8.91; N, 10.00.

REFERENCE EXAMPLE 6

2-Amino-2,6-anhydro-4-O-{(R)-3-benzyloxytetradecyl}-3-deoxy-5,7-O-isopropylidene-D-glycero-D-ido-heptononitrile Triphenylphosphine (1.49 g, 5.68 mmol) was added to a solution of the compound of Reference Example 5 (3.02 g, 5.42 mmol) in tetrahydrofuran (30 ml) at 0° C. and the mixture was stirred at the same temperature for 1 hour. Aqueous ammonia solution (28%, 15 ml) was added to the mixture and this mixture was stirred at 60° C. for 20 hours. The reaction mixture was diluted with ethyl acetate. The ethyl acetate layer was successively washed with water and saturated aqueous sodium chloride solution and dried over magnesium sulfate and then concentrated under reduced pressure. The residue was purified by chromatography on a silica gel column using cyclohexane:ethyl acetate=9:1, 3:2 as the eluant to give the desired product (2.03 g, yield 71%).

IR spectrum (CHCl$_3$): 3691, 2928, 2856, 1602 cm$^{-1}$; NMR spectrum (400 MHz, CDCl$_3$) δ: 0.88 (3H, t, J=6.9 Hz), 1.26–1.65 (28H, m, containing 3H, s, at 1.40 ppm, 3H, s, at 1.46 ppm), 2.95 (1H, dd, J=6.0, 9.7 Hz), 3.22 (1H, t, J=9.2 Hz), 3.50–3.56 (2H, m), 3.65–3.76 (3H, m), 3.91 (1H, m), 3.99 (1H, m), 4.46, 4.55 (2H, ABq, J=11.7 Hz), 4.74 (1H, d, J=6.0 Hz), 7.26–7.36 (5H, m); Mass spectrum (m/z): 553.3603 (M+Na)$^+$; Analyses for: C$_{31}$H$_{50}$N$_2$O$_5$ (Molecular weight: 530.7); Calculated: C, 70.15; H, 9.50; N, 5.28. Found: C, 69.72; H, 9.47; N, 4.52.

REFERENCE EXAMPLE 7

2,6-Anhydro-3-{(R)-3-benzyloxytetradecanoylamino}-4-O-{(R)-3-benzyloxytetradecyl}-3-deoxy-5,7-O-isopropylidene-D-glycero-D-ido-heptononitrile Dicyclohexylcarbodiimide (963 mg, 4.67 mmol), 4-dimethylaminopyridine (574 mg, 4.70 mmol) and (R)-3-benzyloxytetradecanoic acid (1.50 g, 4.48 mmol) were added to a solution of the compound of Reference Example 5 (1.96 g, 3.71 mmol) in methylene chloride (30 ml) and the mixture was stirred at room temperature for 18 hours. Dicyclohexylurea produced during the reaction was removed by filtration and the filtrate was concentrated under reduced pressure. The residue was diluted with ethyl acetate. The ethyl acetate layer was successively washed with saturated aqueous sodium hydrogencarbonate solution and saturated aqueous sodium chloride solution, dried over magnesium sulfate and then concentrated under reduced pressure. The residue was purified by chromatography on a silica gel column using cyclohexane:ethyl acetate 4:1 as the eluant to give the desired product (2.79 g, yield 89%).

IR spectrum (CHCl$_3$): 3691, 2928, 2855, 1672, 1603 cm$^{-1}$; NMR spectrum (270 MHz, CDCl$_3$) δ: 0.88 (3H, t, J=6.6 Hz), 1.25–1.77 (48H, m, containing 3H, s, at 1.39 ppm, 3H, s, at 1.44 ppm), 2.35 (1H, dd, J=6.5, 15.5 Hz), 2.54 (1H, dd, J=3.6, 15.5 Hz), 3.21–3.30 (2H, m), 3.40 (1H, m), 3.56–3.81 (5H, m), 3.86–4.03 (2H, m), 4.40, 4.45 (2H, ABq, J=1 1.7 Hz), 4.55 (2H, s), 5.25 (1H, d, J=6.0 Hz), 7.10 (1H, d, J=5.5 Hz, NH), 7.25–7.40 (10H, m); Mass spectrum (m/z): 847.6199 (M+H)$^+$; Analyses for: C$_{52}$H$_{82}$N$_2$O$_7$ (Molecular weight: 847.2); Calculated: C, 73.72; H, 9.76; N, 3.31. Found: C, 73.50; H, 9.82; N, 3.55.

REFERENCE EXAMPLE 8

Diphenylmethyl 2,6-Anhydro-3-{(R)-3-benzyloxytetradecanoylamino}-4-O-{(R)-3-benzyloxytetradecyl}-3-deoxy-D-glycero-D-ido-heptonate Hydrochloric acid-dioxane (4M, 15 ml) and water (3 ml) was added to the compound of Reference Example 7 (2.70 g, 3.19 mmol) and the mixture was stirred at 80° C. for 72 hours. The reaction mixture was concentrated under reduced pressure to dryness. To a solution of the residue in dimethylformamide (15 ml) was added diphenyldiazomethane (1.87 g, 9.63 mmol) and the mixture was stirred at 60° C. for 2 hours. The reaction was quenched by the addition of water. The reaction mixture was extracted with ethyl acetate. The ethyl acetate layer was successively washed with saturated aqueous sodium hydrogencarbonate solution and saturated aqueous sodium chloride solution, dried over magnesium sulfate and then concentrated under reduced pressure. The residue was purified by chromatography on a silica gel column using cyclohexane:ethyl acetate=1:1 as the eluant to give the desired product (1.35 g, yield 43%).

IR spectrum (CHCl$_3$): 3691, 2928, 2855, 1672, 1603 cm$^{-1}$; NMR spectrum (270 MHz, CDCl$_3$) δ: 0.88 (6H, t, J=6.5 Hz), 1.25–1.71 (42H, m), 1.95 (1H, broad, OH), 2.29 (2H, d, J=5.3 Hz), 3.30 (1H, broad, OH), 3.35–3.74 (10H, m), 4.32, 4.38 (2H, ABq, J=11.3 Hz), 4.43 (2H, s), 4.62 (1H, d, J=5.6 Hz), 6.84 (1H, s), 6.87 (1H, d, J=8.8 Hz, NH), 7.23–7.33 (20H, m); Mass spectrum (m/z): 992.6610 (M+H)$^+$; Analyses for: C$_{52}$H$_{82}$N$_2$O$_7$ (Molecular weight: 992.4); Calculated: C, 75.04; H, 9.04; N, 1.41. Found: C, 74.62; H, 8.94; N, 1.43.

REFERENCE EXAMPLE 9

2-(4-Methoxyphenyl)-4-(R)-undecyl-[1,3]dioxane p-Toluenesulfonic acid (152 mg, 0.80 mmol) and 4-methoxybenzaldehyde dimethylacetal (2.9 g, 16.0 mmol) was added to a solution of (R)-1,3-dihydroxytetradecane (1.85 g, 8.0 mnuol) in dimethylformamide (20 ml) and the mixture was stirred at room temperature for 2 hours. The reaction mixture was concentrated under reduced pressure. The residue was diluted with ethyl acetate. The ethyl acetate layer was successively washed with saturated aqueous sodium hydrogencarbonate solution and saturated aqueous sodium chloride solution, dried over magnesium sulfate and then concentrated under reduced pressure. The residue was purified by chromatography on a silica gel column using cyclohexane:ethyl acetate=9:1 as the eluant to give the desired product (2.78 g, yield 99%).

IR spectrum (CHCl$_3$): 2928, 2856,1616, 1518 cm$^{-1}$; NMR spectrum (270 MHz, CDCl$_3$) δ: 0.88 (3H, t, J=6.5 Hz), 1.19–1.56 (20H, m), 1.60–1.81 (2H, m), 3.75–3.82 (4H, m, containing 3H, s, at 3.80 ppm), 3.94 (1H, m), 4.24 (1H, m), 5.46 (1H, s), 6.89 (2H, d, J=8.6 Hz), 7.42 (2H, d, J=8.7 Hz); Mass spectrum (m/z): 349.2751 (M+H)$^+$; Analyses for: C$_{22}$H$_{36}$O$_3$ (Molecular weight: 348.52); Calculated: C, 75.82; H, 10.41. Found: C, 75.60; H, 10.68.

REFERENCE EXAMPLE 10

(R)-3-(4-Methoxybenzyloxy)-1-hydroxytetradecane

A solution of diisobutylaluminium hydride (1M, 24 ml, 24 mmol) in methylene chloride was added to a solution of the compound of Reference Example 9 (2.71 g, 7.80 mmol) in methylene chloride (25 ml) and the mixture was stirred at −78° C. under a nitrogen atmosphere for 2 hours. The reaction was quenched with saturated aqueous ammonium chloride solution. To the mixture was added aqueous potassium tartrate solution and this mixture was stirred at room temperature for 30 minutes. The organic layer was separated and was successively washed with water and saturated aqueous sodium chloride solution, dried over magnesium sulfate and then concentrated under reduced pressure. The residue was purified by chromatography on a silica gel column using cyclohexane:ethyl acetate 7:3 as the eluant to give the desired product (2.54 g, yield 93%).

IR spectrum (CHCl$_3$): 3626, 3499, 2929, 2857, 1613, 1514 cm$^{-1}$; NMR spectrum (270 MHz, CDCl$_3$) δ: 0.88 (3H, t, J=6.6 Hz), 1.27–1.84 (22H, m), 2.44 (1H, t, J=5.4 Hz, OH), 3.62 (1H, m), 3.69–3.82 (5H, m, containing 3H, at 3.80 ppm), 4.41, 4.54 (2H, ABq, J=11.1 Hz), 6.88 (2H, d, J=8.6 Hz), 7.26 (2H, d, J=8.6 Hz); Mass spectrum (m/z): 350.2800 (M$^+$); Analyses for: C$_{22}$H$_{38}$O$_3$ (Molecular weight: 350.54); Calculated: C, 74.77; H, 11.10. Found: C, 75.38; H, 10.93.

REFERENCE EXAMPLE 11

(R)-3-(4-Methoxybenzyloxy)-1-methanesulfonyloxytetradecane

Triethylamine (1.5 ml, 10.7 mmol) and methanesulfonyl chloride (1.22 g, 10.7 mmol) were added to a solution of the compound of Reference Example 10 (2.50 g, 7.10 mmol) in methylene chloride (20 ml) at 0° C. and the mixture was stirred for 1 hour. The reaction mixture was concentrated under reduced pressure. The residue was diluted with ethyl acetate. The ethyl acetate layer was successively washed with water, saturated aqueous sodium hydrogencarbonate solution and saturated aqueous sodium chloride solution, dried over magnesium sulfate and then concentrated under reduced pressure. The residue was purified by chromatography on a silica gel column using cyclohexane:ethyl acetate=7:3 as the eluant to give the desired product (3.02 g, yield 99%).

IR spectrum (CHCl$_3$): 2929, 2857, 1613 cm$^{-1}$; NMR spectrum (270 MHz, CDCl$_3$) δ: 0.88 (3H, t, J=6.6 Hz), 1.27 (18H, brs), 1.43–1.66 (2H, m), 1.81–1.98 (2H, m), 2.95 (3H, s), 3.54 (1H, m), 3.80 (3H, s), 4.26–4.51 (4H, m, containing 2H, ABq, J=11.0 Hz, at 4.38, 4.51 ppm), 6.88 (2H, d, J=8.7 Hz), 7.26 (2H, d, J=8.6 Hz); Mass spectrum (m/z): 428.2584 (M$^+$); Analyses for: C$_{23}$H$_{40}$O$_5$S (Molecular weight: 428.63); Calculated: C, 64.45; H, 9.41; S, 7.48. Found: C, 63.99; H, 9.53; S, 7.57.

REFERENCE EXAMPLE 12

Allyl 2-Deoxy-4,6-isopropylidene-3-O-{(R)-3-(4-methoxybenzyloxy)tetradecyl}-2-trifluoroacetylamino-α-D-glucopyranoside Sodium hydride (55% dispersion in mineral oil, 205 mg) was added to a solution of starting material, allyl 2-deoxy-4,6-O-isopropylidene-2-trifluoroacetylamino-α-D-glucopyranoside (1.28 g, 3.60 mmol) in dimethylformamide (15 ml) at 0° C. and the mixture was stirred for 15 minutes. (R)-3-(4-Methoxybenzyloxy)-1-methanesulfonyloxytetradecane from Reference Example 11 (1.29 g, 3.00 mmol) was added to the mixture and this mixture was then stirred at room temperature for 18 hours. The reaction was quenched by addition of water to the reaction mixture. The mixture was extracted with ethyl acetate. The ethyl acetate layer was successively washed with water and saturated aqueous sodium chloride solution, dried over magnesium sulfate and then concentrated under reduced pressure. The residue was purified by chromatography on a silica gel using cyclohexane:ethyl acetate=3:1 as the eluant to give the desired product (1.74 g, yield 84%).

IR spectrum (CHCl$_3$): 3429, 2929, 2857, 1734 cm$^{-1}$; NMR spectrum (270 MHz, CDCl$_3$) δ: 0.88 (3H, t, J=6.5 Hz), 1.26–1.49 (26H, m, containing 3H, s, at 1.40 ppm, 3H, s, at 1.49 ppm), 1.64–1.78 (2H, m), 3.41–3.91 (11H, m, containing 3H, s, at 3.80 ppm), 3.99 (1H, m), 4.13–4.21 (2H, m), 4.36–4.43 (2H, ABq, J=11.2 Hz), 4.87 (1H, d, J=3.8 Hz), 5.24–5.32 (2H, m), 5.87 (1H, m), 6.41 (1H, d, J=9.3 Hz, NH), 6.87 (2H, d, J=8.6 Hz), 7.25 (2H, d, J=7.9 Hz); Mass spectrum (m/z): 710.3851 (M+Na)$^+$; Analyses for: C$_{36}$H$_{56}$F$_3$NO$_8$ (Molecular weight: 687.84); Calculated: C, 62.86; H, 8.21; N, 2.04; F, 8.29. Found: C, 62.36; H, 8.15; N, 2.07; F, 7.94.

REFERENCE EXAMPLE 13

Allyl 2-Amino-2-deoxy-4,6-O-isopropylidene-3-O-{(R)-3-(4-methoxybenzyloxy)tetradecyl}-β-D-glucopyranoside A solution of the compound of Reference Example 12 (1.45 g, 2.11 mmol) in ethanol (10 ml) and aqueous sodium hydroxide solution (1N, 10 ml) and the mixture was stirred at 60° C. for 3 hours. The reaction mixture was concentrated under reduced pressure. The residue was diluted with ethyl acetate. The ethyl acetate layer was successively washed with water and saturated aqueous sodium chloride solution, dried over sodium sulfate and then concentrated under reduced pressure. The residue was purified by chromatography on a silica gel column using cyclohexane:ethyl acetate=2:3 as the eluant to give the desired product (1.23 g, yield 99%).

IR spectrum (CHCl$_3$): 2928, 2855, 1612 cm$^{-1}$; NMR spectrum (270 MHz, CDCl$_3$) δ: 0.88 (3H, t, J=6.6 Hz), 1.26–1.62 (28H, m, containing 3H, s, at 1.39 ppm, 3H, s, at 1.48 ppm), 1.71–1.85 (2H, m), 2.72 (1H, dd, J=3.7, 9.5 Hz), 3.27 (1H, t, J=9.1 Hz), 3.49–3.86 (9H, m, containing 3H, s, at 3.80 ppm), 4.17 (1H, m), 4.40, 4.47 (2H, ABq, J=11.2 Hz), 4.86 (1H, d, J=3.6 Hz), 5.19–5.34 (2H, m), 5.88 (1H, m), 6.87 (2H, d, J=8.6 Hz), 7.26 (2H, d, J=8.6 Hz); Mass spectrum (m/z): 592.4207 (M+H)$^+$; Analyses for: C$_{34}$H$_{57}$NO$_7$ (Molecular weight: 591.83); Calculated: C, 69.00; H, 9.71; N, 2.37. Found: C, 68.16; H, 10.21; N, 2.31.

REFERENCE EXAMPLE 14

Allyl 2-Deoxy-4,6-O-isopropylidene-3-O-{(R)-3-(4-methoxybenzyloxy)tetradecyl}-2-(2,2,2-trichloroethoxycarbonylamino)-α-D-glucopyranoside A mixture of a solution of the compound of Reference Example 13 (1.20 g, 2.03 mmol) in methylene chloride (8 ml), saturated aqueous sodium hydrogencarbonate solution (8 ml) and 2,2,2-trichloroethyl chloroformate (543 mg, 2.52 mmol) was stirred at room temperature for 30 minutes. The reaction mixture was diluted with ethyl acetate. The ethyl acetate layer was successively washed with water and saturated aqueous sodium chloride solution, dried over magnesium sulfate and then concentrated under reduced pressure. The residue was purified by chromatography on a silica gel column using cyclohexane:ethyl acetate=4:1 as the eluant to give the desired product (1.47 g, yield 94%).

IR spectrum (CHCl$_3$): 3440, 2929, 2857, 1744, 1613 cm$^{-1}$; NMR spectrum (270 MHz, CDCl$_3$) δ: 0.88 (3H, t, J=6.6 Hz), 1.26–1.48 (26H, m, containing 3H, s, at 1.40 ppm, 3H, s, at 1.48 ppm), 1.62–1.78 (2H, m), 3.38–4.02 (13H, m, containing 3H, s, at 3.80 ppm), 4.16 (1H, m), 4.39, 4.45 (2H, ABq, J=11.2 Hz), 4.68, 4.74 (2H, ABq, J=12.0 Hz), 4.86 (1H, d, J=3.7 Hz), 5.13–5.32 (3H, m), 5.89 (1H, m), 6.88 (2H, d, J=8.6 Hz), 7.27 (2H, d, J=8.5 Hz); Mass spectrum (m/z): 788.3077 (M+Na)$^+$; Analyses for: C$_{37}$H$_{58}$NO$_9$Cl$_3$ (Molecular weight: 767.22); Calculated: C, 57.92; H, 7.62; N, 1.83; Cl, 13.86. Found: C, 57.40; H, 7.38; N, 1.85; Cl, 13.87.

REFERENCE EXAMPLE 15

Allyl 2-Deoxy-3-O-{(R)-3-(4-methoxybenzyloxy)tetradecyl}-2-(2,2,2-trichloroethoxycarbonylamino)-α-D-glucopyranoside A solution of the compound of Reference Example 14 (885 mg, 1.15 mmol) in aqueous acetic acid solution (80%) was stirred at 60° C. for 1 hour. The reaction mixture was concentrated under reduced pressure. The residue was diluted with ethyl acetate. The ethyl acetate layer was successively washed with saturated aqueous sodium hydrogencarbonate solution and saturated aqueous sodium chloride solution, dried over magnesium sulfate and then concentrated under reduced pressure. The residue was purified by chromatography on a silica gel column using cyclohexane:ethyl acetate=2:3 as the eluant to give the desired product (696 mg, yield 83%).

IR spectrum (CHCl$_3$): 3601, 3436, 2928, 1742, 1612 cm$^{-1}$; NMR spectrum (270 MHz, CDCl$_3$) δ: 0.88 (3H, t, J=6.6 Hz), 1.26 (18H, brs), 1.43–1.80 (4H, m), 2.08 (1H, broad, OH), 3.41–3.54 (4H, m), 3.56–3.91 (9H, m, containing 3H, s, at 3.81 ppm), 3.99 (1H, dd, J=6.3, 12.8 Hz), 4.18 (1H, dd, J=5.3, 12.8 Hz), 4.39, 4.45 (2H, ABq, J=11.2 Hz), 4.68, 4.75 (2H, ABq, J=12.0 Hz), 4.85 (1H, d, J=3.5 Hz), 5.21–5.32 (3H, m), 5.89 (1H, m), 6.88 (2H, d, J=8.8 Hz), 7.26 (2H, d, J=8.5 Hz); Mass spectrum (m/z): 748.2744 (M+Na)$^+$; Analyses for: C$_{34}$H$_{54}$NO$_9$Cl$_3$ (Molecular weight: 727.15); Calculated: C, 56.16; H, 7.49; N, 1.93; Cl, 14.63. Found: C, 56.10; H, 7.36; N, 1.96; Cl, 14.60.

REFERENCE EXAMPLE 16

Allyl 6-O-Benzyloxycarbonyl-2-deoxy-3-O-{(R)-3-(4-methoxybenzyloxy)tetradecyl}-2-(2,2,2-trichloroethoxycarbonylamino)-α-D-glucopyranoside Pyridine (60.4 mg, 0.764 mmol) and benzyloxycarbonyl chloride (90 μl, 0.630 mmol) was added to a solution of the compound of Reference Example 15 (366 mg, 0.503 mmol) in methylene chloride (5 ml) at 0° C. and the mixture was stirred at the same temperature for 30 minutes and then stirred at room temperature for 2 hours. The reaction mixture was was diluted with ethyl acetate. The ethyl acetate layer was successively washed with aqueous ammonium chloride solution (1N), saturated aqueous sodium hydrogencarbonate solution and saturated aqueous sodium chloride solution, dried over magnesium sulfate and then concentrated under reduced pressure. The residue was purified by chromatography on a silica gel column using cyclohexane:ethyl acetate=3:1 as the eluant to give the desired product (419 mg, yield 97%).

IR spectrum (CHCl$_3$): 3436, 2928, 2856, 1744, 1612 cm$^{-1}$; NMR spectrum (270 MHz, CDCl$_3$) δ: 0.88 (3H, t, J=6.6 Hz), 1.26–1.78 (22H, m), 3.37–3.53 (4H, m, containing OH), 3.69–3.99 (8H, m, containing 3H, s, at 3.79 ppm), 4.15 (1H, dd, J=5.3, 13.0 Hz), 4.37–4.47 (4H, m), 4.67, 4.74 (2H, ABq, J=12.1 Hz), 4.84 (1H, d, J=3.7 Hz), 5.18–5.30 (5H, m), 5.87 (1H, m), 6.87 (2H, d, J=8.6 Hz), 7.25 (2H, d, J=7.3 Hz), 7.33–7.41 (5H, m); Mass spectrum (m/z): 858.3133 (M−H)$^+$; Analyses for: C$_{42}$H$_{60}$NO$_{11}$Cl$_3$ (Molecular weight: 861.28); Calculated: C, 58.57; H, 7.02; N, 1.63; Cl, 12.35. Found: C, 58.38; H, 6.93; N, 1.61; Cl, 12.58.

REFERENCE EXAMPLE 17

Allyl 6-O-Benzyloxycarbonyl-2-deoxy-4-O-diphenylphosphono-3-O-{(R)-3-(4-methoxybenzyloxy)tetradecyl}-2-(2,2,2-trichloroethoxycarbonylamino)-α-D-glucopyranoside 4-Dimethylaminopyridine (83.7 mg, 0.679 mmol) and diphenylphosphinoyl chloride (140 μl, 0.675 mmol) was added to a solution of the compound of Reference Example 16 (390 mg, 0.453 mmol) in methylene chloride (3 ml) and the mixture was stirred at room temperature for 1 hour. The reaction mixture was was diluted with ethyl acetate. The ethyl acetate layer was successively washed with saturated aqueous sodium hydrogencarbonate solution and saturated aqueous sodium chloride solution, dried over magnesium sulfate and then concentrated under reduced pressure. The residue was purified by chromatography on a silica gel column using cyclohexane:ethyl acetate 3:1 as the eluant to give the desired product (467 mg, yield 94%).

IR spectrum (CHCl$_3$): 3435, 2928. 2855, 1747, 1612 cm$^{-1}$; NMR spectrum (270 MHz, CDCl$_3$) δ: 0.88 (3H, t, J=6.6 Hz), 1.17–1.72 (22H, m), 3.37 (1H, m), 3.65–3.84 (6H, m, containing 3H, s, at 3.78 ppm), 3.93–4.04 (3H, m), 4.14 (1H, dd, J=5.3, 12,9 Hz), 4.20–4.39 (4H, m), 4.63 (1H, m), 4.49, 4.76 (2H, ABq, J=12.1 Hz), 4.87 (1H, d, J=3.6 Hz), 5.06, 5.12 (2H, ABq, J=12.2 Hz), 5.21–5.30 (3H, m), 5.86 (1H, m), 6.83 (2H, d, J=8.6 Hz), 7.11–7.37 (17H, m); Mass spectrum (m/z): 1090.3431 (M−H)$^+$; Analyses for: C$_{54}$H$_{69}$NO$_{14}$PCl$_3$ (Molecular weight: 1093.47); Calculated: C, 59.32; H, 6.36; N, 1.28; P, 2.83; Cl, 9.73. Found: C, 59.35; H, 6.35; N, 1.21; P, 3.04; Cl, 9.80.

REFERENCE EXAMPLE 18

Allyl 6-O-Benzyloxycarbonyl-2-deoxy-4-O-diphenylphosphono-3-O-{(R)-3-hydroxytetradecyl}-2-(2,2,2-trichloroethoxycarbonylamino)-α-D-glucopyranoside Water (0.3 ml) and 2,3-dichloro-5,6-dicyano-1,4-benzoquinone (84.6 mg, 0.373 mmol) was added to a solution of the compound of Reference Example 17 (338 mg, 0.309 mmol) in methylene chloride (3 ml) and the mixture was stirred at room temperature for 1 hour. The reaction mixture was was diluted with ethyl acetate. The ethyl acetate layer was successively washed with saturated aqueous sodium hydrogencarbonate solution and saturated aqueous sodium chloride solution, dried over magnesium sulfate and then concentrated under reduced pressure. The residue was purified by chromatography on a silica gel column using cyclohexane:ethyl acetate=7:3 as the eluant to give the desired product (283 mg, yield 94%).

IR spectrum (CHCl$_3$): 3435, 2927, 2855, 1746, 1592 cm$^{-1}$; NMR spectrum (270 MHz, CDCl$_3$) δ: 0.88 (3H, t, J=6.6 Hz), 1.25–1.75 (22H, m), 3.64–3.85 (4H, m), 3.95–4.08 (3H, m), 4.15 (1H, dd, J=5.3, 12.7 Hz), 4.23–4.38 (2H, m), 4.63–4.75 (3H, m), 4.93 (1H, d, J=3.6 Hz), 5.04, 5.11 (2H, ABq, J=12.2 Hz), 5.22–5.31 (2H, m), 5.44 (1H, d, J=9.2 Hz, NH), 5.88 (1H, m), 7.11–7.34 (15H, m); Mass spectrum (m/z): 972.3010 (M+H)$^+$; Analyses for: $C_{46}H_6NO_{13}PCl_3$ (Molecular weight: 973.31); Calculated: C, 56.77; H, 6.32; N, 1.44; P, 3.18; Cl, 10.93. Found: C, 56.60; H, 6.49; N, 1.45; P, 3.33; Cl, 11.17.

REFERENCE EXAMPLE 19

Allyl 6-O-Benzyloxycarbonyl-2-deoxy-4-O-diphenylphosphono-3-O-{(R)-3-tetradecanoyloxytetradecyl}-2-(2,2,2-trichloroethoxycarbonylamino)-α-D-glucopyranoside Triethylamine (60 μl, 0.427 mmol), 4-dimethylaminopyridine (51.3 mg, 0.420 mmol) and myristoyl chloride (0.12 ml, 0.438 mmol) was added to a solution of the compound of Reference Example 18 (271 mg, 0.278 mmol) in tetrahydrofuran (3 ml) and the mixture was stirred at room temperature for 18 hours. The reaction mixture was was diluted with ethyl acetate. The ethyl acetate layer was successively washed with saturated aqueous sodium hydrogencarbonate solution and saturated aqueous sodium chloride solution, dried over magnesium sulfate and then concentrated under reduced pressure. The residue was purified by chromatography on a silica gel column using cyclohexane:ethyl acetate=4:1 as the eluant to give the desired product (305 mg, yield 93%).

IR spectrum (CHCl$_3$): 3435, 2927, 2855, 1746, 1592 cm$^{-1}$; NMR spectrum (270 MHz, CDCl$_3$) δ: 0.88 (3H, t, J=6.6 Hz), 1.19–1.71 (44H, m), 2.20 (2H, t, J=7.5 Hz), 3.50 (1H, m), 3.68 (1H, m), 3.82 (1H, m), 3.92–4.01 (3H, 4.15 (1H, dd, J=5.3, 13.0 Hz), 4.28–4.41 (2H, m), 4.63 (1H, m), 4.75 (2H, s), 4.84–4.93 (2H, m, containing 1H, d, J=3.6 Hz, at 4.90 ppm), 5.05, 5.11 (2H, ABq, J=12.2 Hz), 5.20–5.34 (2H, m), 5.78 (1H, d, J=10.7 Hz, NH), 5.87 (1H, m), 7.12–7.34 (15H, m); Mass spectrum (m/z): 1182.5021 (M+H)$^+$; Analyses for: $C_{60}H_{87}NO_{14}PCl_3$ (Molecular weight: 1183.66); Calculated: C, 60.88; H, 7.41; N, 1.18; P, 2.62; Cl, 8.99. Found: C, 61.22; H, 7.46; N, 1.13; P, 2.72; Cl, 9.18.

REFERENCE EXAMPLE 20

6-O-Benzyloxycarbonyl-2-deoxy-4-O-diphenylphosphono-3-O-{(R)-3-tetradecanoyloxytetradecyl}-2-(2,2,2-trichloroethoxycarbonylamino)-β-D-glucopyranose To a solution of the compound of Reference Example 19 (136 mg, 0.114 mmol) in tetrahydrofuran (3 ml) was added (1,5-cyclooctadiene)bis(methyldiphenylphosphine)iridium hexafluorophosphate (3.6 mg). The air in the vessel of the mixture was substituted with hydrogen. After the resulting red solution was clear, the hydrogen was substituted with nitrogen and then the mixture was stirred at room temperature for 2 hours. To this mixture was added water (0.3 ml), pyridine (15 mg) and iodine (22 mg) and the mixture was stirred at room temperature for 1 hour. The reaction mixture was diluted with ethyl acetate. The ethyl acetate was successively washed with aqueous sodium thiosulfate solution (10%), saturated aqueous sodium hydrogencarbonate solution, and saturated aqueous sodium chloride solution, dried over anhydrous sodium sulfate and then concentrated under reduced pressure. The residue was purified by chromatography on a silica gel column using cyclohexane:ethyl acetate=7:3 as the eluant to give the desired product (106 mg, yield 81%).

IR spectrum (CHCl$_3$): 3599, 3434, 3326, 2927, 2855, 1746, 1592 cm$^{-1}$; NMR spectrum (270 MHz, CDCl$_3$) δ: 0.88 (3H, t, J=6.6 Hz), 1.20–1.77 (44H, m), 2.21 (2H, t, J=7.5 Hz), 3.41–3.53 (2H, m, containing OH), 3.75 (1H, m), 3.83–3.95 (2H, m), 4.19–4.43 (3H, m), 4.58–4.79 (3H, m), 4.92 (1H, m), 5.04, 5.11 (2H, ABq, J=12.1 Hz), 5.29 (1H, m), 6.03 (1H, d, J=8.6 Hz, NH), 7.12–7.34 (15H, m) Mass spectrum (m/z): 1164.4518 (M+Na)$^+$; Analyses for: $C_{57}H_{83}NO_{14}PCl_3$ (Molecular weight: 1143.60); Calculated: C, 59.87; H, 7.37; N, 1.23; P, 2.71; Cl, 9.30. Found: C, 59.84; H, 7.29; N, 1.46; P, 2.76; Cl, 9.05.

REFERENCE EXAMPLE 21

2,2,2-Trichloroethylimidoyl 6-O-Benzyloxycarbonyl-2-deoxy-4-O-diphenylphosphono-3-O-{(R)-3-tetradecanoyloxytetradecyl}-2-(2,2,2-trichloroethoxycarbonylamino)-α-D-glucopyranoside To a solution of the 6-O-benzyloxy-2-trichloroethoxycarbonylaminoglucose compound from Reference Example 20 (83.1 mg, 0.0726 mmol) in methylene chloride (2 ml) was added trichloroacetonitrile (80 μl, 0.798 mmol). To the mixture was added 1,8-diazabicyclo[5.4.0]undec-7-ene (DBU, 5 mg, 0.0329 mmol) at 0° C. After stirring the mixture at 0° C. for 1 hour, the excess DBU was quickly removed by chromatography on a short silica gel column using cyclohexane:ethyl acetate=3:1 as the eluant to give the desired product which was used in the next reaction without further purification.

REFERENCE EXAMPLE 22

Diphenylmethyl 2,6-Anhydro-7-O-[6-O-benzyloxycarbonyl-2-deoxy-4-O-diphenylphosphono-3-O-{(R)-3-tetradecanoyloxytetradecyl}-2-(2,2,2-trichloroethoxycarbonylamino)-β-D-glucopyranosyl]-3-{(R)-3-benzyloxytetradecanoylamino}-4-O-{(R)-3-benzyloxytetradecyl}-3-deoxy-D-glycero-D-ido-heptonate To a solution of the compound of Reference Example 21 (54.8 mg) in methylene chloride (3 ml) was added well-dried molecular sieves 4A and the diol compound of Reference Example 8 (35 mg, 0.0353 mmol) and the mixture was stirred at −78° C. To this suspension was added trimethylsilyl trifluoromethanesulfonate (5 μl, 0.0276 mmol). This mixture was stirred for 2 hours. The reaction was quenched with saturated aqueous sodium hydrogencarbonate solution and the reaction mixture was diluted with ethyl acetate. The ethyl acetate layer was washed with water and saturated aqueous sodium chloride solution, dried over magnesium sulfate and concentrated in vacuo. The residue was purified by chromatography on a silica gel column using cyclohexane:ethyl acetate=7:3 as the eluant to give the desired product (65.1 mg, yield 87%).

IR spectrum (CHCl$_3$): 3432, 3354, 2927, 2855, 1739, 1670 cm$^{-1}$; NMR spectrum (400 MHz, CDCl$_3$) δ: 0.88 (12H, t, J=6.5–7.1 Hz), 1.00–1.73 (86H, m), 2.19–2.26 (4H, m), 3.04 (1H, brs, OH), 3.15 (1H, m), 3.38–3.68 (12H, m), 3.85–3.97 (2H, m), 4.20 (1H, dd, J=5.2, 11.9 Hz), 4.27–4.53

(7H, m, containing 1H, d, J=5.5 Hz, at 4.62 ppm), 4.78 (1H, ABq, J=12.1 Hz), 4.94–5.12 (3H, m, containing 2H, ABq, J=12.1 Hz, at 5.04, 5.10 Hz), 5.97 (1H, m, NH), 6.80 (1H, d, J=8.7 Hz, NH), 6.82 (1H, s), 7.12–7.36 (35H, m); Mass spectrum (m/z): 2138.0940 (M+Na)$^+$.

REFERENCE EXAMPLE 23

Diphenylmethyl 2,6-Anhydro-7-O-[2-acetylamino-6-O-benzyloxycarbonyl-2-deoxy-4-O-diphenylphosphono-3-O-{(R)-3-tetradecyloxytetradecyl}-β-D-glucopyranosyl]-3-{(R)-3-benzyloxytetradecanoylamino}-4-O{(R)-3-benzyloxytetradecyl}-3-deoxy-D-glycero-D-ido-heptonate To a solution of the compound of Reference Example 22 (60.8 mg, 0.0287 mmol) in acetic acid (2 ml) was added zinc powder (40.2 mg). The mixture was stirred at room temperature for 24 hours. The reaction mixture was filtered through Celite and the filtrate concentrated in vacuo. The residue was diluted with ethyl acetate. The ethyl acetate layer was washed with saturated aqueous sodium hydrogencarbonate solution and saturated aqueous sodium chloride solution, dried over anhydrous sodium sulfate and concentrated in vacuo. To a solution of the residue in a mixture of tetrahydrofuran (0.4 ml) and water (0.8 ml) was added pyridine (10 μl) and acetic anhydride (10 μl) and this mixture was stirred at room temperature for 4 hours. The reaction mixture was diluted with ethyl acetate. The ethyl acetate layer was washed with water and saturated aqueous sodium chloride solution, dried over magnesium sulfate and concentrated in vacuo. The residue was purified by chromatography on a silica gel column using cyclohexane:ethyl acetate=3:2 as the eluant to give the desired product (40.2 mg, yield 70%, two steps).

IR spectrum (CHCl$_3$): 3432, 3365, 2927, 2855, 1738, 1668 cm$^{-1}$; NMR spectrum (400 MHz, CDCl$_3$) δ: 0.88 (12H, t, J=6.6–7.3 Hz), 1.00–1.76 (86H, m), 1.92 (3H, s), 2.17–2.26 (4H, m), 3.08 (1H, m), 3.33–3.72 (12H, m), 3.89–4.02 (2H, m), 4.21 (1H, dd, J=5.1, 11.9 Hz), 4.28–4.52 (7H, m), 4.63 (1H, d, J=5.7 Hz), 5.02–5.10 (3H, m, containing 2H, ABq, J=12.1 Hz, at 5.03, 5.10 ppm), 5.27 (1H, d, J=8.2 Hz), 6.64 (1H, d, J=6.3 Hz, NH), 6.78 (1H, d, J=8.9 Hz, NH), 6.81 (1H, s), 7.12–7.37 (35H, m); Mass spectrum (m/z): 2006.2009 (M+Na)$^+$.

REFERENCE EXAMPLE 24

2,6-Anhydro-7-O-[2-acetylamino-2-deoxy-4-O-diphenylphosphono-3-O-{(R)-3-tetradecanoyloxytetradecyl}-β-D-glucopyranosyl]-3-{(R)-3-hydroxytetradecanoylamino}-4-O-{(R)-3-hydroxytetradecyl}-3-deoxy-D-glycero-D-ido-heptonic Acid To a solution of the compound of Reference Example 23 (9.1 mg, 0.00459 mmol) in ethyl acetate (0.5 ml) was added palladium hydroxide on carbon (10.4 mg, 20%). The mixture was vigorously stirred under a hydrogen atmosphere at room temperature for 14 hours. The reaction mixture was filtered through Celite and the filtrate was concentrated in vacuo. The residue was purified by chromatography on a silica gel column using chloroform: methanol=8:1 as the eluant and the solvent was evaporated in vacuo from the fractions containing the desired product. The residue was diluted with ethyl acetate. The ethyl acetate layer was washed with aqueous hydrochloric acid solution (0.05M) and saturated aqueous sodium chloride solution, dried over anhydrous sodium sulfate and concentrated in vacuo to give the desired product (4.0 mg, yield 58%).

IR spectrum (CHCl$_3$): 3691, 3606, 3415, 3358, 1716, 1662, 1602 cm$^{-1}$; NMR spectrum (400 MHz, CDCl$_3$) δ: 0.88 (12H, m, J=6.7 Hz), 1.20–1.65 (86H, m), 2.00 (3H, s), 2.23–2.43 (4H, m), 3.38–3.94 (22H, m), 4.05–4.10 (1H, m), 4.38–4.48 (2H, m), 4.65 (1H, m), 4.90 (1H, m), 4.98 (1H, m), 7.19–7.36 (10H, m); Mass spectrum (m/z): 1525.9941 (M+Na)$^+$.

REFERENCE EXAMPLE 25

Allyl 6-O-tert-Butyldimethylsilyl-2-deoxy-3-O-{(R)-3-(4-methoxybenzyloxy)tetradecyl}-2-(2,2,2-trichloroethoxycarbonylamino)-α-D-glucopyranoside To a solution of the compound of Reference Example 15 (1.15 g, 1.58 mmol) in methylene chloride (5 ml) was added 4-dimethylaminopyridine (304 mg, 2.49 mmol) and tert-butyldimethylsilyl chloride (364 mg, 2.42 mmol). The mixture was stirred at room temperature for 3 hours. The reaction mixture was diluted with ethyl acetate. The ethyl acetate layer was successively washed with water, saturated aqueous sodium hydrogencarbonate solution and saturated aqueous sodium chloride solution, dried over magnesium sulfate and then concentrated under reduced pressure. The residue was purified by chromatography on a silica gel column using cyclohexane:ethyl acetate=4:1 as the eluant to give the desired product (1.28 g, yield 96%).

IR spectrum (CHCl$_3$): 3437, 2955, 2929, 2856, 1742, 1613, 1514 cm$^{-1}$; NMR spectrum (270 MHz, CDCl$_3$) δ: 0.087 (6H, s), 0.86–0.91 (12H, m), 1.26 (18H, brs), 1.40–1.80 (4H, m), 3.34–3.67 (4H, m, containing OH), 3.76–3.93 (9H, m, containing 3H, s, at 3.80 ppm), 3.98 (1H, dd, J=6.3, 12.8 Hz), 4.18 (1H, dd, J=5.2, 12.9 Hz), 4.40,4.45 (2H, ABq, J=11.5 Hz), 4.70 (2H, s), 4.84 (1H, d, J=3.6 Hz), 5.19–5.32 (3H, m, containing NH), 5.90 (1H, m), 6.87 (2H, d, J=8.6 Hz), 7.26 (2H, d, J=8.6 Hz); Mass spectrum (m/z): 862.3622 (M+Na)$^+$; Analyses for: C$_{40}$H$_{68}$NO$_9$PSi (Molecular weight: 841.41); Calculated: C, 57.10; H, 8.15; N, 1.67; Cl, 12.64. Found: C, 57.54; H, 8.13; N, 1.57; Cl, 12.72.

REFERENCE EXAMPLE 26

Allyl 6-O-tert-Butyldimethylsilyl-2-deoxy-4-O-diphenylphosphono-3-O-{(R)-3-(4-methoxybenzyloxy)tetradecyl}-2-(2,2,2-trichloroethoxycarbonylamino)-α-D-glucopyranoside To a solution of the compound of Reference Example 25 (1.26 g, 1.50 mmol) in methylene chloride (5 ml) was added 4-dimethylaminopyridine (278 mg, 2.28 mmol) and diphenylphosphinic chloride (0.46 ml, 2.23 mmol). The mixture was stirred at room temperature for 1 hour. The reaction mixture was diluted with ethyl acetate. The ethyl acetate layer was successively washed with saturated aqueous sodium hydrogencarbonate solution and saturated aqueous sodium chloride solution, dried over magnesium sulfate and then concentrated under reduced pressure. The residue was purified by chromatography on a silica gel column using cyclohexane:ethyl acetate=4:1 as the eluant to give the desired product (1.57 g, yield 98%). IR spectrum (CHCl$_3$): 3435, 2955, 2929, 2856, 1743, 1613 cm$^{-1}$ NMR spectrum (270 MHz, CDCl$_3$) δ: 0.002 (6H, s), 0.86–0.92 (12H, m), 1.26 (18H, brs), 1.66–1.74 (4H, m), 3.37 (1H, m), 3.69–3.87 (9H, m, containing 3H, s, at 3.79 ppm) 3.94–4.04 (2H, m), 4.22 (1H, dd, J=5.3, 12.7 Hz), 4.30 (2H, s), 4.43–4.61 (2H, m), 4.75 (1H, m) 4.89 (1H, d, J=3.6 Hz), 5.20–5.34 (3H, m, containing NH), 5.91 (1H, m), 6.84 (2H, d, J=8.6 Hz), 7.14–7.33 (12H, m); Mass spectrum (m/z): 1094.3905 (M+Na)$^+$; Analyses for: $C_{52}H_{77}NO_{12}PCl_3Si$ (Molecular weight: 1073.58); Calculated: C, 58.18; H, 7.23; N, 1.31; P, 2.89; Cl, 9.91. Found: C, 57.85; H, 7.05; N, 1.27; P, 2.16; Cl, 10.57.

REFERENCE EXAMPLE 27

Allyl 6-O-tert-Butyldimethylsilyl-2-deoxy-4-O-diphenylphosphono-3-O-{(R)-3-hydroxtetradecyl}-2-(2,2,2-trichloroethoxycarbonylamino)-α-D-glucopyranoside To a solution of the compound of Reference Example 26 (1.50 g, 1.40 mmol) in methylene chloride (5 ml) was added 2,3-dichloro-5,6-dicyano-1,4-benzoquinone (386 mg, 1.70 mmol) and water (0.5 ml). The mixture was stirred at room temperature for 1 hour. The reaction mixture was diluted with ethyl acetate. The ethyl acetate layer was successively washed with saturated aqueous sodium hydrogencarbonate solution and saturated aqueous sodium chloride solution, dried over magnesium sulfate and then concentrated under reduced pressure. The residue was purified by chromatography on a silica gel column using cyclohexane:ethyl acetate=3:1 as the eluant to give the desired product (1.22 g, yield 91%).

IR spectrum (CHCl$_3$): 3434, 2928, 2856, 1740 cm$^{-1}$; NMR spectrum (270 MHz, CDCl$_3$) δ: 0.002 (6H, s), 0.82–0.90 (12H, m), 1.25–1.67 (22H, m), 3.65–3.87 (8H, m, containing OH), 3.93–4.04 (2H, m), 4.21 (1H, dd, J=5.3, 12.9 Hz), 4.62 (1H, m), 4.75 (2H, s), 4.93 (1H, d, J=3.7 Hz), 5.22–5.34 (2H, m), 5.44 (1H, d, J=9.3 Hz, NH), 5.91 (1H, m), 7.15–7.35 (10H, m); Mass spectrum (m/z): 974.3345 (M+Na)$^+$; Analyses for: $C_{44}H_{69}NO_{11}PCl_3Si$ (Molecular weight: 953.44). Calculated: C, 55.43; H, 7.30; N, 1.47; P, 3.25; Cl, 11.16. Found: C, 56.71; H, 7.51; N, 1.48; P, 2.92; Cl, 11.43.

REFERENCE EXAMPLE 28

Allyl 6-O-tert-Butyldimethylsilyl-2-deoxy-4-O-diphenylphosphono-3-O-{(R)-3-tetradecanoyloxytetradecyl}-2-(2,2,2-trichloroethoxycarbonylamino)-α-D-glucopyranoside To a solution of the compound of Reference Example 27 (1.21 g, 1.27 mmol) in tetrahydrofuran (6 ml) was added triethylamine (0.36 ml, 2.56 mmol), 4-dimethylaminopyridine (326 mg, 2.67 mmol) and myristoyl chloride (0.70ml, 2.55 mmol). The mixture was stirred at room temperature for 24 hours. The reaction mixture was diluted with ethyl acetate. The ethyl acetate layer was successively washed with water, saturated aqueous sodium hydrogencarbonate solution and saturated aqueous sodium chloride solution, dried over magnesium sulfate and then concentrated under reduced pressure. The residue was purified by chromatography on a silica gel column using cyclohexane:ethyl acetate=4:1 as the eluant to give the desired product (1.40 g, yield 95%).

IR spectrum (CHCl$_3$): 3435, 2928, 2856, 1737 cm$^{-1}$; NMR spectrum (270 MHz, CDCl$_3$) δ: 0.013 (6H, δ, 0.86–0.92 (15H, m), 1.26 (40H, brs), 1.53–1.74 (4H, m), 2.18 (2H, t, J=7.3–7.7 Hz), 3.55 (1H, m), 3.67–4.07 (7H, m), 4.22 (1H, dd, J=5.2–12.8 Hz), 4.56 (1H, m), 4.77 (2H, s), 4.83–4.91 (2H, m, containing 1H, d, J=3.6 Hz, at 4.91 ppm), 5.22–5.36 (2H, m), 5.68 (1H, d, J=9.4 Hz, NH), 5.92 (1H, m), 7.15–7.35 (10H, m); Mass spectrum (m/z): 1200.5026 (M+K)$^+$; Analyses for: $C_{58}H_{95}NO_{12}PCl_3Si$ (Molecular weight: 1163.79); Calculated: C, 59.86; H, 8.23; N, 1.20; P, 2.66; Cl, 9.14. Found: C, 61.37; H, 7.89; N, 1.07; P, 1.43; Cl, 8.59.

REFERENCE EXAMPLE 29

Allyl 2-Deoxy-4-O-diphenylphosphono-3-O-{(R)-3-tetradecanoyloxytetradecyl}-2-(2,2,2-trichloroethoxycarbonylamino)-α-D-glucopyranoside To a solution of the compound of Reference Example 28 (1.35 g, 1.16 mmol) in tetrahydrofuran (9 ml) was added aqueous hydrochloric acid solution (1.2 ml, 3N). The mixture was stirred at room temperature for 2 hours. The reaction mixture was diluted with ethyl acetate. The ethyl acetate layer was successively washed with saturated aqueous sodium hydrogencarbonate solution and saturated aqueous sodium chloride solution, dried over magnesium sulfate and then concentrated under reduced pressure. The residue was purified by chromatography on a silica gel column using cyclohexane:ethyl acetate=7:3 as the eluant to give the desired product (1.11 g, yield 91%).

IR spectrum (CHCl$_3$): 3691, 3606, 3437, 2927, 2855, 1737 cm$^{-1}$; NMR spectrum (400 MHz, CDCl$_3$) δ: 0.88 (6H, t, J=6.6 Hz), 1.19–1.73 (44H, m), 2.23 (2H, t, J=7.3–8.1 Hz), 3.52 (1H, m), 3.60–3.70 (4H, m), 3.89–4.03 (3H, m), 4.17 (1H, dd, J=5.1, 12.5 Hz), 4.65 (1H, m), 4.73, 4.78 (2H, ABq, J=12.5 Hz), 4.91–4.95 (2H, m, containing 1H, d, J=3.7 Hz, at 4.95 ppm), 5.23–5.35 (2H, m), 5.82 (1H, d, J=9.5 Hz, NH), 5.89 (1H, m), 7.20–7.38 (10H, m); Mass spectrum (m/z): 1070.4452 (M+Na)$^+$; Analyses for: $C_{52}H_{81}NO_{12}PCl_3$ (Molecular weight: 1049.53); Calculated: C, 59.51; H, 7.78; N, 1.34; P, 2.95; Cl, 10.13. Found: C, 59.30; H, 7.90; N, 1.51; P, 2.94; Cl, 10.24.

REFERENCE EXAMPLE 30

Allyl 2-Deoxy-4-O-diphenylphosphono-6-O-methyl-3-O-{(R)-3-tetradecanoyloxytetradecyl}-2-(2,2,2-trichloroethoxycarbonylamino)-α-D-glucopyranoside To a solution of the compound of Reference Example 29 (1.05 g, 1.00 mmol) in methylene chloride (5 ml) was added 2,6-di-tert-butyl-4-methylpyridine (679 mg, 3.31 mmol) and trimethyloxonium tetrafluoroborate (446 mg, 3.02 mmol). The mixture was stirred at room temperature for 3 hours. The reaction mixture was diluted with methylene chloride. The methylene chloride layer was successively washed with saturated aqueous sodium hydrogencarbonate solution and saturated aqueous sodium chloride solution, dried over magnesium sulfate and then concentrated under reduced pressure. The residue was purified by chromatography on a silica gel column using cyclohexane:ethyl acetate=7:3 as the eluant to give the desired product (966 mg, yield 91%).

IR spectrum (CHCl$_3$): 3691, 3435, 2927, 2855, 1738 cm$^{-1}$; NMR spectrum (400 MHz, CDCl$_3$) δ: 0.88 (6H, t, J=6.6–7.3 Hz), 1.18–1.72 (44H, m), 2.18 (2H, t, J=7.3–8.1 Hz), 3.24 (3H, s), 3.48–3.59 (3H, m), 3.69 (1H, m), 3.82–3.88 (2H, m), 3.96–4.04 (2H, m), 4.20 (1H, dd, J=5.1, 13.2 Hz), 4.64–4.80 (3H, m), 4.88 (1H, m), 4.94 (11H, d, J=3.7 Hz), 5.22–5.35 (2H, m), 5.69 (1H, d, J=8.8 Hz, NH), 5.90 (1H, m), 7.16–7.35 (101H, m); Mass spectrum (m/z): 1084.4600 (M+Na)$^+$; Analyses for: $C_{53}H_{83}NO_{12}PCl_3$ (Molecular weight: 1063.56); Calculated: C, 59.85; H, 7.87; N, 1.32; P, 2.91; Cl, 10.00. Found: C, 60.14; H, 7.59; N, 1.42; P, 2.92; Cl, 10.08.

REFERENCE EXAMPLE 31

2-Deoxy-4-O-diphenylphosphono-6-O-methyl-3-O-{(R)-3-tetradecanoyloxytetradecyl}-2-(2,2,2-trichloroethoxycarbonylamino)-α-D-glucopyranose The compound of Reference Example 30 (478 mg, 0.450 mmol) was treated according to the procedure analogous to Reference Example 20 to give the desired product (334 mg, yield 73%).

IR spectrum (KBr): 3436, 3352, 2953, 2921, 2851, 1726 cm$^{-1}$; NMR spectrum (400 MHz, CDCl$_3$) δ: 0.88 (6H, t, J=6.6–7.3 Hz), 1.19–1.73 (44H, m), 2.19 (2H, t, J=7.3 Hz), 3.22 (3H, s), 3.45–3.56 (3H, m), 3.72–3.94 (4H, m, containing 1OH), 4.13 (1H, m), 4.56 (1H, m), 4.71, 4.77 (2H, ABq, J=12.5 Hz), 4.90 (1H, m), 5.29 (1H, m), 5.88 (1H, d, J=8.8 Hz, NH), 7.17–7.35 (10H, m);

REFERENCE EXAMPLE 32

2,2,2-Trichloroethylimidoyl-2-deoxy-4-O-diphenylphosphono-6-O-methyl-3-O-{(R)-3-tetradecanoyloxytetradecyl}-2-(2,2,2-trichloroethoxycarbonylamino)-α-D-glucopyranoside The compound of Reference Example 31 (279 mg, 0.273 mmol) was treated according to the procedure analogous to Reference Example 21 to give the desired product which was used in the next reaction without further purification.

REFERENCE EXAMPLE 33

Diphenylmethyl 2,6-Anhydro-7-O-[2-deoxy-4-O-diphenylphosphono-6-O-methyl-3-O-{(R)-3-tetradecanoyloxytetradecyl}-2-(2,2,2-trichloroethoxycarbonylamino)-β-D-glucopyranosyl]-3-{(R)-3-benzyloxytetradecanoylamino}-4-O-{(R)-3-benzyloxytetradecyl}-3-deoxy-D-glycero-D-ido-heptonate The compound of Reference Example 32 (275 mg) and the diol compound of Reference Example 8 (180 mg, 0.181 mmol) were treated according to a procedure analogous to Reference Example 22. The reaction product was purified by chromatography on a silica gel column using hexane: ethyl acetate=3:2 as the eluant to afford the desired product (261 mg, yield 72%).

IR spectrum (CHCl$_3$): 3431, 3354, 2927, 2855, 1732, 1669 cm$^{-1}$; NMR spectrum (400 MHz, CDCl$_3$) δ: 0.88 (12H, t, J=6.6 Hz), 1.25–1.76 (86H, m), 2.20–2.25 (4H, m), 3.10 (1H, s, OH), 3.17–3.25 (4H, m, containing 3H, s, at 3.20 ppm), 3.40–3.74 (13H, m), 3.82 (1H, m), 3.98 (1H, m), 4.27–4.37 (3H, m, containing 2H, ABq, J=11.7 Hz, at 4.29, 4.33 ppm), 4.40, 4.44 (2H, ABq, J=11.7 Hz), 4.51 (1H, m), 4.62–4.65 (3H, m, containing 1H, d, J=5.1 Hz, at 4.62 ppm), 4.78 (1H, ABq, J=11.7 Hz), 4.91 (1H, m), 5.01 (1H, m), 5.88 (1H, m, NH), 6.78 (1H, d, J=8.1 Hz, NH), 6.82 (1H, s) 7.17–7.35 (30H, m)

REFERENCE EXAMPLE 34

Diphenylmethyl 2,6-Anhydro-7-O-[2-acetylamino-2-deoxy-4-O-diphenylphosphono-6-O-methyl-3-O-{(R)-3-tetradecanoyloxytetradecyl}-β-D-glucopyranosyl]-3-{(R)-3-benzyloxytetradecanoylamino}-4-O-{(R)-3-benzyloxytetradecyl}-3-deoxy-D-glycero-D-ido-heptonate The compound from Reference Example 33 (135 mg, 0.0676 mmol) was treated according to a procedure analo-gous to Reference Example 23. The reaction product was purified by chromatography on a silica gel column using hexane: ethyl acetate=1:1 as the eluant to afford the desired product (81.4 mg, yield 65%, 2 steps).

IR spectrum (CHCl$_3$): 3693, 3433, 3369, 2927, 2855, 1720, 1669, 1600 cm$^{-1}$; NMR spectrum (400 MHz, CDCl$_3$) δ: 0.88 (12H, t, J=6.6–7.3 Hz), 1.22–1.74 (86H, m), 1.93 (3H, s), 2.20–2.24 (4H, m), 3.18 (1H, m), 3.22 (3H, s), 3.37–3.72 (14H, m, containing OH), 3.89 (1H, mn), 4.02 (1H, m), 4.29–4.38 (3H, m, containing 2H, ABq, J=11.0 Hz, at 4.30, 4.34 ppm), 4.42 (2H, s), 4.50 (1H, m), 4.63 (1H, d, J=5.9 Hz), 5.07 (1H, m), 5.21 (1H, d, J=8.1 Hz), 6.56 (1H, d, J=6.6 Hz, NH), 6.76 (1H, d, J=8.8 Hz, NH), 6.81 (1H, s), 7.17–7.36 (30H, m);

REFERENCE EXAMPLE 35

2,6-Anhydro-7-O-[2-acetylamino-2-deoxy-4-O-diphenylphosphono-6-O-methyl-3-O-{(R)-3-tetradecanoyloxytetradecyl}-β-D-glucopyranosyl]-3-{(R)-3-hydroxytetradecanoylamino}-4-O-{(R)-3-hydroxytetradecyl}-3-deoxy-D-glycero-D-ido-heptonic Acid To a solution of the compound of Reference Example 34 (73.1 mg, 0.0392 mmol) in ethanol (3 ml) was added palladium hydroxide on carbon (58.3 mg, 20%). The mixture was stirred under a hydrogen atmosphere at room temperature for 8 hours. The reaction mixture was filtered through Celite and the filtrate was concentrated in vacuo. The residue was chromatographed on a silica gel column using chloroform: methanol=8:1 and diluted with ethyl acetate. The ethyl acetate layer was washed with aqueous hydrochloric acid (0.05M) and saturated aqueous sodium chloride solution, dried over anhydrous sodium sulfate and then concentrated in vacuo to dryness to give the desired product (42.7 mg, yield 72%).

IR spectrum (KBr): 3321, 2924, 2854, 1731, 1651 cm$^{-1}$; NMR spectrum (400 MHz, CD$_3$OD) δ: 0.90 (12H, t, J=6.6–7.3 Hz), 1.28–1.76 (86H, m), 2.00 (3H, s), 2.19 (2H, t, J=7.3 Hz), 2.34–2.37 (2H, m), 3.21 (3H, s), 3.43–3.48 (3H, m), 3.57–4.01 (13H, m), 4.21 (1H, m), 4.47 (1H, d, J=5.1 Hz), 4.55 (1H, m), 4.64 (1H, d, J=8.1 Hz), 4.83 (1H, m), 7.20–7.41 (10H, m).

REFERENCE EXAMPLE 36

Allyl 2,6-Dideoxy-4-O-diphenylphosphono-6-fluoro-3-O-{(R)-3-tetradecanoyloxytetradecyl }-2-(2,2,2-trichloroethoxycarbonylamino)-α-D-glucopyranoside To a solution of the compound of Reference Example 29 (938 mg, 0.894 mmol) in 1,2-dimethoxyethane (5 ml) was added diethylaminosulfur trifluoride (DAST, 0.35 ml, 2.65 mmol) at 0° C., and the mixture was stirred for 3 hours. The reaction was quenched by the addition of water at 0° C. The reaction mixture was extracted with ethyl acetate three times. The ethyl acetate layer was washed with saturated aqueous sodium hydrogencarbonate solution and saturated aqueous sodium chloride solution, dried over magnesium sulfate and then concentrated in vacuo. The residue was purified by chromatography on a silica gel column using hexane: ethyl acetate=7:3 as the eluant to give the desired product (753 mg, yield 80%).

IR spectrum (CHCl$_3$): 3606, 3435, 2927, 2855, 1738, 1601 cm$^{-1}$; NMR spectrum (400 MHz, CDCl$_3$) δ: 0.88 (6H, t, J=6.6–7.3 Hz), 1.19–1.73 (44H, m), 2.20 (2H, t, J=7.3 Hz), 3.52 (1H, m), 3.71 (1H, t, J=9.5 Hz), 3.81–4.06 (4H, m), 4.20 (1H, m), 4.44–4.65 (3H, m), 4.76 (2H, s), 4.90 (1H, m), 4.95 (1H, d, J=3.7 Hz), 5.23–5.36 (2H, m), 5.78 (1H, d, J=9.5 Hz, NH), 5.90 (1H, m), 7.17–7.35 (10H, m); Mass spectrum (m/z): 1072.4424 (M+Na)$^+$; Analyses for: $C_{52}H_{80}NO_1$ $PFC_{13}$ (Molecular weight: 1051.52); Calculated: C, 59.40; H, 7.67; N, 1.33; P, 2.95; F, 1.81; Cl, 10.12. Found: C, 58.52; H, 7.36; N, 1.55; P, 2.58; F, 2.47; Cl, 9.93.

REFERENCE EXAMPLE 37

2,6-Dideoxy-4-O-diphenylphosphono-6-fluoro-3-O-{(R)-3-tetradecanoyloxytetradecyl}-2-(2,2,2-trichloroethoxycarbonylamino)-α-D-glucopyranose The compound of Reference Example 36 (365 mg, 0.347 mmol) was treated according to a procedure analogous to Reference Example 20 to give the desired product (256 mg, yield 73%).

IR spectrum (CHCl$_3$): 3601, 3434, 3326, 2927, 2855, 1737 cm$^{-1}$; NMR spectrum (400 MHz, CDCl$_3$) δ: 0.88 (6H, t, J=6.6 Hz), 1.20–1.71 (44H, m), 2.22 (2H, t, J=7.3–8.1 Hz), 3.38 (1H, brs, OH), 3.49 (1H, m), 3.76–3.95 (3H, m) 4.17 (1H, m), 4.44–4.65 (3H, m), 4.72–4.77 (2H, ABq, J=12.1 Hz), 4.92 (1H, m) 5.36 (1H, m), 6.07 (1H, d, J=8.8 Hz, NH), 7.18–7.35 (10H, m); Mass spectrum (m/z): 1010.4271 (M+H)$^+$.

REFERENCE EXAMPLE 38

2,2,2-Trichloroethylimidoyl 2,6-dideoxy-4-O-diphenylphosphono-6-fluoro-3-O-{(R)-3-tetradecanoyloxytetradecyl}-2-(2,2,2-trichloroethoxycarbonylamino)-α-D-glucopyranoside The compound of Reference Example 37 (255 mg, 0.252 mmol) was treated according to a procedure analogous to Reference Example 21 to give the desired product which was used in Reference Example 39 without further purification.

REFERENCE EXAMPLE 39

Diphenylmethyl 2,6-Anhydro-7-O-[2,6-dideoxy-4-O-diphenylphosphono-6-fluoro-3-O-{(R)-3-tetradecanoyloxytetradecyl}-2-(2,2,2-trichloroethoxycarbonylamino)-β-D-glucopyranosyl]-3-{(R)-3-benzyloxytetradecanoylamino}-4-O-{(R)-3-benzyloxytetradecyl}-3-deoxy-D-glycero-D-ido-heptonate The compound of Reference Example 39 (283 mg) and the diol compound of Reference Example 8 (201 mg, 0.203 mmol) were treated according to a procedure analogous to Reference Example 22 to give the desired product (307 mg, yield 76%).

IR spectrum (CHCl$_3$): 2927, 2855, 1732, 1670, 1601 cm$^{-1}$; NMR spectrum (400 MHz, CDCl$_3$) δ: 0.88 (12H, t, J=6.6 Hz), 1.25–1.71 (86H, m), 2.21–2.26 (4H, m), 2.97 (1H, s, OH), 3.17 (1H, m), 3.43–4.01 (14H, m), 4.27–4.81 (11H, m, containing 1H, d, J=5.9 Hz, at 4.63 ppm), 5.01 (1H, m), 5.94 (1; H, brs, NH), 6.81 (1H, d, J=11.0 Hz, NH), 6.82 (1H, s), 7.17–7.35 (30H, m); Mass spectrum (m/z): 2006.0531 (M+Na)$^+$.

REFERENCE EXAMPLE 40

Diphenylmethyl 2,6-Anhydro-7-O-[2-acetylamino-2,6-dideoxy-4-O-diphenylphosphono-6-fluoro-3-O-{(R)-3-tetradecanoyloxytetradecyl}-β-D-glucopyranosyl]-3-{(R)-3-benzyloxytetradecanoylamino}-4-O-{(R)-3-benzyloxytetradecyl}-3-deoxy-D-glycero-D-ido-heptonate The compound of Reference Example 39 (152 mg, 0.0767 mmol) was treated according to a procedure analogous to Reference Example 23 to give the desired product (94.2 mg, yield 66%, 2 steps).

IR spectrum (CHCl$_3$): 3432, 3364, 2927, 2855, 1718, 1668, 1600 cm$^{-1}$; NMR spectrum (400 MHz, CDCl$_3$) δ: 0.88 (12H, t, J=6.6 Hz), 1.22–1.73 (86H, m), 2.21–2.24 (4H, m), 3.10 (1H, m), 3.39–3.69 (12H, m, containing OH), 3.93–4.05 (2H, m), 4.28–4.58 (8H, m, containing 2H, ABq, J=11.4 Hz, at 4.30, 4.34 ppm, 2H, s, at 4.43 ppm), 4.63 (1H, d, J=5.9 Hz), 5.07 (1H, m), 5.28 (1H, d, J=8.8 Hz), 6.59 (1H, d, J=6.6 Hz, NH), 6.78 (1H, d, J=8.8 Hz, NH), 6.81 (1H, s), 7.17–7.35 (30H, m); Mass spectrum (m/z): 1874.1609 (M+Na)$^+$;

REFERENCE EXAMPLE 41

2,6-Anhydro-7-O-[2-acetylamino-2,6-dideoxy-4-O-diphenylphosphono-6-fluoro-3-O-{(R)-3-tetradecanoyloxytetradecyl}-β-D-glucopyranosyl]-3-{(R)-3-hydroxytetradecanoylamino}-4-O-{(R)-3-hydroxytetradecyl}-3-deoxy-D-glycero-D-ido-heptonic Acid The compound from Reference Example 40 (90.3 mg, 0.0487 mmol) was treated according to a procedure analogous to Reference Example 35 to give the desired product (47.1 mg, yield 64%).

IR spectrum (CHCl$_3$): 3606, 3416, 3357, 2927, 2855, 1713, 1663, 1602 cm$^{-1}$; NMR spectrum (400 MHz, CD$_3$OD) δ: 0.90 (12H, t, J=6.6 Hz), 1.23–1.75 (86H, m), 2.00 (3H, s), 2.20 (2H, t, J=7.3 Hz), 2.34–2.37 (2H, m), 3.45 (1H, m), 3.58–4.04 (13H, m), 4.20 (1H, m), 4.38–4.58 (4H, m, containing 1H, d, J=5.1 Hz, at 4.47 ppm), 4.70 (1H, d, J=8.1 Hz), 7.19–7.42 (10H, m); Mass spectrum (m/z): 1528.9941 (M+Na)$^+$.

REFERENCE EXAMPLE 42

Allyl 2-Deoxy-3-O-{(R)-3-dodecyloxytetradecyl}-4,6-O-isopropylidene-2-trifluoroacetylamino-α-D-glucopyranoside To a solution of starting material allyl 2-deoxy-4,6-isopropylidene-2-trifluoroacetylamino-α-D-glucopyranoside (4.23 g, 11.9 mmol) in dimethylformamide (60 ml) was added sodium hydride (725 mg, 18.1 mmol, 60% in oil) at 0° C. and the mixture was stirred for 30 minutes. To this mixture was added (R)-3-(dodecyloxy)-1-methanesulfonyloxytetradecane (6.80 g, 14.3 mmol) and the mixture stirred at room temperature for 3 hours. The reaction was quenched by the addition of water and the reaction mixture was extracted with ethyl acetate. The ethyl acetate layer was washed with water and saturated aqueous sodium chloride solution, dried over magnesium sulfate and then concentrated in vacuo. The residue was purified by chromatography on a silica gel column using hexane: ethyl acetate= 4:1 as the eluant to give the desired product (6.60 g, yield 75%).

IR spectrum (CHCl$_3$): 3431, 2928, 2855, 1734 cm$^{-1}$; NMR spectrum (400 MHz, CDCl$_3$) δ: 6.55 (1H, d, J=9.5 Hz, NH), 5.86 (1H, m), 5.31–5.24 (2H, m), 4.89 (1H, d, J=3.7 Hz), 4.20–4.13 (2H, m), 3.98 (1H, dd, J=5.1, 12.5 Hz), 3.89–3.83 (2H, m), 3.78–3.67 (3H, m), 3.58–3.49 (2H, m), 3.41–3.29 (3H, m), 1.67–1.21 (48H, m, containing 3H, s, δ 1.51, 3H, s, 8 1.41), 0.88 (6H, t, J=6.6 Hz); Mass spectrum (m/z): 736.5337 (M+H)$^+$; Analyses for: $C_{40}H_{72}F_3NO_7$ (Molecular weight: 736.0); Calculated: C, 65.28; H, 9.86; N, 1.90; F, 7.74. Found: C, 65.35; H, 9.89; N, 1.90; F, 7.86.

REFERENCE EXAMPLE 43

Allyl 2-Deoxy-3-O-{(R)-3-dodecyloxytetradecyl}-4,6-O-isopropylidene-2-(2,2,2-trichloroethoxycarbonylamino)-α-D-glucopyranoside To a solution of the compound of Reference Example 42 (4.70 g, 6.39 mmol) in ethanol (10 ml) was added aqueous sodium hydroxide (10 ml, 1M) and the mixture was stirred at 80° C. for 4 hours and then concentrated in vacuo. The residue was diluted with ethyl acetate. The ethyl acetate layer was washed with water and saturated aqueous sodium chloride solution, dried over sodium sulfate, concentrated in vacuo and then dried under high vacuum to afford an amine derivative (4.02 g). The amine derivative was dissolved in methylene chloride (10 ml). To this solution was added saturated aqueous sodium hydrogencarbonate (10 ml) and 2,2,2-trichloroethyl chlorofonnate (1.60 g, 7.55 mmol) and the mixture was stirred at room temperature for 1 hour. The reaction mixture was diluted with methylene chloride and the organic layer was washed with water and saturated aqueous sodium chloride solution, dried over magnesium sulfate and then concentrated under reduced pressure. The residue was purified by chromatography on a silica gel column using hexane: ethyl acetate=4:1 as the eluant to give the desired product (4.54 g, yield 87%).

IR spectrum (CHCl$_3$): 3439, 2928, 2855, 1743 cm$^{-1}$; NMR spectrum (400 MHz, CDCl$_3$) δ: 5.89 (1H, m), 5.32–5.22 (3H, m, containing NH), 4.87 (1H, d, J=3.7 Hz), 4.74 (2H, s), 4.13 (1H, dd, J=5.9, 12.5 Hz), 3.98 (1H, dd, J=6.6, 12.5 Hz), 3.92–3.82 (3H, m), 3.77–3.57 (4H, m), 3.48–3.30 (4H, m), 1.68–1.21 (48H, m, containing 3H, s, δ 1.50, 3H, s, δ 1.41), 0.88 (6H, t, J=6.6–7.3 Hz); Mass spectrum (m/z): 814.4551 (M+H)$^+$; Analyses for: C$_{41}$H$_{74}$Cl$_3$NO$_8$ (Molecular weight: 815.4); Calculated: C, 60.39; H, 9.15; N, 1.72; Cl, 13.04. Found: C, 59.84; H, 9.04; N, 1.70; Cl, 12.89.

REFERENCE EXAMPLE 44

Allyl 2-Deoxy-3-O-{(R)-3-dodecyloxytetradecyl}-2-(2,2,2-trichloroethoxycarbonylamino)-α-D-glucopyranoside A solution of the compound of Reference Example 43 (3.51 g, 4.30 mmol) in aqueous acetic acid solution (20 ml, 80%) was stirred at 60° C. for 4 hours. The reaction mixture was concentrated in vacuo and diluted with ethyl acetate. The ethyl acetate layer was washed with saturated aqueous sodium hydrogencarbonate solution and saturated aqueous sodium chloride solution, dried over magnesium sulfate and then concentrated in vacuo. The residue was purified by chromatography on a silica gel column using hexane: ethyl acetate=3:2 as the eluant to give the desired product (3.15 g, yield 95%).

IR spectrum (KBr): 3335, 2923, 2853, 1709 cm$^{-1}$; NMR spectrum (400 MHz, CDCl$_3$) δ: 5.90 (1H, m), 5.32–5.22 (3H, m, containing NH), 4.87 (1H, d, J=3.7 Hz), 4.81, 4.69 (2H, ABq, J=11.7 Hz), 4.19 (1H, dd, J=5.1, 13.2 Hz), 3.99 (1H, dd, J=6.6, 13.2 Hz), 3.91–3.60 (8H, m, containing OH), 3.50–3.36 (4H, m), 2.17 (1H, t, OH), 1.73–1.26 (42H, m), 0.88 (6H, t, J=6.6 Hz); Mass spectrum (m/z): 774.4228 (M+H)$^+$; Analyses for: C$_3$8H$_7$OC$_{13}$NO$_8$ (Molecular weight: 775.3); Calculated: C, 58.87; H, 9.10; N, 1.81; Cl, 13.72; Found: C, 58.87; H, 8.94; N, 1.81; Cl, 14.00.

REFERENCE EXAMPLE 45

Allyl 6-O-Benzyloxycarbonyl-2-deoxy-3-O-{(R)-3-dodecyloxytetradecyl}-2-(2,2,2-trichloroethoxycarbonylamino)-α-D-glucopyranoside To a solution of the compound of Reference Example 44 (526 mg, 0.678 mmol) in methylene chloride (5 ml) was added benzyloxycarbonyl chloride (0.50 ml, 3.50 mmol) and pyridine (332 mg, 4.20 mmol) and the mixture was stirred at 0° C. for 3 hours. The reaction mixture was diluted with ethyl acetate. The ethyl acetate layer was washed with saturated aqueous ammonium chloride solution, saturated aqueous sodium hydrogencarbonate solution, water and saturated aqueous sodium chloride solution, dried over magnesium sulfate and then concentrated in vacuo. The residue was purified by chromatography on a silica gel column using hexane: ethyl acetate=3:1 as the eluant to give the desired product (581 mg, yield 94%).

IR spectrum (KBr): 3522, 3329, 2923, 2853, 1725, 1709 cm$^{-1}$; NMR spectrum (400 MHz, CDCl$_3$) δ: 7.40–7.32 (5H, m), 5.87 (1H, m), 5.30–5.20 (3H, m, containing NH), 5.18 (2H, s), 4.85 (1H, d, J=3.7 Hz), 4.81, 4.68 (2H, ABq, J=12.5 Hz), 4.46–4.39 (2H, m), 4.15 (1H, dd, J=5.1, 12.5 Hz), 3.96 (1H, dd, J=6.6, 12.5 Hz), 3.88 (1H, td, J=10.3, 3.7 Hz), 3.84–3.79 (2H, m), 3.69 (1H, m), 3.64 (1H, brs, OH), 3.56 (1H, m), 3.48–3.33 (4H, m), 1.74–1.71 (2H, m), 1.59–1.21 (40H, m), 0.88 (6H, t, J=6.6 Hz); Mass spectrum (m/z): 908.4592 (M+H)$^+$; Analyses for: C$_{46}$H$_{76}$Cl$_3$NO$_{10}$ (Molecular weight: 909.5); Calculated: C, 60.75; H, 8.42; N, 1.54; Cl, 11.70. Found: C, 60.44; H, 8.17; N, 1.56; Cl, 11.63.

REFERENCE EXAMPLE 46

Allyl 6-O-Benzyloxycarbonyl-2-deoxy-4-O-diphenylphosphono-3-O-{(R)-3-dodecyloxytetradecyl}-2-(2,2,2-trichloroethoxycarbonylamino)-α-D-glucopyranoside To a solution of the compound of Reference Example 45 (553 mg, 0.608 mmol) in methylene chloride (5 ml) was added 4-dimethylaminopyridine (111 mg, 0.911 mmol) and diphenylchlorophosphate (0.19 ml, 0.608 mmol) and the mixture was stirred at room temperature for 2 hours. The reaction mixture was diluted with ethyl acetate. The ethyl acetate layer was washed with saturated aqueous sodium hydrogencarbonate solution, water and saturated aqueous sodium chloride solution, dried over magnesium sulfate and then concentrated in vacuo. The residue was purified by chromatography on a silica gel column using hexane: ethyl acetate=3:1 as the eluant to give the desired product (663 mg, yield 96%).

IR spectrum (CHCl$_3$): 3436, 2928, 2855, 1747 cm$^{-1}$; NMR spectrum (400 MHz, CDCl$_3$) δ: 7.36–7.12 (15H, m), 5.87 (1H, m), 5.30–5.21 (3H, m, containing NH), 5.11, 5.06 (2H, ABq, J=12.5 Hz), 4.89 (1H, d, J=3.7 Hz), 4.79, 4.67 (2H, ABq, J=12.5 Hz), 4.63 (1H, q, J=9.5 Hz), 4.36 (1H, dd, J=1.5, 11.7 Hz), 4.29 (1H, dd, J=5.1, 11.7 Hz), 4.14 (1H, dd, J=5.1, 13.2 Hz), 4.02–3.95 (3H, m), 3.80 (1H, m), 3.72–3.64 (2H, m), 3.25 (2H, t, J=6.6 Hz), 3.20 (1H, m), 1.63–1.61 (2H, m), 1.45–1.43 (2H, m), 1.30–1.18 (38H, m), 0.88 (6H, t, J=6.6 Hz); Mass spectrum (m/z): 1140.4890 (M+H)$^+$; Analyses for: C$_{58}$H$_{85}$Cl$_3$NO$_{13}$P (Molecular weight: 1141.6); Calculated: C, 61.02; H, 7.51; N, 1.23; Cl, 9.32; P, 2.71. Found: C, 60.49; H, 7.61; N, 1.19; Cl, 9.44; P, 2.96.

REFERENCE EXAMPLE 47

6-O-Benzyloxycarbonyl-2-deoxy-4-O-diphenylphosphono-3-O-{(R)-3-dodecyloxytetradecyl}-2-(2,2,2-trichloroethoxycarbonylamino)-D-glucopyranose To a solution of compound from Reference example 46 (613 mg, 0.537 mmol) in tetrahydrofuran (6 ml) was added (1,5-cyclooctadiene)bis(methyldiphenylphosphine)iridium hexafluorophosphate (31.5 mg) and the air of the reaction vessel was substituted with hydrogen. After the mixture became a clear red solution, the hydrogen was replaced with nitrogen and the mixture was stirred at room temperature for 1 hour. To the reaction mixture were added water (5 ml) and iodine (276 mg, 1.09 mmol) and this mixture was stirred at room temperature for 30 minutes. The reaction mixture was diluted with ethyl acetate. The ethyl acetate layer was washed with aqueous sodium thiosulfate solution (10%), saturated aqueous sodium hydrogencarbonate solution and saturated aqueous sodium chloride solution, dried over magnesium sulfate and then concentrated in vacuo. The residue was purified by chromatography on a silica gel column using hexane: ethyl acetate=3:2 as the eluant to give the desired product (421 mg, yield 71%).

IR spectrum (CHCl$_3$): 3600, 3435, 2928, 2855, 1747 cm$^{-1}$; NMR spectrum (400 MHz, CDCl$_3$) δ: 7.34–7.12 (15H, m), 5.43 (1H, d, J=9.5 Hz, NH), 5.25 (1H, t, J=3.7 Hz), 5.11, 5.06 (2H, ABq, J=11.7 Hz), 4.76, 4.69 (2H, ABq, J=12.1 Hz), 4.62 (1H, q, J=9.5 Hz), 4.39–4.19 (3H, m), 3.94 (1H, m), 3.84–3.64 (3H, m), 3.41 (1H, brs, OH), 3.27–3.20 (3H, m, containing 2H, t, J=6.6 Hz, δ 3.25), 1.65–1.62 (2H, m), 1.45–1.43 (2H, m), 1.30–1.18 (38H, m), 0.88 (6H, t, J=6.6 Hz); Mass spectrum (m/z): 1100.4601 (M+H)$^+$; Analyses for: C$_{55}$H$_{81}$Cl$_3$NO$_{13}$P (Molecular weight: 1101.6); Calculated: C, 59.97; H, 7.41; N, 1.27; Cl, 9.66; P, 2.81. Found: C, 58.85; H, 7.25; N, 1.22; Cl, 9.73; P, 2.98.

REFERENCE EXAMPLE 48

Allyl 6-O-tert-Butyldimethylsilyl-2-deoxy-3-O-{(R)-3-dodecyloxytetradecyl}-2-(2,2,2-trichloroethoxycarbonylamino)-α-D-glucopyranoside To a solution of the compound of Reference Example 44 (1.32 g, 1.70 mmol) in methylene chloride (6 ml) was added tert-butyldimethylsilyl chloride (385 mg, 2.56 mmol) and 4-dimethylaminopyridine (332 mg, 2.72 mmol) and the mixture was stirred at room temperature for 3 hours. The reaction mixture was diluted with ethyl acetate. The ethyl acetate layer was washed with water and saturated aqueous sodium chloride solution, dried over magnesium sulfate and then concentrated in vacuo. The residue was purified by chromatography on a silica gel column using hexane: ethyl acetate=9:1 as the eluant to give the desired product (1.49 g, yield 99%).

IR spectrum (CHCl$_3$): 3438, 2928, 2856, 1742 cm$^{-1}$; NMR spectrum (400 MHz, CDCl$_3$) δ: 5.90 (1H, m), 5.31–5.20 (3H, m, containing NH), 4.86 (1H, d, J=3.7 Hz), 4.79, 4.70 (2H, ABq, J=12.5 Hz), 4.19 (1H, dd, J=5.1, 12.5 Hz), 3.98 (1H, dd, J=6.6, 12.5 Hz), 3.89–3.76 (5H, m), 3.67–3.36 (7H, m, containing OH), 1.72 (2H, q, J=5.9 Hz), 1.62–1.21 (40H, m), 0.91–0.86 (15H, m), 0.090 (6H, s); Mass spectrum (m/z): 910.4911 (M+Na)$^+$; Analyses for: C$_{44}$H$_{84}$Cl$_3$NO$_8$Si (Molecular weight: 889.6); Calculated: C, 59.41; H, 9.52; N, 1.58; Cl, 11.96. Found: C, 59.03; H, 9.30; N, 1.49; Cl, 12.02.

REFERENCE EXAMPLE 49

Allyl 6-O-tert-Butyldimethylsilyl-4-O-diphenylphosphono-2-deoxy-3-O-{(R)-3-dodecyloxytetradecyl}-2-(2,2,2-trichloroethoxycarbonylamino)-α-D-glucopyranoside The compound of Reference Example 48 (1.45 g, 1.63 mmol) was treated according to a procedure analogous to Reference Example 46 to give the desired product (1.81 g, yield 99%).

IR spectrum (CHCl$_3$): 3436, 2928, 2856, 1744 cm$^{-1}$; NMR spectrum (400 MHz, CD$_3$OD) δ 7.35–7.15 (10H, m), 5.92 (1H, m), 5.33–5.23 (3H, m, containing NH), 4.90 (1H, d, J=3.7 Hz), 4.81, 4.69 (2H, ABq, J=12.1 Hz), 4.55 (1H, q, J=9.5 Hz), 4.22 (1H, dd, J=5.9, 13.2 Hz), 4.03–3.86 (2H, m), 3.83–3.65 (6H, m), 3.26–3.19 (3H, m), 1.65–1.18 (42H, m), 0.91–0.85 (15H, m), 0.009 (6H, s) Mass spectrum (m/z): 1120.5409 (M+H)$^+$; Analyses for: C$_{56}$H$_{93}$Cl$_3$NO$_{11}$SiP (Molecular weight: 1121.8); Calculated: C, 59.96; H, 8.36; N, 1.25; Cl, 9.48; P, 2.76. Found: C, 59.49; H, 8.23; N, 1.18; Cl, 9.66; P, 2.81.

REFERENCE EXAMPLE 50

Allyl 4-O-Diphenylphosphono-2-deoxy-3-O-{(R)-3-dodecyloxytetradecyl}-2-(2,2,2-trichloroethoxycarbonylamino)-α-D-glucopyranoside To a solution of the compound of Reference Example 49 (1.65 g, 1.47 mmol) in tetrahydrofuran (9 ml) was added aqueous hydrochloric acid solution (1.5 ml, 3N) and the mixture was stirred at room temperature for 3 hours. The reaction mixture was diluted with ethyl acetate. The ethyl acetate layer was washed with saturated aqueous sodium hydrogencarbonate solution, water and saturated aqueous sodium chloride solution, dried over magnesium sulfate and then concentrated in vacuo. The residue was purified by chromatography on a silica gel column using hexane: ethyl acetate 3:2 as the eluant to give the desired product (1.31 g, yield 89%).

IR spectrum (KBr): 3499, 3373, 2921, 2851, 1713, 1646 cm$^{-1}$; NMR spectrum (400 MHz, CDCl$_3$) δ: 7.37–7.18 (10H, m), 5.89 (1H, m), 5.33–5.23 (3H, m, containing NH), 4.93 (1H, d, J=3.7 Hz), 4.76, 4.72 (2H, ABq, J=12.5 Hz), 4.65 (1H, q, J=9.5 Hz), 4.17 (1H, dd, J=5.9, 13.2 Hz), 4.03–3.97 (2H, m), 3.88 (1H, m), 3.70–3.59 (5H, m), 3.29–3.21 (3H, m), 1.65 (1H, q, J=6.6 Hz), 1.47–1.18 (40H, m), 0.88 (6H, t, J=6.6 Hz); Mass spectrum (m/z): 1006.4539 (M+H)$^+$; Analyses for: C$_{50}$H$_{79}$Cl$_3$NO$_{11}$P (Molecular weight: 1007.5); Calculated: C, 59.61; H, 7.90; N, 1.39; Cl, 10.56; P, 3.07. Found: C, 59.19; H, 7.82; N, 1.37; Cl, 10.66; P, 3.09.

REFERENCE EXAMPLE 51

Allyl 4-O-Diphenylphosphono-2-deoxy-3-O-{(R)-3-dodecyloxytetradecyl}-6-O-methyl-2-(2,2,2-trichloroethoxycarbonylamino)-α-D-glucopyranoside To a solution of the compound of Reference Example 50 (385 mg, 0.382 mmol) in methylene chloride (5 ml) were added 2,6-di-tert-butyl-4-methylpyridine (91 mg, 0.441 mmol) and trimethyloxonium tetrafluoroborate (64 mg, 0.435 mmol) and the mixture was stirred at room temperature for 20 hours. The reaction mixture was diluted with ethyl acetate. The ethyl acetate layer was washed with water, saturated aqueous sodium hydrogencarbonate solution and saturated aqueous sodium chloride solution, dried over magnesium sulfate and then concentrated in vacuo. The residue was purified by chromatography on a silica gel column using hexane: ethyl acetate=7:3 as the eluant to give the desired product (357 mg, yield 91%).

IR spectrum (CHCl$_3$): 3436, 2928, 2855, 1744 cm$^{-1}$; NMR spectrum (400 MHz, CDCl$_3$) δ: 7.35–7.15 (10H, m), 5.90 (1H, m), 5.33–5.23 (3H, m, containing NH), 4.93 (1H, d, J=3.7 Hz), 4.77, 4.69 (2H, ABq, J=11.7 Hz), 4.67 (1H, m), 4.21 (1H, dd, J=5.1, 13.2 Hz), 4.04–3.98 (2H, m), 3.89–3.65 (4H, m), 3.54 (1H, dd, J=4.4, 11.0 Hz), 3.48 (1H, dd, J=2.2, 11.0 Hz), 3.26–3.19 (6H, m, containing 3H, s, 6 3.24), 1.64–1.62 (2H, m), 1.44–1.43 (2H, m), 1.32–1.17 (38H, m), 0.88 (6H, t, J=6.6 Hz); Mass spectrum (m/z): 1020.4669 $(M+H)^+$; Analyses for: $C_{51}H_{81}Cl_3NO_{11}P$ (Molecular weight: 1021.5); Calculated: C, 59.97; H, 7.99; N, 1.37; Cl, 10.41; P, 3.03. Found: C, 59.10; H, 7.85; N, 1.29; Cl, 10.51; P, 3.27.

REFERENCE EXAMPLE 52

4-O-Diphenylphosphono-2-deoxy-3-O-{(R)-3-dodecyloxytetradecyl}-6-O-methyl-2-(2,2,2-trichloroethoxycarbonylamino)-D-glucopyranose The compound from Reference Example 51 (695 mg, 0.681 mmol) was treated according to a procedure analogous to Reference Example 47 to give the desired product (483 mg, yield 72%).

IR spectrum (KBr): 3426, 3339, 2922, 2851, 1721 $cm^{-1}$; NMR spectrum (400 MHz, $CDCl_3$) δ: 7.35–7.16 (10H, m), 5.40 (1H, d, J=9.5 Hz, NH), 5.27 (1H, t, J=3.7 Hz), 4.75, 4.70 (2H, ABq, J=11.7 Hz), 4.55 (1H, q, J=9.5 Hz), (1H, m), 3.95 (1H, m), 3.85–3.65 (4H, m, containing OH), 3.51–3.43 (2H, m), 3.26–3.16 (6H, m, containing 2H, t, J=6.6 Hz, 6 3.25, 3H, s, 6 3.21), 1.65–1.64 (2H, m), 1.44–1.42 (2H, m), 1.32–1.17 (38H, m), 0.88 (6H, t, J=6.6 Hz); Mass spectrum (m/z): 980.4378 $(M+H)^+$; Analyses for: $C_{48}H_{77}Cl_3NO$, P (Molecular weight: 981.5); Calculated: C, 58.74; H, 7.91; N, 1.43; Cl, 10.84; P, 3.16. Found: C, 58.49; H, 8.15; N, 1.51; Cl, 10.74; P, 3.24.

REFERENCE EXAMPLE 53

Allyl 2,6-Deoxy-4-O-diphenylphosphono-3-O-{(R)-3-dodecyloxytetradecyl}-6-fluoro-2-(2,2,2-trichloroethoxycarbonylamino)-α-D-glucopyranoside To a solution of compound from Reference Example 50 (521 mg, 0.517 mmol) in 1,2-dimethoxyethane (5 ml) was added diethylaminosulfur trifluoride (DAST) (0.2 ml, 1.51 mmol) under nitrogen atmosphere at −40° C. and the mixture was stirred for 30 minutes and then stirred at 0° C., for 2 hours. The reaction was quenched by the addition of water and the reaction mixture was extracted with ethyl acetate. The ethyl acetate layer was washed with saturated aqueous sodium hydrogencarbonate solution and saturated aqueous sodium chloride solution, dried over magnesium sulfate and then concentrated in vacuo. The residue was purified by chromatography on a neutral silica gel column using hexane: ethyl acetate=3:1 as the eluant to give the desired product (432 mg, yield 83%).

IR spectrum ($CHCl_3$): 3691, 3436, 2928, 2855, 1744 $cm^{-1}$; NMR spectrum (400 MHz, $CDCl_3$) δ: 7.34–7.16 (10H, m), 5.89 (1H, m), 5.34–5.24 (3H, m, containing NH), 4.94 (1H, d, J=3.7 Hz), 4.79, 4.68 (2H, ABq, J=1 1.7 Hz), 4.64–4.55 (2H, m), 4.46 (1H, m), 4.20 (1H, dd, J=5.9, 13.2 Hz), 4.05–3.90 (3H, m), 3.83–3.65 (3H, m), 3.25 (2H, t, J=6.6–7.3 Hz), 3.21 (1H, m), 1.65–1.57 (2H, m), 1.45–1.43 (2H, m), 1.32–1.17 (38H, m), 0.88 (6H, t, J=6.6–7.3 Hz); Mass spectrum (m/z): 1008.4485 $(M+H)^+$; Analyses for: $C_{50}H_{78}Cl_3FNO_{10}P$ (Molecular weight: 1009.5); Calculated: C, 59.49; H, 7.79; N, 1.39; Cl, 10.54; F, 1.88; P, 3.07. Found: C, 59.45; H, 7.68; N, 1.48; Cl, 10.45; F, 2.25; P, 3.24.

REFERENCE EXAMPLE 54

2,6-Dideoxy-4-O-diphenylphosphono-3-O-{(R)-3-dodecyloxytetradecyl}-6-fluoro-2-(2,2,2-trichloroethoxycarbonylamino)-D-glucopyranose The compound of Reference Example 53 (416 mg, 0.412 mmol) was treated according to a procedure analogous to Reference Example 47 to give the desired product (329 mg, yield 82%).

IR spectrum ($CHCl_3$): 3602, 3435, 2928, 2855, 1745 $cm^{-1}$; NMR spectrum (400 MHz, $CDCl_3$) δ: 7.35–7.17 (10H, m), 5.47 (1H, d, J=9.5 Hz, NH), 5.31 (1H, t, J=3.7 Hz), 4.76, 4.71 (2H, ABq, J=11.7 Hz), 4.60 (1H, q, J=9.5 Hz), 4.56 (1H, m), 4.44 (1H, m), 4.17 (1H, m), 3.96 (1H, m), 3.85–3.65 (4H, m, containing OH), 3.27–3.21 (3H, m, containing 2H, t, J=6.6 Hz, 6 3.26), 1.67–1.62 (2H, m), 1.45–1.44 (2H, m), 1.32–1.18 (38H, m), 0.88 (6H, t, J=6.6 Hz); Mass spectrum (m/z): 968.4178 $(M+H)^+$; Analyses for: $C_{47}H_{74}Cl_3FNO_{10}P$ (Molecular weight: 969.4); Calculated: C, 58.23; H, 7.69; N, 1.45; Cl, 10.97; F, 1.96; P, 3.20. Found: C, 58.27; H, 7.76; N, 1.43; Cl, 11.20; F, 2.04; P, 3.25.

REFERENCE EXAMPLE 55

Diphenylmethyl 2,6-Anhydro-7-O-[6-O-benzyloxycarbonyl-2-deoxy-4-O-diphenylphosphono-3-O-{(R)-3-dodecyloxytetradecyl}-2-(2,2,2-trichloroethoxycarbonylamino)-β-D-glucopyranosyl]-3-{(R)-3-benzyloxytetradecanoylamino}-4-O-{(R)-3-benzyloxytetradecyl}-3-deoxy-D-glycero-D-ido-heptonate To a solution of the compound of Reference Example 47 (521 mg, 0.473 mmol) in methylene chloride (10 ml) was added trichloroacetonitrile (0.70 ml, 6.98 mmol) and cesium carbonate (77 mg, 0.237 mmol) and the mixture was stirred at room temperature for 1 hour. The reaction was quenched by the addition of saturated aqueous sodium hydrogencarbonate solution (20 ml) and the reaction mixture was extracted with methylene chloride. The organic layer was washed with saturated aqueous sodium chloride solution, dried over sodium sulfate, concentrated in vacuo and then dried under high vacuum to give a 1-trichloroacetoimidate compound (591 mg, quantitative yield).

To a solution of the imidate compound and diphenylmethyl 2,6-anhydro-3-{(R)-3-benzyloxytetradecanoylamino}-4-O-{(R)-3-benzyloxytetradecyl}-3-deoxy-D-glycero-D-ido-heptonate (234 mg, 0.236 mmol) in methylene chloride (10 ml) was added molecular sieves 4A (750 mg) and the mixture was stirred to remove water in the reaction mixture at room temperature for 1 hour. To this reaction mixture was added trimethylsilyl trifluoromethanesulfonate (15 μl, 0.0829 mmnol) at −40° C. and the mixture was stirred for 2 hours. The reaction mixture was filtered and saturated aqueous sodium hydrogencarbonate solution was added to the filtrate which was then extracted with ethyl acetate. The organic layer was washed with saturated aqueous sodium hydrogencarbonate solution and saturated aqueous sodium chloride solution, dried over magnesium sulfate and concentrated in vacuo. The residue was purified by chromatography on a silica gel column using hexane: ethyl acetate=7:3 as the eluant to give the desired product (365 mg, yield 75%).

IR spectrum ($CHCl_3$): 3691, 3604, 3519, 3405, 2928, 2855, 1735, 1669 $cm^{-1}$; NMR spectrum (400 MHz, $CDCl_3$) δ: 7.35–7.11 (35H, m), 6.83 (1H, s), 6.81 (1H, m, NH), 5.39 (1H, m, NH), 5.10, 5.04 (2H, ABq, J=11.7 Hz), 4.86 (1H, m), 4.71, 4.66 (2H, ABq, J=11.7 Hz), 4.61 (1H, d, J=5.9 Hz), 4.51 (1H, q, J=9.5 Hz), 4.45–4.21 (7H, m, containing 2H, ABq, J=11.5 Hz, 6 4.44, 4.39, 2H, ABq, J=11.0 Hz, 6 4.33, 4.28), 4.07–3.92 (2H, m), 3.72–3.43 (1H, m), 3.27–3.14 (4H, m), 3.02 (1H, brs, OH), 2.24 (2H, d, J=5.9 Hz), 1.74–1.24 (84H, m), 0.88 (12H, t, J=6.6 Hz); Mass spectrum (m/z): 2096.0845 $(M+Na)^+$; Analyses for: C$_{117}$H$_{168}$Cl$_3$N$_2$O$_{21}$P (Molecular weight: 2075.9); Calculated:

C, 67.69; H, 8.16; N, 1.35; Cl, 5.12; P, 1.49. Found: C, 67.01; H, 8.04; N, 1.34; Cl, 5.27; P, 1.37.

REFERENCE EXAMPLE 56

Diphenylmethyl 2,6-Anhydro-7-O-[2-deoxy-4-O-diphenylphosphono-3-O-{(R)-3-dodecyloxytetradecyl}-6-O-methyl-2-(2,2,2-trichloroethoxycarbonylamino)-β-D-glucopyranosyl]-3-{(R)-3-benzyloxytetradecanoylamino}-4-O-{(R)-3-benzyloxytetradecyl}-3-deoxy-D-glycero-D-ido-heptonate The compound from Reference Example 52 (438 mg, 0.446 mmol) was treated according to a procedure analogous to Reference Example 55 to give the desired product (298 mg, yield 68%).

IR spectrum ($CHCl_3$): 2928, 2855, 1735, 1668 $cm^{-1}$; NMR spectrum (400 MHz, $CDCl_3$) δ: 7.35–7.15 (30H, m), 6.83 (1H, s), 6.79 (1H, d, J=9.5 Hz, NH), 5.33 (1H, m, NH), 4.84 (1H, m), 4.75, 4.67 (2H, ABq, J=11.7 Hz), 4.61 (1H, d, J=5.9 Hz), 4.54 (1H, q, J=9.5 Hz), 4.44, 4.40 (2H, ABq, J=11.7 Hz), 4.34–4.26 (3H, m, containing 2H, ABq, J=11.4 Hz, δ 4.33, 4.28), 4.00–3.89 (2H, m), 3.76–3.41 (13H, m), 3.27–3.10 (7H, m, containing 3H, s, δ 3.21), 3.03 (1H, brs, OH) 2.23 (2H, d, J=5.9 Hz), 1.75–1.24 (84H, m), 0.88 (12H, t, J=6.6 Hz); Mass spectrum (m/z): 1976.0585 $(M+Na)^+$; Analyses for: $C_{110}H_{164}Cl_3N_2O_{19}P$ (Molecular weight: 1955.8); Calculated: C, 67.55; H, 8.45; N, 1.43; Cl, 5.44; P, 1.58. Found: C, 67.53; H, 8.25; N, 1.43; Cl, 5.14; P, 1.32.

REFERENCE EXAMPLE 57

Diphenylmethyl 2,6-Anhydro-7-O-[2,6-dideoxy-4-O-diphenylphosphono-3-O-{(R)-3-dodecyloxytetradecyl}-6-fluoro-2-(2,2,2-trichloroethoxycarbonylamino)-β-D-glucopyranosyl]-3-{(R)-3-benzyloxytetradecanoylamino}-4-O-{(R)-3-benzyloxytetradecyl}-3-deoxy-D-glycero-D-ido-heptonate The compound from Reference Example 54 (230 mg, 0.238 mmol) was treated according to a procedure analogous to Reference Example 55 to give the desired product (185 mg, yield 80%).

IR spectrum ($CHCl_3$): 2928, 2855, 1735, 1669 $cm^{-1}$; NMR spectrum (400 MHz, $CDCl_3$) δ: 7.35–7.17 (30H, m), 6.83 (1H, s), 6.82 (1H, m, NH), 5.43 (1H, m, NH), 4.90 (1H, m), 4.75,4.67 (2H, ABq, J=11.7 Hz), 4.61 (1H, d, J=5.1 Hz), 4.57–4.26 (8H, m, containing 2H, ABq, J=1 1.7 Hz, δ 4.45, 4.40, 2H, ABq, J=11.4 Hz, δ 4.33, 4.28), 4.02–3.92 (2H, m), 3.75–3.43 (11H, m), 3.27–3.15 (4H, m), 3.03 (1H, brs, OH), 2.25 (2H, d, J=5.9 Hz), 1.74–1.25 (84H, m), 0.88 (12H, t, J=6.6 Hz); Mass spectrum (m/z): 1964.0414 $(M+Na)^+$; Analyses for: $C_{109}H_{161}Cl_3FN_2O_{18}P$ (Molecular weight: 1943.78); Calculated: C, 67.35; H, 8.35; N, 1.44; F, 0.98; Cl, 5.47; P, 1.59. Found: C, 67.34; H, 8.10; N, 1.48; F, 1.26; Cl, 5.39; P, 1.43.

REFERENCE EXAMPLE 58

Diphenylmethyl 2,6-Anhydro-7-O-[2-acetylamino-6-benzyloxycarbonyl-2-deoxy-4-O-diphenylphosphono-3-O-{(R)-3-dodecyloxytetradecyl}-β-D-glucopyranosyl]-3-{(R)-3-benzyloxytetradecanoylamino}-4-O-{(R)-3-benzyloxytetradecyl}-3-deoxy-D-glycero-D-ido-heptonate To a solution of the compound of Reference Example 55 (230 mg, 0.111 mmol) in acetic acid (5 ml) was added zinc treated with acid (148 mg, 2.27 mmol) and the mixture was stirred for 5 hours. The reaction mixture was filtered and the filtrate was concentrated and the residue was diluted with ethyl acetate. The ethyl acetate layer was washed with saturated aqueous sodium hydrogencarbonate solution and saturated aqueous sodium chloride solution, dried over sodium sulfate and then concentrated in vacuo to give an amine compound. To a solution of the amine compound in a mixture of tetrahydrofuran (3 ml) and water (2 ml) were added pyridine (45 μl, 0.556 mmol) and acetic anhydride (55 μl, 0.583 mmol) and the mixture was stirred at room temperature for 2 hours. The reaction mixture was diluted with ethyl acetate. The ethyl acetate layer was washed with water and saturated aqueous sodium chloride solution, dried over magnesium sulfate and then concentrated in vacuo. The residue was purified by chromatography on a silica gel column using hexane: ethyl acetate=3:2 as the eluant to give the desired product (152 mg, yield 71%).

IR spectrum ($CHCl_3$): 3436, 2928, 2855, 1745, 1670 $cm^{-1}$; NMR spectrum (400 MHz, $CDCl_3$) δ: 7.33–7.12 (35H, m), 6.82 (1H, s), 6.80 (1H, d, J=8.8 Hz, NH), 6.07 (1H, d, J=6.6 Hz, NH), 5.21 (1H, d, J=8.1 Hz), 5.11,5.05 (2H, ABq, J=11.7 Hz), 4.62 (1H, d, J=5.1 Hz), 4.50 (1H, q, J=9.5 Hz), 4.43 (2H, s), 4.39–4.28 (5H, m), 4.23 (1H, dd, J=5.1, 11.7 Hz), 4.07–4.00 (2H, m), 3.72–3.27 (14H, m, containing OH), 3.03 (1H, m), 2.25 (2H, d, J=5.1 Hz), 1.91 (3H, s), 1.73–1.26 (84H, m), 0.89 (12H, t, J=6.6 Hz); Mass spectrum (m/z): 1964.1870 $(M+Na)^+$; Analyses for: $C_{116}H_{169}N_2O_{20}P$ (Molecular weight: 1942.6). Calculated: C, 71.72; H, 8.77; N, 1.44; P, 1.59. Found: C, 71.46; H, 8.60; N, 1.42; P, 1.49.

REFERENCE EXAMPLE 59

Diphenylmethyl 2,6-Anhydro-7-O-[2-acetylamino-2-deoxy-4-O-diphenylphosphono-3-O-{(R)-3-dodecyloxytetradecyl}-6-O-methyl-β-D-glucopyranosyl]-3-{(R)-3-benzyloxytetradecanoylamino}-4-O-{(R)-3-benzyloxytetradecyl}-3-deoxy-D-glycero-D-ido-heptonate The compound from Reference Example 56 (229 mg, 0.117 mmol) was treated according to a procedure analogous to Reference Example 58 to give the desired product (158 mg, yield 74%).

IR spectrum ($CHCl_3$): 3436, 2928, 2855, 1732, 1670 $cm^{-1}$; NMR spectrum (400 MHz, $CDCl_3$) δ: 7.33–7.15 (30H, m), 6.81 (1H, s), 6.78 (1H, d, J=8.8 Hz, NH), 5.97 (1H, d, J=7.3 Hz, NH), 5.15 (1H, d, J=8.1 Hz), 4.61 (1H, d, J=5.9 Hz), 4.52 (1H, q, J=9.5 Hz), 4.42 (2H, s), 4.35 (1H, m), 4.33, 4.29 (2H, ABq, J=11.4 Hz), 4.05–3.99 (2H, m), 3.74–3.40 (14H, m, containing OH), 3.30–3.22 (6H, m, containing 3H, s, δ 3.22), 3.11 (1H, m), 2.23 (2H, d, J=5.1 Hz), 1.91 (3H, s), 1.74–1.25 (84H, m), 0.88 (12H, t, J=6.6 Hz); Mass spectrum (m/z): 1844.1700 $(M+Na)^+$; Analyses for: $C_{109}H_{165}N_2O_{18}P$ (Molecular weight: 1822.5); Calculated: C, 71.84; H, 9.13; N, 1.54; P, 1.70. Found: C, 71.38; H, 8.96; N, 1.51; P, 1.53.

REFERENCE EXAMPLE 60

Diphenylmethyl 2,6-Anhydro-7-O-[2-acetylamino-2,6-dideoxy-4-O-diphenylphosphono-3-O-{(R)-3-dodecyloxytetradecyl}-6-fluoro-β-D-glucopyranosyl]-3-{(R)-3-benzyloxytetradecanoylamino}-4-O-{(R)-3-benzyloxytetradecyl}-3-deoxy-D-glycero-D-ido-heptonate The compound of Reference Example 57 (180 mg, 0.0927 mmol) was treated according to a procedure analogous to Reference Example 58 to give the desired product (115 mg, yield 68%).

IR spectrum (CHCl$_3$): 3529, 3335, 3064, 3032, 2924, 2854, 1733, 1646 cm$^{-1}$; NMR spectrum (400 MHz, CDCl$_3$) δ: 7.37–7.17 (30H, m), 6.82 (1H, s), 6.80 (1H, d, J=11.7 Hz, NH), 6.03 (1H, d, J=6.6 Hz, NH), 5.21 (1H, d, J=8.1 Hz), 4.61 (1H, d, J=5.1 Hz), 4.57–4.27 (8H, m, containing 2H, s, δ 4.42, 2H, ABq, J=11.4 Hz, δ 4.34, 4.29), 4.11–4.03 (2H, m), 3.71–3.41 (11H, m), 3.33–3.22 (4H, m, containing OH), 3.04 (1H, m), 2.24 (2H, d, J=5.9 Hz), 1.91 (3H, s), 1.74–1.25 (84H, m), 0.88 (12H, t, J=6.6 Hz); Mass spectrum (m/z): 1832.1459 (C$_{108}$H$_{162}$FN$_2$O$_{17}$PNa); Analyses for: C$_{109}$H$_{165}$N$_2$O$_{18}$P (Molecular weight: 1822.5); Calculated: C, 71.84; H, 9.13; N, 1.54; P, 1.70. Found: C, 71.38; H, 8.96; N, 1.51; P, 1.53.

REFERENCE EXAMPLE 61

2,6-Anhydro-7-O-[2-acetylamino-2,6-deoxy-4-O-diphenylphosphono-3-O-{(R)-3-dodecyloxytetradecyl}-β-D-glucopyranosyl]-3-{(R)-3-hydroxytetradecanoylamino}-4-O-{(R)-3-hydroxytetradecyl}-3-deoxy-D-glycero-D-ido-heptonic Acid To a solution of the compound of Reference Example 58 (115 mg, 0.0593 mmol) in ethanol (5 ml) was added palladium hydroxide on carbon (111 mg, 20%). The mixture was stirred under a hydrogen atmosphere at room temperature for 18 hours. The reaction mixture was filtered and the filtrate concentrated in vacuo. The residue was purified by thin-layer-chromatography on a silica gel plate using chloroform: methanol=5:1. The eluted product was dissolved in chloroform (10 ml) and washed with aqueous hydrochloric acid (0.05M), the residual silica gel was removed and then the chloroform layer was concentrated in vacuo to give the desired product (62.3 mg, yield 72%).

IR spectrum (KBr): 3320 (broad), 3072, 2924, 2854, 1726, 1656 cm$^{-1}$; NMR spectrum (400 MHz, CD$_3$OD) δ: 7.40–7.19 (10H, m), 4.63 (1H, m), 4.53 (1H, m), 4.48 (1H, d, J=5.1 Hz), 4.21 (1H, m), 4.04 (1H, m), 3.93–3.52 (14H, m), 3.46 (1H, t, J=8.1 Hz), 3.35–3.25 (3H, m), 2.41–2.30 (2H, m), 2.00 (3H, s), 1.76–1.20 (84H, m), 0.90 (12H, t, J=6.6 Hz); Mass spectrum (m/z): 1483.9815 (M+Na)$^+$.

REFERENCE EXAMPLE 62

2,6-Anhydro-7-O-[2-acetylamino-2,6-dideoxy-4-O-diphenylphosphono-3-O-{(R)-3-dodecyloxytetradecyl}-6-O-methyl-β-D-glucopyranosyl]-3-{(R)-3-hydroxytetradecanoylamino}-4-O-{(R)-3-hydroxytetradecyl}-3-deoxy-D-glycero-D-ido-heptonic acid The compound from Reference Example 59 (136 mg, 0.0744 mmol) was treated according to a procedure analogous to Reference Example 61 to give the desired product (98.2 mg, yield 89%).

IR spectrum (KBr): 3318 (broad), 3072, 2924, 2854, 1729, 1656 cm$^{-1}$; NMR spectrum (400 MHz, CD$_3$OD$_3$) δ: 7.40–7.19 (10H, m), 4.75 (1H, d, J=8.1 Hz), 4.56 (1H, q, J=8.8 Hz), 4.29 (1H, m), 4.22–4.19 (2H, m), 4.00–3.22 (18H, m), 3.20 (3H, s), 2.40–2.33 (2H, m), 2.03 (3H, s), 1.75–1.21 (84H, m), 0.90 (12H, t, J=6.6 Hz); Mass spectrum (m/z): 1497.9939 (M+Na)$^+$;

REFERENCE EXAMPLE 63

2,6-Anhydro-7-O-[2-acetylamino-2,6-dideoxy-4-O-diphenylphosphono-3-O-{(R)-3-dodecyloxytetradecyl}-6-fluoro-β-D-glucopyranosyl]-3-{(R)-3-hydroxytetradecanoylamino}-4-O-{(R)-3-hydroxytetradecyl}-3-deoxy-D-glycero-D-ido-heptonic acid The compound of Reference Example 60 (75.2 mg, 0.0415 mmol) was treated according to a procedure analogous to Reference Example 61 to give the desired product (48.3 mg, yield 80%).

IR spectrum (KBr): 3323 (broad), 3072, 2924, 2854, 1729, 1656 cm$^{-1}$; NMR spectrum (400 MHz, CD$_3$OD) δ: 7.41–7.18 (10H, m), 4.68 (1H, d, J=8.1 Hz), 4.58–4.36 (4H, m, containing 1H, d, J=5.1 Hz, 5 4.49), 4.22–4.19 (2H, m), 4.03 (1H, m), 3.94–3.68 (10H, m), 3.60 (1H, t, J=7.3–9.5 Hz), 3.45 (1H, t, J=8.1 Hz), 3.36–3.25 (3H, m), 2.39–2.30 (2H, m), 2.00 (3H, s), 1.76–1.20 (84H, m), 0.90 (12H, t, J=6.6 Hz) Mass spectrum (m/z): 1485.9769 (M+Na)$^+$.

Test on macrophage activity inhibition (antagonist test).

TNFα is produced in vitro using human monocytic cell strain U937. The production amount of TNFα is determined by ELISA KIT of Genzyme Corporation.

Evaluation is carried out in accordance with the method of Daniel-Issakani, et al. (Journal of Biological Chemistry, 264, 20240–20247 (1989)).

By 10 ng/ml of LPS (lipopolysaccharide), about 1 ng of TNFα is produced per 10$^5$ cells of U937 during 6 hours (designated as a standard production amount: 100%).

In the presence of 10 ng/ml of LPS, the concentration of each of the compounds obtained in the Examples at which the production amount of TNFα is suppressed to 50% of the standard production amount is determined and it is expressed as ED$_{50}$%.

With regard to the cytotoxicity of each compound, cell viability of J774.1 cell six hours after the addition of each of the compounds obtained in Examples is measured by the MTT method. The concentration at which the cell viability is suppressed to 50% of that in the absence of the compound is expressed as IC$_{50}$. (The test results are reported in Table 2 below.) With ED$_{50}$/IC$_{50}$ as an index, the effect of the compounds of the present invention is confirmed.

TABLE 2

LPS antagonistic activities of the compounds on TNF α production by U937 cells.

| Compound | IC$_{50}$(nM) |
| --- | --- |
| Example 1 | 11 |
| Example 2 | 0.61 |
| Example 3 | 1.2 |
| Example 4 | 11 |
| Example 5 | 6.4 |
| Example 6 | 10 |

The lipid A 1-carboxylic acid compounds according to the present invention exhibit excellent macrophage activity inhibitory action and are useful as an anti-inflammatory agent, or a medicament against autoimmune diseases or septicemia. Thus, the present invention provides methods for treating or preventing inflammation, autoimmune diseases (particularly autoimmune diseases triggered by bacterial infection), and septicemia, by administering to a patient in need thereof, an effective amount of a compound of formula (I) or a pharmaceutically acceptable salt or ester thereof.

What is claimed is:
1. A compound of formula (I)

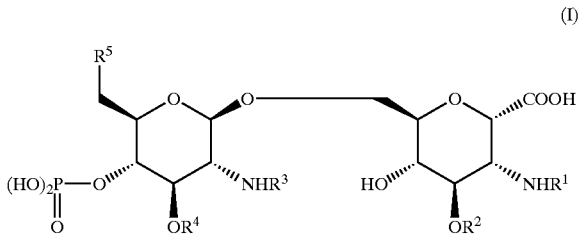

wherein:
- $R^1$ and $R^3$ may be the same or different and each is selected from the group consisting of a $C_1$–$C_{20}$ alkanoyl group which may optionally be substituted with one or more substituent groups selected from substituent group A, a $C_3$–$C_{20}$ alkenoyl group which may optionally be substituted with one or more substituent groups selected from substituent group A and a $C_3$–$C_{20}$ alkynoyl group which may optionally be substituted with one or more substituent groups selected from substituent group A;
- $R^2$ and $R^4$ may be the same or different and each is selected from the group consisting of a $C_1$–$C_{20}$ alkyl group which may optionally be substituted with one or more substituent groups selected from substituent group A, a $C_2$–$C_{20}$ alkenyl group which may optionally be substituted with one or more substituent groups selected from substituent group A and a $C_2$–$C_{20}$ alkynyl group which may optionally be substituted with one or more substituent groups selected from substituent group A;
- $R^5$ is selected from the group consisting of a hydrogen atom, a halogen atom, a hydroxy group, a $C_1$–$C_6$ alkoxy group which may optionally be substituted with an oxo group, a $C_2$–$C_6$ alkenyloxy group which may optionally be substituted with an oxo group, and a $C_2$–$C_6$ alkynyloxy group which may optionally be substituted with an oxo group; Substituent group A is a halogen atom, a hydroxy group, an oxo group, a $C_1$–$C_{20}$ alkoxy group which may optionally be substituted with an oxo group, a $C_2$–$C_{20}$ alkenyloxy group which may optionally be substituted with an oxo group, a $C_2$–$C_{20}$ alkynyloxy group which may optionally be substituted with an oxo group, a $C_1$–$C_{20}$ alkanoyloxy group which may optionally be substituted with an oxo group, a $C_3$–$C_{20}$ alkenoyloxy which may optionally be substituted with an oxo group or a $C_3$–$C_{20}$ alkynoyloxy group which may optionally be substituted with an oxo group;

or a pharmaceutically acceptable salt or ester thereof.

2. A compound according to claim 1 wherein $R^1$ is a $C_4$–$C_{18}$ alkanoyl group optionally substituted with one or more substituent groups selected from substituent group A, or a pharmaceutically acceptable salt or ester thereof.

3. A compound according to claim 1 wherein $R^1$ is a $C_8$–$C_{16}$ alkanoyl group optionally substituted with one or more substituent groups selected from substituent group A, or a pharmaceutically acceptable salt or ester thereof.

4. A compound according to claim 1 wherein $R^1$ is selected from the group consisting of an unsubstituted $C_{12}$–$C_{14}$ alkanoyl group and a $C_{12}$–$C_{14}$ alkanoyl group substituted with a hydroxy group, or a pharmaceutically acceptable salt or ester thereof.

5. A compound according to claim 1 wherein $R^1$ is selected from the group consisting of an unsubstituted lauroyl group, an unsubstituted myristoyl group, a lauroyl group substituted with a hydroxy group and a myristoyl group substituted with a hydroxy group, or a pharmaceutically acceptable salt or ester thereof.

6. A compound according to claim 1 wherein $R^2$ is a $C_4$–$C_{18}$ alkyl group optionally substituted with one or more substituent groups selected from substituent group A, or a pharmaceutically acceptable salt or ester thereof.

7. A compound according to claim 1 wherein $R^2$ is a $C_8$–$C_{16}$ alkyl group optionally substituted with one or more substituent groups selected from substituent group A, or a pharmaceutically acceptable salt or ester thereof.

8. A compound according to claim 1 wherein $R^2$ is selected from the group consisting of an unsubstituted $C_{12}$–$C_{14}$ alkyl group and a $C_{12}$–$C_{14}$ alkyl group substituted with a hydroxy group, or a pharmaceutically acceptable salt or ester thereof.

9. A compound according to claim 1 wherein $R^2$ is selected from the group consisting of an unsubstituted dodecyl group, an unsubstituted tetradecyl group, a dodecyl group substituted with a hydroxy group and a tetradecyl group substituted with a hydroxy group, or a pharmaceutically acceptable salt or ester thereof.

10. A compound according to claim 1 wherein $R^3$ is an unsubstituted $C_1$–$C_{16}$ alkanoyl group, or a pharmaceutically acceptable salt or ester thereof.

11. A compound according to claim 1 wherein $R^3$ is an unsubstituted $C_1$–$C_8$ alkanoyl group, or a pharmaceutically acceptable salt or ester thereof.

12. A compound according to claim 1 wherein $R^3$ is an unsubstituted $C_1$–$C_4$ alkanoyl group, or a pharmaceutically acceptable salt or ester thereof.

13. A compound according to claim 1 wherein $R^3$ is selected from the group consisting of an acetyl group and a propionyl group, or a pharmaceutically acceptable salt or ester thereof.

14. A compound according to claim 1 wherein $R^3$ is an acetyl group, or a pharmaceutically acceptable salt or ester thereof.

15. A compound according to claim 1 wherein $R^4$ is a $C_4$–$C_{18}$ alkyl group optionally substituted with one or more substituent groups selected from substituent group A, or a pharmaceutically acceptable salt or ester thereof.

16. A compound according to claim 1 wherein $R^4$ is a $C_8$–$C_{16}$ alkyl group optionally substituted with one or more substituent groups selected from substituent group A, or a pharmaceutically acceptable salt or ester thereof.

17. A compound according to claim 1 wherein $R^4$ is a $C_{12}$–$C_{14}$ alkyl group substituted with a substituent selected from a fluorine atom, a hydroxy group, an unsubstituted $C_{12}$–$C_{14}$ alkoxy group and an unsubstituted $C_{12}$–$C_{14}$ alkanoyloxy group, or a pharmaceutically acceptable salt or ester thereof.

18. A compound according to claim 1 wherein $R^4$ is selected from the group consisting of a dodecyl group substituted with a substituent selected from a dodecyloxy group and a tetradecyloxy group and a tetradecyl group substituted with a substituent selected from a dodecyloxy group and a tetradecyloxy group, or a pharmaceutically acceptable salt or ester thereof.

19. A compound according to claim 1 wherein $R^4$ is selected from the group consisting of a dodecyl group substituted with a substituent selected from a lauroyloxy group and a myristoyloxy group and a tetradecyl group substituted with a substituent selected from a lauroyloxy group and a myristoyloxy group, or a pharmaceutically acceptable salt or ester thereof.

20. A compound according to claim 1 wherein $R^5$ is selected from the group consisting of a halogen atom, a hydroxy group and an unsubstituted $C_1$–$C_6$ alkoxy group, or a pharmaceutically acceptable salt or ester thereof.

21. A compound according to claim 1 wherein $R^5$ is selected from the group consisting of a fluorine atom, a hydroxy group and a methoxy group, or a pharmaceutically acceptable salt or ester thereof.

22. A compound according to claim 1, wherein:

$R^1$ is a $C_4$–$C_{18}$ alkanoyl group optionally substituted with one or more substituent groups selected from substituent group A;

$R^2$ is a $C_4$–$C_{18}$ alkyl group optionally substituted with one or more substituent groups selected from substituent group A;

$R^3$ is an unsubstituted $C_1$–$C_{16}$ alkanoyl group;

$R^4$ is a $C_4$–$C_{18}$ alkyl group optionally substituted with one or more substituent groups selected from substituent group A; and $R^5$ is selected from the group consisting of a halogen atom, a hydroxy group and an unsubstituted $C_1$–$C_6$ alkoxy group;

or a pharmaceutically acceptable salt thereof.

23. A compound according to claim 1, wherein:

$R^1$ is a $C_8$–$C_{16}$ alkanoyl group optionally substituted with one or more substituent groups selected from substituent group A;

$R^2$ is a $C_8$–$C_{16}$ alkyl group optionally substituted with one or more substituent groups selected from substituent group A;

$R^3$ is an unsubstituted $C_1$–$C_8$ alkanoyl group;

$R^4$ is a $C_8$–$C_{16}$ alkyl group optionally substituted with one or more substituent groups selected from substituent group A; and $R^5$ is selected from the group consisting of a halogen atom, a hydroxy group and an unsubstituted $C_1$–$C_6$ alkoxy group;

or a pharmaceutically acceptable salt thereof.

24. A compound according to claim 1, wherein:

$R^1$ is selected from the group consisting of an unsubstituted $C_{12}$–$C_{14}$ alkanoyl group and a $C_{12}$–$C_{14}$ alkanoyl group substituted with a hydroxy group;

$R^2$ is selected from the group consisting of an unsubstituted $C_{12}$–$C_{14}$ alkyl group and a $C_{12}$–$C_{14}$ alkyl group substituted with a hydroxy group;

$R^3$ is an unsubstituted $C_1$–$C_4$ alkanoyl group;

$R^4$ is a $C_{12}$–$C_{14}$ alkyl group substituted with a substituent selected from a fluorine atom, a hydroxy group, an unsubstituted $C_{12}$–$C_{14}$ alkoxy group and an unsubstituted $C_{12}$–$C_{14}$ alkanoyloxy group; and $R^5$ is selected from the group consisting of a fluorine atom, a hydroxy group and a methoxy group;

or a pharmaceutically acceptable salt thereof.

25. A compound according to claim 1, wherein:

$R^1$ is selected from the group consisting of an unsubstituted lauroyl group, an unsubstituted myristoyl group, a lauroyl group substituted with a hydroxy group and a myristoyl group substituted with a hydroxy group;

$R^2$ is selected from the group consisting of an unsubstituted dodecyl group, an unsubstituted tetradecyl group, a dodecyl group substituted with a hydroxy group and a tetradecyl group substituted with a hydroxy group;

$R^3$ is selected from the group consisting of an acetyl group and a propionyl group;

$R^4$ is selected from the group consisting of a dodecyl group substituted with a substituent selected from a dodecyloxy group and a tetradecyloxy group and a tetradecyl group substituted with a substituent selected from a dodecyloxy group and a tetradecyloxy group; and $R^5$ is selected from the group consisting of a fluorine atom, a hydroxy group and a methoxy group;

or a pharmaceutically acceptable salt thereof.

26. 2,6-Anhydro-7-O-[2-acetylamino-2-deoxy-6-O-methyl-4-O-phosphono-3-O-{(R)-3-tetradecanoyloxytetradecyl}-β-D-glucopyranosyl]-3-{(R)-3-hydroxytetradecanoylamino}-4-O-{(R)-3-hydroxytetradecyl}-3-deoxy-D-glycero-D-ido-heptonic acid according to claim 1, or a pharmaceutically acceptable salt thereof.

27. 2,6-Anhydro-7-O-[2-acetylamino-2-deoxy-4-O-phosphono-3-O-{(R)-3-tetradecanoyloxytetradecyl}-β-D-glucopyranosyl]-3-f{(R)-3-hydroxytetradecanoylamino}-4-O-{(R)-3-hydroxytetradecyl}-3-deoxy-D-glycero-D-ido-heptonic acid according to claim 1, or a pharmaceutically acceptable salt thereof.

28. 2,6-Anhydro-7-O-[2-acetylamino-2,6-deoxy-6-fluoro-4-O-phosphono-3-O-{(R)-3-tetradecanoyloxytetradecyl}-β-D-glucopyranosyl]-3-{(R)-3-hydroxytetradecanoylamino}-4-O-{(R)-3-hydroxytetradecyl}-3-deoxy-D-glycero-D-ido-heptonic acid according to claim 1, or a pharmaceutically acceptable salt thereof.

29. 2,6-Anhydro-7-O-[2-acetylamino-2-deoxy-3-O-{(R)-3-dodecyloxytetradecyl}-6-O-methyl4-O-phosphono-β-D-glucopyranosyl]-3-{(R)-hydroxytetradecanoylamino}-4-O-{(R)-3-hydroxytetradecyl}-3-deoxy-D-glycero-D-ido-heptonic acid according to claim 1, or a pharmaceutically acceptable salt thereof.

30. 2,6-Anhydro-7-O-[2-acetylamino-2-deoxy-3-O-{(R)-3-dodecyloxytetradecyl}-4-O-phosphono-β-D-glucopyranosyl]-3-{(R)-hydroxytetradecanoylamino}-4-O-{ (R)-3-hydroxytetradecyl}-3-deoxy-D-glycero-D-ido-heptonic acid according to claim 1, or a pharmaceutically acceptable salt thereof.

31. 2,6-Anhydro-7-O-[2-acetylamino-2,6-dideoxy-3-O-{(R)-3-dodecyloxytetradecyl}-6-fluoro-4-O-phosphono-β-D-glucopyranosyl]-3-{(R)-3-hydroxytetradecanoylamino}4-O-{(R)-3-hydroxytetradecyl}-3-deoxy-D-glycero-D-ido-heptonic acid according to claim 1, or a pharmaceutically acceptable salt thereof.

32. A pharmaceutical composition comprising an effective amount of a pharmacologically active compound together with a carrier therefor, wherein said pharmacologically active compound is a compound according to any one of claims 1 to 31.

33. A method for the treatment or prophylaxis of an inflammatory disorder in a human, which comprises administering to a human in need of such treatment an effective amount of a compound according to any one of claims 1 to 31 or a pharmaceutically acceptable salt or ester thereof.

34. A method for the treatment or prophylaxis of an autoimmune disease which is triggered by a bacteria in a human, which comprises administering to a human in need of such treatment an effective amount of a compound according to any one of claims 1 to 31 or a pharmaceutically acceptable salt or ester thereof.

35. A method for the treatment or prophylaxis of septicemia in a human, which comprises administering to a human in need of such treatment an effective amount of a compound according to any one of claims 1 to 31 or a pharmaceutically acceptable salt or ester thereof.

* * * * *